US008637470B2

(12) United States Patent
Cohen et al.

(10) Patent No.: US 8,637,470 B2
(45) Date of Patent: Jan. 28, 2014

(54) SMALL HUMANIN-LIKE PEPTIDES

(75) Inventors: Pinchas Cohen, Pacific Palisades, CA (US); Laura J. Cobb, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/989,688

(22) PCT Filed: May 1, 2009

(86) PCT No.: PCT/US2009/042589
§ 371 (c)(1),
(2), (4) Date: Oct. 26, 2010

(87) PCT Pub. No.: WO2009/135165
PCT Pub. Date: Nov. 5, 2009

(65) Prior Publication Data
US 2011/0039771 A1    Feb. 17, 2011

Related U.S. Application Data

(60) Provisional application No. 61/126,251, filed on May 1, 2008.

(51) Int. Cl.
*A61K 38/17*      (2006.01)
*C07K 14/435*   (2006.01)

(52) U.S. Cl.
USPC .......................................... 514/21.3; 530/324

(58) Field of Classification Search
None
See application file for complete search history.

(56) References Cited

U.S. PATENT DOCUMENTS

| 6,277,974 | B1 | 8/2001 | Lo et al. | |
| 7,053,053 | B2 * | 5/2006 | Sugo et al. | 514/18.9 |
| 7,314,864 | B1 | 1/2008 | Nishimoto | |
| 2003/0175819 | A1 | 9/2003 | Reed et al. | |
| 2004/0152101 | A1 | 8/2004 | Sugo et al. | |
| 2006/0100253 | A1 | 5/2006 | Niestroj | |
| 2007/0083334 | A1 * | 4/2007 | Mintz et al. | 702/19 |
| 2012/0219578 | A1 * | 8/2012 | Galeotti et al. | 424/190.1 |

FOREIGN PATENT DOCUMENTS

| DE | 19845251 A1 * | 3/2000 |
| WO | WO 01/81361 A1 | 11/2001 |

OTHER PUBLICATIONS

Machine English Translation of DE 19845251 A1 provided by EPO Espacenet, Jan. 15, 2012; pp. 1-5.*
Yan M et al. (2000) Two-amino acid molecular switch in an epithelial morphogen that regulatess binding to two distinct receptors. Science, 290:523-527.*
Zhu Z et al. (2006) Expression of PTEN, p27, p21 and AKT mRNA and protein in human BEL-7402 hepatocarcinoma cells in transplanted tumors of nude mice treated with the tripeptide tyroservatide (YSV). Int. J. Cancer, 118:1539-1544.*
Kariya, S. et al., "Humanin Inhibits Cell Death of Serum-Deprived PC12h Cells," NeuroReport, May 7, 2002, pp. 903-907, vol. 13, No. 6.
Lindstad, T. "Identification and Characterization of Genes That Are Common in Prostate Cancer and Adipocyte Cell Lines," Thesis, Department of Molecular Biosciences, University of Oslo, May 2005, 62 pages, [Online] [Retrieved on Oct. 27, 2009], Retrieved from the Internet<URL:www.duo.uio.no/publ/biokjemi/2005/27569/27569.pdf>.
PCT International Search Report and Written Opinion, PCT Application No. PCT/US09/42589, Nov. 9, 2009, 12 pages.

* cited by examiner

*Primary Examiner* — Kimberly A Ballard
(74) *Attorney, Agent, or Firm* — Morgan, Lewis & Bockius LLP; Annette S. Parent

(57) ABSTRACT

Novel peptides referred to as small humanin-like peptides (SHLPs) are provided herein along with nucleic acids encoding SHLPs and probes that selectively bind SHLPs. SHLPs have wide-ranging activity, including neuroprotective activity, anticancer activity, and cell survival activity. Also provided herein are therapeutic methods comprising administering an effective amount of an SHLP to a subject in need of treatment.

2 Claims, 23 Drawing Sheets

SMALL HUMANIN-LIKE PEPTIDES

CROSS-REFERENCE TO RELATED APPLICATIONS

This application claims the benefit of Provisional Application No. 61/126,251, filed on May 1, 2008, the entirety of which is incorporated herein by reference.

FIELD OF THE INVENTION

Provided herein are a series of novel peptides encoded near the humanin locus in mitochondrial DNA, and fragments, derivatives, and variants thereof, which have neuroprotective, anticancer, and other beneficial activities. Also provided herein are isolated nucleic acids encoding such peptides, antibodies that selectively bind such peptides, agents that modulate the activity and/or expression of such peptides, and therapeutic methods involving the administration of such peptides, antibodies and agents.

BACKGROUND OF THE INVENTION

In 2001, Nishimoto and colleagues identified humanin (HN), a novel 24-amino-acid peptide encoded from the 16S ribosomal RNA region of the mitochondrial DNA, and described it to be a potent neurosurvival factor capable of antagonizing Alzheimer's disease-related cell death insults (Hashimoto et al., *Proc Natl Acad Sci USA*, 98: 6336-41 (2001)). Humanin has also been described as a Bax antagonist that induces survival in various cancer cells (Guo et al., *Nature*, 423: 456-61 (2003)) and as an IGFBP-3 partner that antagonizes the apoptotic actions of IGFBP-3 on cancer cells (Ikonen et al., *Proc Natl Acad Sci USA*, 100:13042-13047 (2003)). Additional work has indicated that humanin is a wide spectrum survival factor (Nishimoto et al., *Trends Mol Med.*, 10:102-5 (2004)), but its exact mechanism of action remains unclear.

The humanin cDNA shares complete identity with the mitochondrial 16S rRNA gene but spans only about half the length of the ribosomal RNA. Humanin transcripts of mitochondrial origin are present in kidney, testis, brain, and the gastrointestinal tract. Interestingly, humanin is highly conserved among species (between 90-100% homology), including lower organisms.

Novel mutants and analogs of humanin with enhanced potency have been described, including HNG (S14G) (Hashimoto et al., J. Neurosci., 21: 9235-9245 (2001) and Terashita et al., J. Neurochem., 85: 1521-1538 (2003)), HNG-F6A (non-IGFBP-3 binding) (Ikonen et al., *Proc Nat Acad Sci.*, 100: 13042-13047 (2003)) and colivelin (hybrid peptide containing partial sequences of HN and ADNF9). Humanin and its analogues and derivatives have shown therapeutic potential for an array of diseases including Alzheimer's disease, diabetes and kidney failure.

BRIEF SUMMARY

Provided herein are novel peptides, termed small humanin-like peptides (SHLPs), comprising an amino acid sequence selected from the group consisting of: SEQ ID NOs: 8, 9, 10, 11, 12, and 13. Also provided herein are variants of an SHLP, comprising an amino acid sequence having at least 60%, at least 65%, at least 70%, at least 75%, at least 80%, or at least 85% sequence identity to an amino acid sequence selected from the group consisting of: SEQ ID NO: 8, 9, 10, 11, 12, and 13.

In some aspects, the variant has at least one therapeutic activity exhibited by the SHLP selected from the group consisting of: SEQ ID NO: 8, 9, 10, 11, 12, and 13 to which it has at least 60%, at least 65%, at least 70%, at least 75%, at least 80%, or at least 85% sequence identity. In some aspects, the variant has identity to an amino acid sequence selected from the group consisting of: SEQ ID NOs: 8, 9, 10, 11, and 12, and the at least one therapeutic activity is inhibiting cell death induced by a neurodegenerative disease.

In some aspects, the variant has identity to an amino acid sequence selected from the group consisting of: SEQ ID NOs: 8, 9, 10, 11, and 12, and the at least one therapeutic activity is inhibiting cell death induced by a neurodegenerative disease. In further aspects, the therapeutic activity is inhibiting cell death induced by amyloid-beta (Aβ) peptides in Alzheimer's disease.

In some aspects, the variant has identity to an amino acid sequence selected from the group consisting of: SEQ ID NOs: 8, 9, 10, 11, and 12, and the at least one therapeutic activity is inhibiting apoptosis in pancreatic β-cells.

In some aspects, the variant has identity to an amino acid sequence selected from the group consisting of: SEQ ID NOs: 9 and 10, and the at least one therapeutic activity is stimulating insulin-induced differentiation of adipocytes.

In some aspects, the variant has identity to an amino acid sequence selected from the group consisting of: SEQ ID NOs: 9 and 10, and the at least one therapeutic activity is enhancing cellular resistance to environmental stress.

In some aspects, the variant has identity to an amino acid sequence selected from the group consisting of: SEQ ID NOs: 9 and 10, and the at least one therapeutic activity is inhibiting intracellular production of reactive oxygen species (ROS).

In some aspects, the variant has identity to the amino acid sequence of SEQ ID NO:13, and the at least one therapeutic activity is anticancer activity. In further aspects, the anticancer activity is against prostate cancer and/or breast cancer. In yet further aspects, the anticancer activity is selected from the group consisting of: inducing apoptosis in cancer cells, inhibiting proliferation of cancer cells, inhibiting tumor growth, and inhibiting angiogenesis.

Also provided herein are variants of SHLPs comprising an amino acid sequence having at least 85% sequence identity to an amino acid sequence selected from the group consisting of: SEQ ID NOs: 8, 9, 10, 11, 12, and 13. In various aspects, the variants comprise the amino acid sequence of SEQ ID NO:8, SEQ ID NO:9, SEQ ID NO:10, SEQ ID NO:11, SEQ ID NO:12, and SEQ ID NO:13.

In another aspect, pharmaceutical compositions are provided herein comprising (i) a small humanin-like peptide (SHLP) having an amino acid sequence selected from the group consisting of: SEQ ID NOs: 8, 9, 10, 11, 12, and 13, or a variant of an SHLP comprising an amino acid sequence having at least 85% identity to an amino acid sequence selected from the group consisting of: SEQ ID NOs: 8, 9, 10, 11, 12, and 13; and (ii) at least one pharmaceutically acceptable excipient.

Also provided herein are methods of treating cancer, comprising administering, to a patient in need of treatment, an effective amount of a small humanin-like peptide (SHLP) having the amino acid sequence of SEQ ID NO:13, or a variant of a SHLP comprising an amino acid sequence having at least 85% identity to the amino acid sequence of SEQ ID NO:13. In some aspects, the cancer is selected from the group consisting of: breast cancer and prostate cancer.

Methods are provided herein for treating diabetes mellitus, the methods comprising administering, to a patient in need of treatment, an effective amount of a small humanin-like peptide (SHLP) having an amino acid sequence of SEQ ID NO:9 or SEQ ID NO:10, or a variant of a SHLP comprising an amino acid sequence having at least 85% identity to the amino acid sequence of SEQ ID NO:9 or SEQ ID NO:10.

Methods are further provided herein for treating a neurodegenerative disease, the methods comprising administering, to a patient in need of treatment, an effective amount of a small humanin-like peptide (SHLP) having an amino acid sequence selected from the group consisting of: SEQ ID NOs: 8, 9, 10, and 11, or a variant of an SHLP comprising an amino acid sequence having at least 85% identity to an amino acid sequence selected from the group consisting of: SEQ ID NOs: 8, 9, 10, and 11.

Also provided herein are isolated polynucleotides, comprising a nucleic acid sequence encoding a small humanin-like peptide (SHLP) having an amino acid sequence selected from the group consisting of: SEQ ID NOs: 8, 9, 10, 11, 12, and 13, or a variant of a SHLP comprising an amino acid sequence having at least 85% identity to an amino acid sequence selected from the group consisting of: SEQ ID NOs: 8, 9, 10, 11, 12, and 13. In various aspects, the isolated polynucleotides comprise a nucleic acid sequence selected from the group consisting of: SEQ ID NOs: 1, 2, 3, 4, 5, 6, 7, and 8.

Host cells are also provided herein, wherein the host cells are transformed with an isolated polynucleotide comprising a nucleic acid sequence encoding a small humanin-like peptide (SHLP) having an amino acid sequence selected from the group consisting of: SEQ ID NOs: 8, 9, 10, 11, 12, and 13, or a variant of a SHLP comprising an amino acid sequence having at least 85% identity to an amino acid sequence selected from the group consisting of: SEQ ID NOs: 8, 9, 10, 11, 12, and 13.

DETAILED DESCRIPTION OF ILLUSTRATIVE ASPECTS

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. Examples provided herein are illustrative only and not intended to be limiting.

Figure 1:
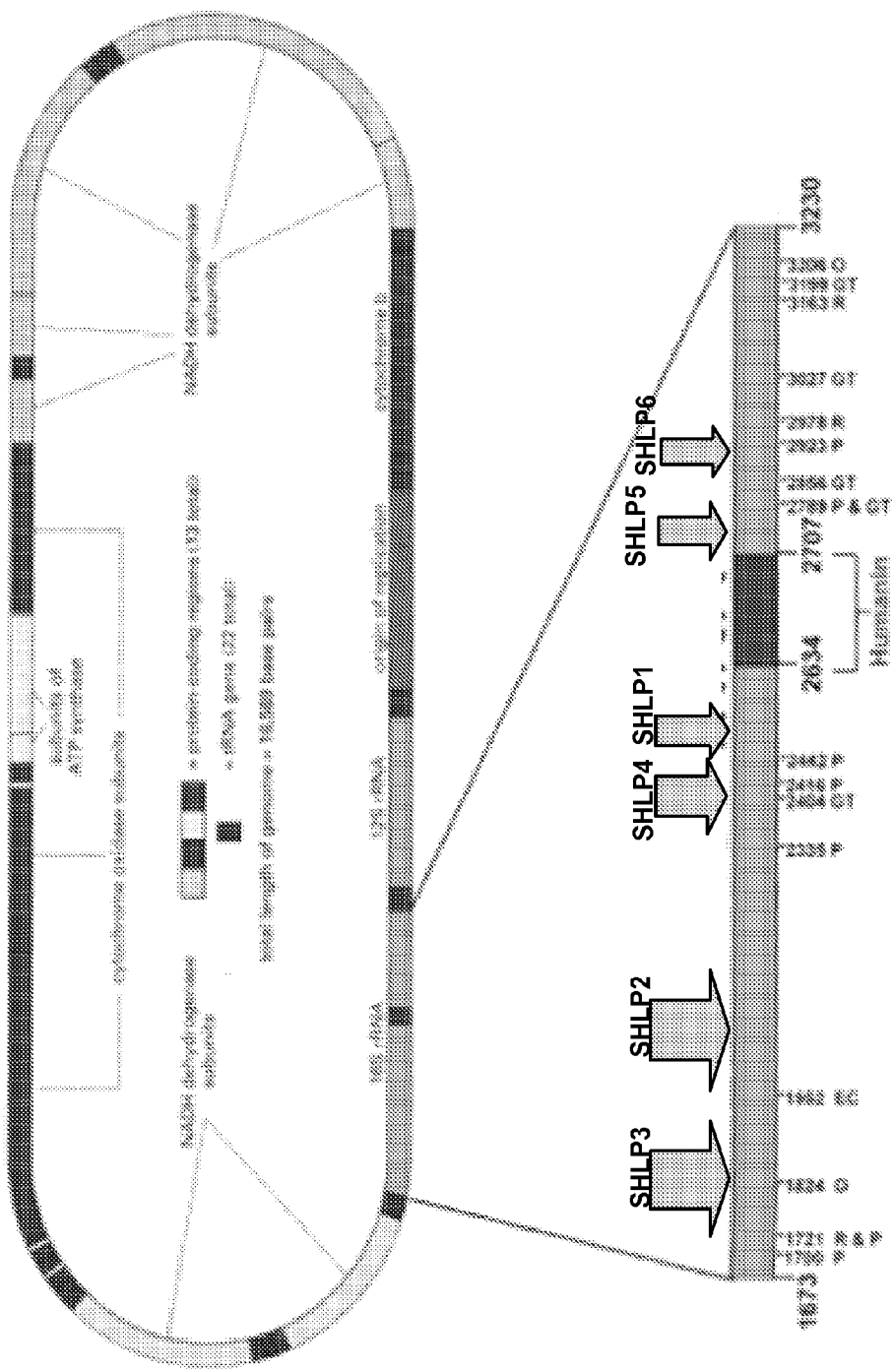
FIG. 1. A cartoon outlining the localization of humanin, and SHLPs within the mitochondrial chromosome. HN is shown as a dark rectangle relative to the enlarged 16S rRNA region within the mitochondrial genome. The six SHLPs are indicated by arrows. Also shown, are sites where mutations in several cancers (including prostate, breast and ovary) have been identified in the 16S rRNA region.

The present invention is related to the discovery of a number of open reading frames (ORFs) near the humanin locus in mitochondrial DNA that encode a series of previously uncharacterized polypeptides. The genomic organization of human mitochondrial DNA (mtDNA) is shown in FIG. 1, including the 16s rRNA gene sequence and the location of the ORF within the 16s rRNA gene which encodes humanin. A detailed study of the 16s rRNA sequence revealed additional ORFs encoding six putative peptides (FIG. 1), referred to herein as SHLPs 1-6. The peptide sequences of SHLPs 1-6 and humanin are shown in table 1 along with the locations of the corresponding ORFs within the mtDNA. SHLPs 1-6 and fragments, derivatives, and variants thereof are collectively referred to herein as "small humanin-like peptides" or "SHLPs."

TABLE 1

Sequence characteristics of HN and SHLPs

| Peptide | Location within mtDNA | SEQ ID (nt) | SEQ ID (aa) | Amino Acid sequence |
| --- | --- | --- | --- | --- |
| SHLP1 | 2490-2561 | 1 | 8 | MCHWAGGASNTGDARGDVFGKQAG |
| SHLP2 | 2092-2170 | 2 | 9 | MGVKFFTLSTRFFPSVQRAVPLWTNS |
| SHLP3 | 1707-1821 | 3 | 10 | MLGYNFSSFPCGTISIAPGFNFYRLYFIWVNGLAKVVW |
| SHLP4 | 2446-2524 | 4 | 11 | MLEVMFLVNRRGKICRVPFTFFNLSL |
| SHLP5 | 2785-2856 | 5 | 12 | MYCSEVGFCSEVAPTEIFNAGLVV |
| SHLP6 | 2992-3051 | 6 | 13 | MLDQDIPMVQPLLKVRLFND |
| HN | 2634-2707 | 7 | 14 | MAPRGFSCLLLLTSEIDLPVKRRA |

Although humanin was first discovered within the mitochondrial 16S rRNA gene sequence, subsequent studies have identified a several copies of the humanin ORF in the nuclear genome and have shown that humanin cDNAs are transcribed by both mitochondrial and cytosolic ribosomes (e.g., Guo et al., Nature, 423: 456-61 (2003)). The amino acid sequences of mitochondrial humanin and several nuclear humanin analogues are provided in Table 2. Mitochondrial-derived humanin shares 92-95% identity with the nuclear-encoded cDNAs. Humanin has been demonstrated in brain and testis, and has been shown to be present at concentrations of 1-10 ng/ml in plasma, CSF and seminal fluid (Ikonen et al., Proc Nat Acad Sci., 100: 13042-13047 (2003)).

TABLE 2

Amino acid sequences of HN peptides

| Peptide | Amino acid sequence | SEQ ID (nt) | SEQ ID (aa) |
| --- | --- | --- | --- |
| Humanin (M) | MAPRGFSCLLLLTSEIDLPVKRRA | 7 | 14 |
| Humanin (3) | MAPRGFSCLLLSTSEIDLPVKRRA | 15 | 19 |
| Humanin (11) | MAPRGFSCLLLSTSEIDLPVKRRA | 16 | 20 |
| Humanin (5) | MAPRGFSCLLLSTSEIDLPVKR.. | 17 | 21 |
| Humanin (7) | MTPRGFSCLLLPTSETDLPVKRR. | 18 | 22 |

Since the humanin coding sequence is represented in both mithochondrial and genomic DNA, human genomic DNA was searched with the coding sequences of SHLPs 1-6 to assess whether SHLPs may have a similar distribution. Multiple, highly homologous copies of the SHLP coding sequences were found within the genomic DNA. The coding sequences listed in Table 4 occurred within ORFs associated with a Kozak consensus sequence for the initiation of eukaryotic translation (Kozak, Mamm. Genome, 7:563-574 (1996)).

The amino acid sequences of the encoded peptides and the mitochondrial SHLPs are provided in Table 3 (with chromosomal or mitochondrial origin indicated in parentheses). Without being limited by a particular theory, it is believed that both mitochondrial and genomic SHLPs are expressed in vivo and perform a wide range of functions in various cells and tissues. References made herein to "SHLPs" include nucleic acids of both mitochondrial and genomic origin, their encoded peptides, and variants of such nucleic acids and peptides. In some preferred aspects, SHLPs of genomic origin provided herein share at least one activity with a homologous mitochondrial SHLP.

TABLE 3

Amino acid sequences of human SHLPs

| SHLP | Amino acid sequence | SEQ ID (aa) |
|---|---|---|
| SHLP1 (M) | MCHWAGGASNTGDARGDVFGKQAG | 8 |
| SHLP2 (M) | MGVKFFTLSTRFFPSVQRAVPLWTNS | 9 |
| SHLP2 (5) | MGIKFFTLFTRFFPSVQRAVPLWTNS | 23 |
| SHLP3 (M) | MLGYNFSSFPCGTISIAPGFNFYRLYFIWVNGLAKVVW | 10 |
| SHLP4 (M) | MLEVMFLVNRRGKICRVPFTFFNLSL | 11 |
| SHLP4 (7) | MLEVMFLVNRRGKICRVPFTFFNLSL | 24 |
| SHLP4 (3) | MLEVMFLVNRRGKICRVPFTFFNLSL | 25 |
| SHLP4 (11) | MLEVMFLVNRRGKICRVPFTFFNLSL | 26 |
| SHLP4 (6) | MLEVMFLVNRRGKICRVPFTFFNLSL | 27 |
| SHLP4 (5) | MLEVMFLVNRWGKVCRVPFTFFNLSL | 28 |
| SHLP4 (7) | MLEVMFLVNRQGKICRVPFNFF.... | 29 |
| SHLP4 (4) | MLEVMFLVNRQGKIC.VPFTFCKLSL | 30 |
| SHLP4 (9) | MLEVMFLVNRWGKICRVPFTFCNISL | 31 |
| SHLP4 (17) | MLEVMFLINRRGKIR.VPFTFFNLSL | 32 |
| SHLP4 (X) | MLEVMFLVNRRGKICGVPFTFCILSL | 33 |
| SHLP4 (17) | MLEVMFLVNRQDKIC.VPFTFCNLSL | 34 |
| SHLP4 (10) | MLEVMFLVNRRGKIG.IPFTFCNLSL | 35 |
| SHLP4 (20) | MLEVMFLVNRRGKIC.VPFIF..... | 36 |
| SHLP4 (17) | MLAVMFLVNKLGKICRVPFTVCNLSL | 37 |
| SHLP4 (10) | ....VFLVNRQSMICRVPFTFCNLSL | 38 |
| SHLP4 (2) | MLEVVFLVNRQGKICQFPFTFCNLSL | 39 |
| SHLP4 (8) | MLEVMFLVNRRDKICQVPFTFCNFSL | 40 |
| SHLP4 (10) | MLGVMFLVERWGEMCRVPFTFCNLSL | 41 |
| SHLP5 (M) | MYCSEVGFCSEVAPTEIFNAGLVV | 12 |
| SHLP6 (M) | MLDQDIPMVQPLLKVRLFND | 13 |
| SHLP6 (17) | MLDQDIPMVQPLLKVRLFND | 42 |
| SHLP6 (4) | MLDQDILMV.LLLRVRLFND | 43 |
| SHLP6 (7) | MLDQDILIVQPLLRVHLFND | 44 |
| SHLP6 (4) | MLDQDMLMVQPLSKVRLFND | 45 |
| SHLP6 (2) | MLDQDIQMV.PLLRVCLFKD | 46 |
| SHLP6 (14) | MLDQDVLMV.PLIRVRLFND | 47 |
| SHLP6 (9) | MLDQDILMV.PLLRVHLFND | 48 |

TABLE 4

Nucleic acid sequences of human SHLPs

| SHLP | Nucleic acid sequence | SEQ ID (nt) |
|---|---|---|
| SHLP1 (M) | TTACCCCGCCTGTTTACCAAAAACATCACCTCTAGCATCACCAGTATTAGAGGCACCGCCTGCCCAGTGACACAT | 1 |
| SHLP2 (M) | TTAACTGTTAGTCCAAAGAGGAACAGCTCTTTGGACACTAGGAAAAAACCTTGTAGAGAGAGTAAAAAATTTAACACCCAT | 2 |
| SHLP2 (5) | TTAACTGTTAGTCCAAAGAGGAACAGCTCTTTGGACACTAGGAAAAAACCTTGTAAAGAGAGTAAAAAATTTAATACCCAT | 49 |
| SHLP3 (M) | CTACCAGACAACCTTAGCCAAACCATTTACCCAAATAAAGTATAGGCGATAGAAATTGAAACCTGGCGCAATAGATATAGTACCGCAAGGGAAAGATGAAAAATTATAACCAAGCAT | 3 |
| SHLP4 (M) | TCATAAGGAAAGGTTAAAAAAAGTAAAAGGAACTCGGCAAATCTTACCCCGCCTGTTTACCAAAAACATCACCTCTAGCAT | 4 |
| SHLP4 (7) | ATAAGGAAAGGTTAAAAAAAGTAAAAGGAACTCGGCAAATCTTACCCCGCCTGTTTACCAAAAACATCACCTCTAGCAT | 50 |
| SHLP4 (3) | TCATAAGGAAAGGTTAAAAAAAGTAAAAGGAACTCGGCAAATCTTACCCCGCCTGTTTACCAAAACATCACCTCTAGCAT | 51 |
| SHLP4 (11) | TCATAAGGAAAGGTTAAAAAAAGTAAAAGGAACTCGGCAAATCTTACCCCGCCTGTTTACCAAAACATCACCTCTAGCAT | 52 |
| SHLP4 (6) | TCATAAGGAAAGGTTAAAAAAAGTAAAAGGAACTCGGCAAATCTTACCCCGCCTGTTTACCAAAACATCACCTCTAGCAT | 53 |
| SHLP4 (5) | AAGGAAAGGTTAAAAAAAGTAAAAGGAACTCGGCAAACCTTACCCCACCTGTTTACCAAAAACATCACCTCTAGCAT | 54 |
| SHLP4 (7) | TAAGGAAAGGTTAAAAAAAATTAAAAGGAACTCGGCAAATTTTACCCTGCCTGTTTACCAAAAACATCACCTCTAGCAT | 55 |
| SHLP4 (4) | TAAGGAAAGTTTACAAAAAGTAAAAGGAACTCAGCAAATCTTACCCTGCCTGTTTACCAAAAACATCACCTCTAGCAT | 56 |
| SHLP4 (9) | TAAGGAAATATTACAAAAAGTAAAAGGAACTCGGCAAATCTTACCCCACCTGTTTACCAAAAACATCACCTCTAGCAT | 57 |
| SHLP4 (17) | AAGGAAAGGTTAAAAAAAGTAAAAGGAACTCAGCGAATCTTACCCCTCCTGTTTATCAAAAACATCACCTCTAGCAT | 58 |

TABLE 4-continued

Nucleic acid sequences of human SHLPs

| SHLP | Nucleic acid sequence | SEQ ID (nt) |
|---|---|---|
| SHLP4 (17) | TAAGGAAAGATTACAAAAAGTAAAAGGAACTC AGCAAATCTTATCCTGCCTGTTTACCAAAAACAT CACCTCTAGCAT | 59 |
| SHLP4 (10) | TAAGGAAAGATTACAAAAAGTAAAAGGAATTCA GCCAATCTTACCCCGCCTGTTTACCAAAAACATC ACCTCTAGCAT | 60 |
| SHLP4 (20) | TAAGGAAACATTACAAAAAATAAAAGGAACTC AGCAAATCTTACCCCGCCTGTTTACCAAAAACAT CACCTCTAGCAT | 61 |
| SHLP4 (17) | TAAGGAAAGATTACAAACAGTAAAAGGAACTCG GCAAATCTTACCCAGCTTGTTTACCAAAAACATC ACCGCTAGCAT | 62 |
| SHLP4 (10) | TAAGGAAAGATTACAAAAAGTAAAAGGAACTC GGCAAATCATACTCTGCCTGTTTACCAAAAACA- CACCTCTAGCAT | 63 |
| SHLP4 (2) | TAAGGAAAGATTACAAAAAGTAAAAGGAAATT GGCAAATCTTACCTTGCCTGTTTACCAAAAACAC CACCTCTAGCAT | 64 |
| SHLP4 (8) | TAAGGAAAAATTACAAAAAGTAAAAGGAACTTG GCAAATCTTGTCCCGCCTATTTACCAAAAACATC ACCTCTAGCAT | 65 |
| SHLP4 (10) | TAAGGAAAGATTACAAAAAGTAAAAGGAACTC GGCACATTTCACCCCATCTCTCTACCAAAAACAT CACCCCTAGCAT | 66 |
| SHLP4 (X) | TAAGGAAAGATTTTTTAAAAAGTAAAAGGAACT CAGCAAAAGGAAACCCGTCTTGTTTACCAAAAA CATCACCTCTAGCAT | 67 |
| SHLP5 (M) | CTAAACTACCAAACCTGCATTAAAAATTTCGGTT GGGGCGACCTCGGAGCAGAACCCAACCTCCGAG CAGTACAT | 5 |
| SHLP6 (M) | ATGTTGGATCAGGACATCCCAATGGTGCAGCCG CTATTAAAGGTTCGTTTGTTCAACGATTAA | 6 |
| SHLP6 (17) | ATGTTGGATCAGGACATCCCAATGGTGCAGCCG CTATTAAAGGTTCGTTTGTTCAACGATTAA | 68 |
| SHLP6 (4) | ATGTTGGATCAGGACATCCTAATGGTGTAGCTG CTATTAAGGGTTCGTTTGTTCAATGATTAA | 69 |
| SHLP6 (7) | ATGTTGGATCAGGACATCCTAATTGTACAGCCA CTATTAAGGGTTCATTTGTTCAACGATTAA | 70 |
| SHLP6 (4) | ATGTTGGATCAGGACATGCTGATGGTGCAGCCG CTATCAAAGGTTCGTTTGTTCAATGATT | 71 |
| SHLP6 (2) | ATGTTGGATCAGGACATCCAAATGGTGTAGCCA CTATTAAGGGTTTGTCTGTTCAAAGATTAA | 72 |
| SHLP6 (14) | ATGTTGGATCAGGACGTCCTAATGGTGTAGCCG CTAATAAGGGTTCGTTTGTTCAATGATCAA | 73 |
| SHLP6 (9) | ATGTTGGATCAGGACATCCTAATGGTGTAGCCG CTATTAAGGGTTCATTTATTCAATGATTAA | 74 |

Mitochondrial SHLPs 1-6 are small peptides of 24, 26, 38, 26, 24, and 20-amino acids, respectively, transcribed from within the 16s rRNA gene of the mtDNA. Tables 5 and 6 contain amino acid and nucleic acid sequences, respectively, of both mitochondrial and genomic SHLPs across a range of species, including but not limited to, primates, guinea pigs, cats, dogs, horses, rats, and mice. SHLPs are generally highly conserved among species, including lower vertebrates. SHLP1 variants include truncated peptides comprising residues 1-21 of the mitochondrial peptide, as well as peptides that are C-terminally extended by up to about 10 residues. SHLP2 variants include truncated peptides comprising the N-terminal β-16 residues of the mitochondrial peptide. SHLP4 variants include truncated peptides comprising the N-terminal 10-22 residues of the mitochondrial peptide, as well as peptides that are C-terminally extended by about 3 to about 30 residues. SHLP6 variants include truncated peptides comprising residues 1-9 of the mitochondrial peptide, as well as peptides that are C-terminally extended by about 3 to about 6 residues. References made herein to "SHLPs" include both truncated and extended variants, such as but not limited to, the peptides set forth in Table 5 and variants thereof

TABLE 5

Amino acid sequences of non-human SHLPs

| SHLP | Species | Amino acid sequence | SEQ ID (aa) |
|---|---|---|---|
| SHLP1 (M) | Chimp | MCHRAGGASNTGNARGDVFGKQAG | 75 |
| SHLP1 (M) | Orangutan | MCHRAGGASNTGNARGDVFGKQAG | 76 |
| SHLP1 (5) | Rhesus | MC-WAGSDSHTGNARGDVFGKQMG | 77 |
| SHLP1 (8) | Rhesus | MCHWAGGASNTGNARGDVFGK | 78 |
| SHLP1 (16) | Rhesus | MCHWAGSASNTSNARGDVFGKQAEVKFAE FLLLF | 79 |
| SHLP1 (18) | Rhesus | MCQWAGGASNTGNASGDVFGKQAGLSLLS SFYFF | 80 |
| SHLP1 (149667) | Cat | MSLGRPCL-NTKNARGDVIGKQAGSVFVESLLLLLIFL | 81 |
| SHLP2 (M) | Chimp | MGVKFFTLFTRFFPSV | 82 |

TABLE 5-continued

Amino acid sequences of non-human SHLPs

| SHLP | Species | Amino acid sequence | SEQ ID (aa) |
|---|---|---|---|
| SHLP2 (9) | Chimp | MGVKFFTLFTRFFPSV | 83 |
| SHLP2 (11a) | Chimp | MGIKFFTLFTRFFPSVQRAVPLWTNS | 84 |
| SHLP2 (11b) | Chimp | MGIKFFTLFTSFFPSVQRAVPLWTNS | 85 |
| SHLP2 (M) | Orangutan | MGVVFFTLFLRFFPSV | 86 |
| SHLP2 (17) | Orangutan | MGVVFLLSFQGFS | 87 |
| SHLP4 (M) | Chimp | MLEVMFLVNRRGKICRVPFTFFNLSLWAC LCWVNSGGNNGLLVDCRY | 88 |
| SHLP4 (1) | Chimp | MLEVIFLVNRPSKICRVPFTFCNLSLEHA CVGLTE | 89 |
| SHLP4 (2b) | Chimp | MLEVVFLVNRQGICRFPFTFCNLSLEYD CVGLTVKITGYLLYRLLILGC | 90 |
| SHLP4 (4$_a$) | Chimp | MLEVMFLVNRQGKIC | 91 |
| SHLP4 (4$_b$) | Chimp | MLEVMFLVNRWGKICHVPLTFCNLSLEHT LVGLTV | 92 |
| SHLP4 (5) | Chimp | MLEVRFLVNRRGKICRVQLLFLTFPCGHA CVGLTVGVIMACW | 93 |
| SHLP4 (6) | Chimp | MLEVMFLVNRRGKICRVPFTFFNLSLWAC LCWVNSRSNTVSFFYIWLANYPSTIC | 94 |
| SHLP4 (7$_a$) | Chimp | MLEVMFLVNRRGKICRVPFTFFNLSL | 95 |
| SHLP4 (7$_b$) | Chimp | MLEVMFLVNRQGKICRVPFNFF | 96 |
| SHLP4 (8$_a$) | Chimp | MLEVMFLVNRQGKTCRVPFSFCNLSLEHT CVGLTV | 97 |
| SHLP4 (8$_b$) | Chimp | MLEVMFLVNRRDKICQVPFTFCNFSLEHT CVG | 98 |
| SHLP4 (8$_c$) | Chimp | MLEVMFLVNRQGMICRVLFTFCSPSLEHT CVRLKM | 99 |
| SHLP4 (9$_a$) | Chimp | MLEVMFLVNRRGKICRVPFTFFNLSLWAC LCWVNSGGNNGLLVDCRY | 100 |
| SHLP4 (9$_b$) | Chimp | MLEVMFLVNR | 101 |
| SHLP4 (10$_a$) | Chimp | MLQVMFLVNRRGKIG | 102 |
| SHLP4 (11$_a$) | Chimp | MLEVMFLVNRRGKICRVPFTFFNLSLWAC LCWVNSGGNSEAQVC | 103 |
| SHLP4 (11$_b$) | Chimp | MLEVMFLVNRRGKVCRVPFTFFNLSLWAC LCWVNSGGNNGLLVGCRY | 104 |
| SHLP4 (11$_c$) | Chimp | MLEVMFLVSRWGKICRVPFTFFNLSL | 105 |
| SHLP4 (17) | Chimp | MLEVMFLVNKLGKICRVPFTVCNLSLEHT CVGLTV | 106 |
| SHLP4 (20) | Chimp | MLEVMFLVNR | 107 |
| SHLP4 (X) | Chimp | MLEVMFLVNRRGKICGVPFTFCILSLEHT CVGLTV | 108 |
| SHLP4 (Ya) | Chimp | MLEVMFLVNRQGTIC | 109 |
| SHLP4 (Yb) | Chimp | MLEVMFLVNRQGTIC | 110 |
| SHLP4 (Yc) | Chimp | MLEVMFLVNRQGTIC | 111 |

TABLE 5-continued

Amino acid sequences of non-human SHLPs

| SHLP | Species | Amino acid sequence | SEQ ID (aa) |
|---|---|---|---|
| SHLP4 (M) | Orangutan | MLEVMFLVNRRGEICRVPFTFFNLSL | 112 |
| SHLP4 (2b$_a$) | Orangutan | MLEVMFLVNSQGMIC | 113 |
| SHLP4 (2b$_b$) | Orangutan | MLEMVFLVNRQGKICRFPFTFCNLSLEYDCVGLTVKITGCLLYHLLILDC | 114 |
| SHLP4 (4$_a$) | Orangutan | MLEVMFLVNRWGKICRVPLTFCNLSLEHTLVGLTV | 115 |
| SHLP4 (4$_b$) | Orangutan | MLEVMFLVNRWGKICRVPLTFCNLSLEHALVGLTV | 116 |
| SHLP4 (7$_a$) | Orangutan | MLEVMFLVNRQGKICQVPFTFFNLSYKHACVGLTVWVAPVCLKPATL | 117 |
| SHLP4 (7$_b$) | Orangutan | MLEVMFLVNRQGKICRVPFTLFNLSLEHACVGLTV | 118 |
| SHLP4 (8) | Orangutan | MLEVMFLVNRWDKICQVPFTFCNFSLEHTCVG | 119 |
| SHLP4 (9) | Orangutan | MLEVMFLVNRWGKICLVPFFVIFP | 120 |
| SHLP4 (10$_a$) | Orangutan | MLEVMFLVNSRGKIC | 121 |
| SHLP4 (10$_b$) | Orangutan | MLGVMFLVKRRSEMC | 122 |
| SHLP4 (11) | Orangutan | MLEVMFLVNRQGKIC | 123 |
| SHLP4 (12) | Orangutan | MLEVMFLVNRRGEICRVPFTFFNLS | 124 |
| SHLP4 (17$_a$) | Orangutan | MLEVMFLVNRRGEICRVPFTFFNLSL | 125 |
| SHLP4 (17$_b$) | Orangutan | MLEVMFLVNKLGKICRVPFTVCNLSLEHTCVGLTV | 126 |
| SHLP4 (17$_c$) | Orangutan | MLEVMFLVNRRDKICQVPFTFCNLSLEHTCVGLTV | 127 |
| SHLP4 (20) | Orangutan | MLEVMFLVNRRGKIC | 128 |
| SHLP4 (X) | Orangutan | MLEVMFLVNRWGKICGVPFTFCILSLEHTCVGLTV | 129 |
| SHLP4 (1$_a$) | Rhesus | MLEVMFLVNRRGLSLPSSFYFF | 130 |
| SHLP4 (1$_b$) | Rhesus | MLEVIFLVNRPSKICRAPFTFCNLSLAHACVGLTE | 131 |
| SHLP4 (3) | Rhesus | MLEVMFLVNRQGKIC | 132 |
| SHLP4 (5$_a$) | Rhesus | MLEVMFLVNRRGLSLPSSFYFF | 133 |
| SHLP4 (5$_b$) | Rhesus | MLEVMFLVNRQGKIC | 134 |
| SHLP4 (5$_c$) | Rhesus | MLEVMFLVNRWGKICHVPFTFLQSSLEDT | 135 |
| SHLP4 (6$_a$) | Rhesus | MLEVMFLVNRRGLSLPSSFYFF | 136 |
| SHLP4 (6$_b$) | Rhesus | MLEVMFLVNRWG | 137 |
| SHLP4 (6$_c$) | Rhesus | MLEVMFLVNRRGLSLPSSFYLF | 138 |
| SHLP4 (8$_a$) | Rhesus | MLEVMFLVNRRG | 139 |
| SHLP4 (8$_b$) | Rhesus | MLEVMFLVNRWDKICRVPFSFCNLSLEHACVGLAV | 140 |
| SHLP4 (8$_c$) | Rhesus | MLEVMFLVSRWDKICQVPFTFCYLSLEHTCVG | 141 |
| SHLP4 (9$_a$) | Rhesus | MLGVMFLVNRRGEICRVSFTFCNLSLEHA | 142 |

TABLE 5-continued

Amino acid sequences of non-human SHLPs

| SHLP | Species | Amino acid sequence | SEQ ID (aa) |
|---|---|---|---|
| SHLP4 ($9_b$) | Rhesus | MLEVMFLVNRQCKIC | 143 |
| SHLP4 ($9_c$) | Rhesus | MLEVMISVNRRLKFAEFLLLFLTFP | 144 |
| SHLP4 ($10_a$) | Rhesus | MLEVMFLVNRPGKICQVPFTFFNLSLEHT CVGITV | 145 |
| SHLP4 ($10_b$) | Rhesus | MLDVMFLVNRQGRICQVPFTFCNVSLEHA CVGLTVQIIGVYYIIY | 146 |
| SHLP4 (13) | Rhesus | MLEVMFLVNRQGMICQIPFTFCNISLEHT CVGLIV | 147 |
| SHLP4 (14) | Rhesus | MLEVMFLVNRQSKIG | 148 |
| SHLP4 (15) | Rhesus | MLEVMFLVNRQG | 149 |
| SHLP4 (16) | Rhesus | MLEVMFLVNRWGLSLPSSFYFF | 150 |
| SHLP4 (18) | Rhesus | MLVVMFLVNRRG | 151 |
| SHLP4 (20) | Rhesus | MLEVMFLVNRWGKISEFLILFVIFP | 152 |
| SHLP4 (X) | Rhesus | MLEVMFLVNRRGKICQVPFTFCVLSLQHA CVGLTV | 153 |
| SHLP4 (M) | Mouse | MLEVMFLVNRRGSCLPSSFYLFGSFL | 154 |
| SHLP4 (M) | Rat | MLEEMFLVNRRGSCLPSSFTFLNFP | 155 |
| SHLP4 (M, $701_{a-b}$, $953_{a-b}$, 1260, 1738, 1772, 1912, 2039, 2262, 2354, 2542, 2574, 2887) | Guinea Pig | MLEVMFLVNRRDLCLPSSFCFVLSFLSST PVSG | |
| SHLP4 (13) | Guinea Pig | MLEVMFLVNRQDLCLPSSFCFVSSFLSST PVSD | 156 |
| SHLP4 (35) | Guinea Pig | MLEVMFLVIRRDLCLPSSFCFVSSFLSST PVSG | 157 |
| SHLP4 (86) | Guinea Pig | MLEVMFLVNRRDLCLPCSFCLFFFFVFPE | 158 |
| SHLP4 (141) | Guinea Pig | MLEVMFLVNRQDLCLPSSFCFLSFPSSTP MSD | 159 |
| SHLP4 (243) | Guinea Pig | MLEVVFLVKQAGFVFAEFLLLCFVFPE | 160 |
| SHLP4 (701) | Guinea Pig | MLEVMFLVTGGICVCRVPFALFCLS | 161 |
| SHLP4 (18811, 18812, 30562, $112167_{a-e}$) | Cat | MLEVMFLVNRRGLCLPSSFYFF | 162 |
| SHLP4 (37160) | Cat | MLEVMFLVNRRGLHLPSSFHFL | 163 |
| SHLP4 (44282, 93736) | Cat | MLEVILLVNRWGLCSLSSFYFVSSFLDCL SVLGQQLVWY | 164 |
| SHLP4 (112168) | Cat | MLEVMFSVNRRDLCLPSSFYFF | 165 |
| SHLP4 (172769) | Cat | MLEVMFLVNRRGLCLPSSFYFF | 166 |

TABLE 5-continued

Amino acid sequences of non-human SHLPs

| SHLP | Species | Amino acid sequence | SEQ ID (aa) |
|---|---|---|---|
| SHLP4 (M) | Dog | MLPLHGQDTAAVKQVSPGRQCLQY | |
| SHLP4 (M) | Horse | MLEVMFLVNRRGLCLPSSFYFF | 167 |
| SHLP4 (1) | Horse | MLEVMFSVNMRGLCLPSSFYFF | 168 |
| SHLP4 (8) | Horse | MLEVMFLVNRRSLCLLSSFYFFKSFLRVH ACVGLTV | 169 |
| SHLP4 (M) | Cow | MLPLHGQDTAAVKQLSLGRQCLQYWECWR | |
| SHLP4 (M) | Platypus | MLEAMFLVNRRNPSLPSSFYSF | 170 |
| SHLP4 (M) | Fugu | ....MFLVNRRGFEFAEFLLFLLVFPIWH TSVGVTEKC | 171 |
| SHLP4 (M) | Stickleback | IQEAMFLVNRRGFMCLPSSFSFF | 172 |
| SHLP4 (M) | Madeka | ISSLQEAMFLVNRRGLVYLPSSFSSFLSF LKSTPV | 173 |
| SHLP4 (M) | Lamprey | ILDFYLEVMFLVNRRGMCLPSSFLSFISSILC SSVGLTVISSCFSCCCLCF | 174 |
| SHLP5 (M) | Chimp | MYCSEVGLCSEVAPTEIFNAGLIV | 175 |
| SHLP5 (M) | Orangutan | MCFSEVGLCSEVAPTEIFSAGLVI | 176 |
| SHLP5 (M) | Chicken | .VGLEDFFFSKVAPTEKCRPGVYVWVDPV GLCKVVRWS | 177 |
| SHLP6 (M) | Chimp | MLDQDIPMVQPLLKVRLFND | 178 |
| SHLP6 (1) | Chimp | MLDQDIPMVQPLLKVRLFND | 179 |
| SHLP6 (4a) | Chimp | MLDQDMLMVQPLSKVRLFNDCTS | 180 |
| SHLP6 (4b) | Chimp | MLDQDILMVQLLLRVCFFSD | 181 |
| SHLP6 (5) | Chimp | MLDQDIPMVQPLLKVRLFND | 182 |
| SHLP6 (7) | Chimp | MLDQDILMVQPLLKVRLFND | 183 |
| SHLP6 (9) | Chimp | MLDQDIPMVQPLLKVRLFND | 184 |
| SHLP6 (17) | Chimp | MLDQDILMVQPVLRVRLFND | 185 |
| SHLP6 (M) | Orangutan | MLDQDILMVQPLLKVRLFND | 186 |
| SHLP6 (4a) | Orangutan | MLDQDILMV | 187 |
| SHLP6 (4b) | Orangutan | MLDQDILMVQPLSKFHLFNNCTS | 188 |
| SHLP6 (4c) | Orangutan | MLDHVILMV | 189 |
| SHLP6 (9) | Orangutan | MLDQDILMV | 190 |
| SHLP6 (11) | Orangutan | MLDQDILMV | 191 |
| SHLP6 (13a) | Orangutan | MLDQDIPMVQPLLKVRLFND | 192 |
| SHLP6 (13b) | Orangutan | MLDQDILMV | 193 |
| SHLP6 (14) | Orangutan | MLDQDILMV | 194 |
| SHLP6 (17a) | Orangutan | MLDQDILMVQPLLKVRLFND | 195 |
| SHLP6 (17b) | Orangutan | MLDQDILMVQPLLRVRLFND | 196 |

TABLE 5-continued

Amino acid sequences of non-human SHLPs

| SHLP | Species | Amino acid sequence | SEQ ID (aa) |
| --- | --- | --- | --- |
| SHLP6 (17c) | Orangutan | MLDQDIPRVQLLLKFRLFND | 197 |
| SHLP6 (1, 2, 4, 5, 6, 13) | Rhesus | MLDQDILMVQQLSRVRLFND | 198 |
| SHLP6 (5) | Rhesus | MLHQDILMV | 199 |
| SHLP6 (8) | Rhesus | MLDQDILMVQQLSRVLLFNN | 200 |
| SHLP6 (18) | Rhesus | MLDQDILMV | 201 |
| SHLP6 (M) | Mouse | MLDQDIPMV | 202 |
| SHLP6 (M) | Rat | MLDQDIPMVQKLLMVRLFND | 203 |
| SHLP6 (unknown) | Opossum | MLDQDTPMVQPLLKVRLFND | 204 |
| SHLP6 (unknown) | Platypus | MLDQDIQMVQPLLMVRLFND | 205 |
| SHLP6 (M, 35, 48, 701$_{a-c}$, 953$_{a-b}$, 1260, 1486, 1738, 1772, 1912, 2039, 2262, 2354, 2574, 2887) | Guinea pig | MLDQDILMVQQLLRVRLFND | 206 |
| SHLP6 (13) | Guinea Pig | MLDLVILMVQPLSRVRLFND | 207 |
| SHLP6 (79) | Guinea Pig | MLDQDVLMGQPLLSVRLFND | 208 |
| SHLP6 (86) | Guinea Pig | MLDQDILMVRRLLRVHLFND | 209 |
| SHLP6 (243) | Guinea Pig | MLDQDILMVQQLLRVRLFND | 210 |
| SHLP6 (18811, 18812) | Cat | MLDQDIPMVQQLSKVRLFND | 211 |
| SHLP6 (30562, 66390, 112167$_{a-e}$) | Cat | MLDQDIPIVQQLSKVCLFND | 212 |
| SHLP6 (37160) | Cat | MLDQDIPIVQQLSKVCLFND | 213 |
| SHLP6 (63432) | Cat | MLDQDIPMVQQLSKFRLFNNSSPT | 214 |
| SHLP6 (92191) | Cat | MLDQDIPMVQQLAKVRLLDD | 215 |
| SHLP6 (M) | Dog | MLDQDILMVQQLLRVRLFND | 216 |
| SHLP6 (X) | Dog | MLDQDILMVQQLLRVSLFNN | 217 |
| SHLP6 (M) | Horse | MLDQDILMVQPLLRVRLFND | 218 |
| SHLP6 (1) | Horse | MLDQDILMVQPLLRVCLFND | 219 |
| SHLP6 (M) | Cow | MLDQDILMVQPLSKVRLFND | 220 |
| SHLP6 (M) | Chicken | MLDQDNLMVQPLLRVRLFND | 221 |

TABLE 5-continued

Amino acid sequences of non-human SHLPs

| SHLP | Species | Amino acid sequence | SEQ ID (aa) |
|---|---|---|---|
| SHLP6 (M) | Zebra Finch | MLDQDILVVQPLLRVRLFND | 222 |
| SHLP6 (2) | Zebra Finch | MLDQDILVVQPLLRVRLFNDLQSYVI | 223 |
| SHLP6 (927$_{a-b}$, 2224$_{a-b}$) | Lizard | MLDQDTQMVQPLLKVRLFND | 224 |
| SHLP6 (18215) | *X. tropicalis* | MLDQGIPVVQPLLKVRLFND | 225 |
| SHLP6 (M) | Zebrafish | MLDQDILMVQPLLRVRLFND | 226 |
| SHLP6 (unknown) | Tetradon | MLDQDILMVQPLLRVRLFND | 227 |
| SHLP6 (M) | Fugu | MLDQDILMVQPLLKVRLFND | 228 |
| SHLP6 (M) | Stickleback | MLDQDILMVQPLLRVRLFND | 229 |
| SHLP6 (M) | Medaka | MLDQDILMVQPLLRVCLFNN | 230 |
| SHLP6 (M) | Lamprey | MLDRGTPMAQKLLKVRLFND | 231 |

TABLE 6

Nucleic acid sequences encoding non-human SHLPs

| SHLP | Species | Nucleic acid sequence | SEQ ID (nt) |
|---|---|---|---|
| SHLP1 (M) | Chimp | TTACCCCGCCTGTTTACCAAAAACATCACC TCTAGCATT<u>A</u>CCAGTATTAGAGGCACCGCC TGCCC<u>G</u>GTGACA<u>T</u>AT | 232 |
| SHLP1 (M) | Orangutan | T<u>C</u>ACCCCGCCTGTTTACCAAAAACATCACC TCTAGCATT<u>A</u>CCAGTATTAGAGGCACCGCC TGCCC<u>G</u>GTGACACAT | 233 |
| SHLP1 (5) | Rhesus | TTACCCC<u>A</u>T<u>C</u>TGTTTACCAAAAACATCACC TCTAGCATT<u>A</u>CCAGTAT<u>G</u>AGAG<u>T</u>CAC<u>T</u>GCC TGCCCAGCACAT | 3 |
| SHLP1 (8) | Rhesus | T<u>A</u>ACCCCGCCT<u>A</u>TTTACCAAAAACATCACC TCTAGCATT<u>A</u>CCAGTATTAGAGGCACCGCC TGCCCAGTGACACA | 4 |
| SHLP1 (16) | Rhesus | CCGCCTGTTT ACCAAAAACA TCACCTCTAG CATT<u>GC</u>TAGT ATTAGAGGCA C<u>T</u>GCCTGCCC AGTGACACAT | 5 |
| SHLP1 (18) | Rhesus | T<u>A</u>ACCCCGCC TGTTTACCAA AAACATCACC <u>A</u>CTAGCATT<u>A</u> CCAGTATTAG AGGCACCGCC TGCCC<u>A</u>T<u>T</u>GA CACAT | 6 |
| SHLP1 (149667) | Cat | ACCCCGCCTGTTTACCAA<u>T</u>AACATCACCTC TAGCATT<u>TTTT</u>AGTATTAAGGCAC<u>G</u>GCCTGC CCAG<u>GG</u>GACA<u>T</u> | 234 |
| SHLP2 (M) | Chimp | TTAACTGTTAGTCCAAAGAGGAACAGCTCT TT<u>A</u>GACACTAGGAAAAAACCTTGTA<u>A</u>AGAG AGTAAAAAATTTAACACCCAT | 235 |
| SHLP2 (9) | Chimp | TTAACTGTTAGTCCAAAGAGGAACAGCTCT TT<u>A</u>GACACTAGGAAAAAACCTTGTA<u>A</u>AGAG AGTAAAAAATTTAACACCCA T | 236 |

TABLE 6-continued

Nucleic acid sequences encoding non-human SHLPs

| SHLP | Species | Nucleic acid sequence | SEQ ID (nt) |
|---|---|---|---|
| SHLP2 (11a) | Chimp | TTAACTGTTAGTCCAAAGAGGAACAGCTCT TTGGACACTAGGAAAAAACCTTGTAAAGAG AGTAAAAAATTTAATACCCA T | 237 |
| SHLP2 (11b) | Chimp | TTAACTGTTAGTCCAAAGAGGAACAGCTCT TTGGACACTAGGAAAAAAACTTGTAAAGAG AGTAAAAAATTTAATACCCAT | 238 |
| SHLP2 (M) | Orangutan | TAGTCTAAAGAGGAACAGCTCTTTAGACAC TAGGAAAAAACCTTAAAAAGAGAGTAAAA AACACAACACCCAT | 239 |
| SHLP2 (17) | Orangutan | TAGTCTAAAG AGGAACAGCTCTTTAGACAC TAGGAAAAACCTTGAAAAGAGAGT(*)AAAA ACACAACACCCAT | 240 |
| SHLP4 (M) | Chimp | AAGGAAAGGTTAAAAAAAGTAAAAGGAAC TCGGCAAATCTTACCCCGCCTGTTTACCAA A AACATCACCTCTAGCAT | 241 |
| SHLP4 (1) | Chimp | TAAGGAAAGATTACAAAAAGTAAAAGGAA CTCTGCAAATCTTACTCGGTCTGTTTACCAA AAATATCACCTCTAGCAT | 242 |
| SHLP4 (2b) | Chimp | TAAGGAAAGATTACAAAAAGTAAAAGGAA ATCGGCAAATCTTACCTTGCCTGTTTACCAA AAACACCACCTCTAGCAT | 243 |
| SHLP4 (4$_a$) | Chimp | TAAGGAAAGTTTACAACAAGTAAAAGGAA CTCAGCAAATCTTACCCTGCCTGTTTACCAA AAACATCACCTCTAGCAT | 244 |
| SHLP4 (4$_b$) | Chimp | TAAGGAAAGATTGCAAAAAGTAAGAGGAA CATGACAAATCTTACCCCACCTGTTTACCA AAAACATCACCTCTAGCAT | 245 |
| SHLP4 (5) | Chimp | AAGGAAAGGT TAAAAAAAGT AATTGAACTC GGCAAATCTT ACCCCGCCTG TTTACCAAAA ACCTCACCTC TAGCAT | 246 |
| SHLP4 (6) | Chimp | CATAAGGAAAGGTTAAAAAAAGTAAAAGG AACTCGGCAAATCTTACCCCGCCTGTTTACC AAAAACATCACCTCTAGCAT | 247 |
| SHLP4 (7$_a$) | Chimp | TTATAAGGAAAGGTTAAAAAAAGTAAAAG GAACTCGGCAAATCTTACCCCGCCTGTTTA CCAAAAACATCACCTCTAGCA T | 248 |
| SHLP4 (7$_b$) | Chimp | TAAGGAAAGGTTAAAAAAAATTAAAAGGA ACTCGGCAAATTTTACCCTGCCTGTTTACCA AAACATCACCTCTAGCAT | 249 |
| SHLP4 (8$_a$) | Chimp | TAAGGAAAGATTACAAAAACTAAAAGGAA CTCTGCAAGTCTTACCCTGCCTGTTTACCAA AAACATCACCTCTAGCAT | 250 |
| SHLP4 (8$_b$) | Chimp | TAAGGAAAAATTACAAAAAGTGAAAGGAA CTTGGCAAATCTTGTCCCGCCTATTTACCAA AAACATCACCTCTAGCAT | 251 |
| SHLP4 (8$_c$) | Chimp | TAAGGAAGGACTGCAAAAAGTAAAAGAAA CTCGACAAATCATACCCTGCCTGTTTACCA AAAACATCACCTCTAGCAT | 252 |
| SHLP4 (9$_a$) | Chimp | AAGGAAAGGTTAAAAAAAGTAAAAGGAAC TCGGCAAATCTTACCCCGCCTGTTTACCAA A AACATCACCT CTAGCAT | 253 |
| SHLP4 (9$_b$) | Chimp | TAAGGAAATATTACAAAAAGTAAAAGGAA CTCGGCAAATCTTACCCTACCTGTTTACCAA AAACATCACCTCTAGCAT | 254 |

TABLE 6-continued

Nucleic acid sequences encoding non-human SHLPs

| SHLP | Species | Nucleic acid sequence | SEQ ID (nt) |
| --- | --- | --- | --- |
| SHLP4 (10$_a$) | Chimp | TAAGGAAAGATTACAAAAAGTAAAAGGAA TTCAGCCAATCTTACCCCGCCTGTTTACCAA AAACATCACCTGTAGCAT | 255 |
| SHLP4 (11$_a$) | Chimp | AAGGAAAGGTTAAAAAAAGTAAAAGGAAC TCGGCAAATCTTACCCCGCCTGTTTACCAA A AACATCACCTCTAGCAT | 256 |
| SHLP4 (11$_b$) | Chimp | AAGGAAAGGTTAAAAAAAGTAAAAGGAAC TCGGCAAACCTTACCCCGCCTGTTTACCAA AAACATCACCTCTAGCAT | 257 |
| SHLP4 (11$_c$) | Chimp | AAGGAAAGGTTAAAAAAAGTAAAAGGAAC TCGGCAAATCTTACCCCACCTGCTTACCAA AAACATCACCTCTAGCAT | 258 |
| SHLP4 (17) | Chimp | TAAGGAAAGATTACAAACAGTAAAAGGAA CTCGGCAAATCTTACCCAGCTTGTTTACCAA AAACATCACCTCTAGCAT | 259 |
| SHLP4 (20) | Chimp | TAAGGAAATATTACAAAAAGTAAAAGGAA CTCGGCAAATCTTACCCTACCTGTTTACCAA AAACATCACCTCTAGCAT | 260 |
| SHLP4 (X) | Chimp | TAAGGAAAGAATACAAAAAGTAAAAGGAA CTCCGCAAATTTTACCCCGCCTGTTTACCAA AAACATCACCTCTAGCAT | 261 |
| SHLP4 (Ya) | Chimp | TAAGGAAAGATTACAAAAACTAAAAGGAA CTCAGCAAATCGTACCCTGCCTGTTTACCA AAAACATCACCTCTAGCAT | 262 |
| SHLP4 (Yb) | Chimp | TAAGGAAAGATTACAAAAACTAAAAGGAA CTCAGCAAATCGTACCCTGCCTGTTTACCA A AAACATCACC TCTAGCAT | 263 |
| SHLP4 (Yc) | Chimp | TAAGGAAAGATTACAAAAACTAAAAGGAA CTCAGCAAATCGTACCCTGCCTGTTTACCA AAAACATCACC TCTAGCAT | 264 |
| SHLP4 (M) | Orangutan | ATAAGGAAAGGTTAAAAAAAGTAAAAGGA ACTCGGCAAATCTCACCCCGCCTGTTTACC AAAAACATCACCTCTAGCAT | 265 |
| SHLP4 (2b$_a$) | Orangutan | TAAGGAAAGATTACAAAAAGTAAAAGGAA CTCAGCAAATCATACCCTGACTGTTTACCA AAAACATCACCTCTAGCAT | 266 |
| SHLP4 (2b$_b$) | Orangutan | TAAGGAAAGATTACAAAAAGTAAAAGGAA ATCGGCAAATCTTACCTTGCCTGTTTACCAA AAACACCATCTCTAGCAT | 267 |
| SHLP4 (4$_a$) | Orangutan | TAAGGAAAGATTGCAAAAAGTAAGAGGAA CACGACAAATCTTACCCCACCTGTTTACCA AAAACATCACCTCTAGCAT | 268 |
| SHLP4 (4$_b$) | Orangutan | TAAGGAAAGATTGCAAAAAGTAAGAGGAA CACGACAAATCTTACCCCACCTGTTTACCA AGAACATCACCTCTAGCAT | 269 |
| SHLP4 (7$_a$) | Orangutan | AGGAAAGGTTAAAAAAAGTAAAGGAACT TGGCAAATCTTACCCTGCCTGTTTACCAAA AACATCACCTCTAGCAT | 270 |
| SHLP4 (7$_b$) | Orangutan | TAAGGAAAGGTTAAAAAGAGTAAAAGGAA CTCGGCAAATTTTACCCTGCCTGTTTACCAA AAACATCACCTCTAGCAT | 271 |
| SHLP4 (8) | Orangutan | TAAGGAAAATTACAAAAAGTAAAAGGAA CTTGGCAAATCTTATCCCACCTATTTACCAA AAACATCACCTCTAGCAT | 272 |

TABLE 6-continued

Nucleic acid sequences encoding non-human SHLPs

| SHLP | Species | Nucleic acid sequence | SEQ ID (nt) |
|---|---|---|---|
| SHLP4 (9) | Orangutan | TAAGGAAATATTACAAAAAAAGGAACTAGGCAAATCTTACCCCACCTGTTTACCAAAAACATCACCTCTAGCAT | 273 |
| SHLP4 (10a) | Orangutan | TAAGGAAAGATTACAAAAAGTAAAGGAATTCAGCAAATCTTACCCCGACTGTTTACCAAAAACATCACCTCTAGCAT | 274 |
| SHLP4 (10b) | Orangutan | TAAGGAAAGATTACAAAAAGTAAAGGAACTCAGCACATTTCACTCCGTCTCTTTACCAAAAACATCACCCCTAGCAT | 275 |
| SHLP4 (11) | Orangutan | AAGGAAAGGTTACAAAAAGTAAAGGAACTCAGCAAATCTTACCCTGCCTGTTTACCAAAACATCACCTCTAGCAT | 276 |
| SHLP4 (12) | Orangutan | AGGAAAGGTTAAAAAAAGTAAAAGGAACTCGGCAAATCTCACCCCGCCTGTTTACCAAAAACATCACCTCTAGCAT | 277 |
| SHLP4 (17a) | Orangutan | ATAAGGAAAGGTTAAAAAAAGTAAAAGGAACTCGGCAAATCTCACCCCGCCTGTTTACCAAAAACATCACCTCTAGCAT | 278 |
| SHLP4 (17b) | Orangutan | TAAGGAAAGATTACAAACAGTAAAAGGAACTCGGCAAATCTTACCCAGCTTGTTTACCAAAAACATCACCTCTAGCAT | 279 |
| SHLP4 (17c) | Orangutan | TAAGGAAAGATTACAAAAAGTAAAGGAACTTGGCAAATCTTATCCCGCCTATTTACCAAAAACATCACCTCTAGCAT | 280 |
| SHLP4 (20) | Orangutan | TAAGGAAACATTACAAAAAGAAAAGGAACTCAGCAAATCTTACCCCGCCTGTTTACCAAAAACATCACCTCTAGCAT | 281 |
| SHLP4 (X) | Orangutan | TAAGGAAAGAATACAAAAAGTAAAGGAACTCCGCAAATTTTACCCCACCTGTTTACCAAAAACATCACCTCTAGCAT | 282 |
| SHLP4 (1a) | Rhesus | GGAAAGGTTAAAAAAAGTAAAAGGAACTTGGCAAACTCAAACCCCGCCTGTTTACCAAAAACATCACCTCTAGCAT | 283 |
| SHLP4 (1b) | Rhesus | TAAGGAAAGATTACAAAAAGTAAAGGAGCTCGGCAAATCTTACTCGGCCTGTTTACCAAAAATATCACCTCTAGCAT | 284 |
| SHLP4 (3) | Rhesus | TAAGGAAAGGTTAAAAAAAGGAAAAGGAACTCAGCAAATTTTACCCTGCCTGTTTACCAAAAACATCACCTCTAGCAT | 285 |
| SHLP4 (5a) | Rhesus | TAAGGAAAGGTTAAAAAAAGTAAAGGAACTCGGCAAACTTAACCCCCGCCTGTTTACCAAAAACATCACCTCTAGCAT | 286 |
| SHLP4 (5b) | Rhesus | TAAGGAAAGTTTACAAAAAGTGAAGGAACTCAGCAAATCTTACCCTGCCTGTTTACCAAAAACATCACCTCTAGCAT | 287 |
| SHLP4 (5c) | Rhesus | TAAGGAAGACTGCAAAAAAGTAAAAGGAACATGGCAAATCTTACCCCATCTGTTTACCAAAAACATCACCTCTAGCAT | 288 |
| SHLP4 (6a) | Rhesus | TAAGGAAAGGTTAAAAAAAGTAAAGGAACTCGGCAAACTCAAACCCCGCCTGTTTACCAAAAACATCACCTCTAGCAT | 289 |
| SHLP4 (6b) | Rhesus | TCTTAAGGAAAGGTTAAAAAAAGTAAAAGGAACTCGGCAAATCTAACCCCACCTGTTTACCAAAAACATCACCTCCAGC | 290 |

TABLE 6-continued

Nucleic acid sequences encoding non-human SHLPs

| SHLP | Species | Nucleic acid sequence | SEQ ID (nt) |
| --- | --- | --- | --- |
| SHLP4 (6c) | Rhesus | TAAGGAAAGGTTAAAAAAGGTAAAAGGAA CTCGGCAAACTCAAACCCCGCCTGTTTACC AAAAACATCACCTCTAGCAT | 291 |
| SHLP4 (8a) | Rhesus | TAAGGAAAGGTTAAAAAAAGTAAAAGGAA CTCGGCAAACTTAACCCCGCCTATTTACCA AAAACATCACCTCTAGCAT | 292 |
| SHLP4 (8b) | Rhesus | TAAGGAAAGATTACAAAAACTAAAAGGAA CTCTGCAAATCTTATCCCACCTGTTTACCAA AAACATCACCTCTAGCAT | 293 |
| SHLP4 (8c) | Rhesus | TAAGGAAAGATAACAAAAGGTAAAAGGAA CTTGGCAAATCTTATCCCACCTACTTACCAA AAACATCACCTCTAGCAT | 294 |
| SHLP4 (9a) | Rhesus | TAAGGAAAGGTTACAAAAAGTAAAGAAA CTCGGCAAATTTCACCCCGTCTGTTTACCAA AAACATCACCCCTAGCAT | 295 |
| SHLP4 (9b) | Rhesus | TAAGGAAAGATTACAAAAAGTAAAAGGAA TTCAGCAAATCTTACACTGCCTGTTTACCAA AAACATCACCTCTAGCAT | 296 |
| SHLP4 (9c) | Rhesus | TAAGGAAAGGTTAAAAAAAGTAAAAGGAA CTCGGCAAATTTTAGCCTCCTGTTTACCGAA ATCATCACCTCTAGCAT | 297 |
| SHLP4 (10a) | Rhesus | TAAGGAAAGGTTAAAAAAAGTAAAAGGAA CTTGGCAAATTTTACCCGGCCTGTTTACCAG AAACATCACCTCTAGCAT | 298 |
| SHLP4 (10b) | Rhesus | TAAGGAAACATTACAAAAAGTAAAAGGAA CTTGGCAAATCCTACCCTGCCTGTTTACCAA AAACATCACGTCTAGCAT | 299 |
| SHLP4 (13a) | Rhesus | TAAGGAAATATTACAAAAAGTAAAAGGAA TTTGGCAAATCATACCCTGCCTGTTTACCAA AAACATCACCTCTAGCAT | 300 |
| SHLP4 (14) | Rhesus | AAGGAAAGTTTACAAAAAGTAAAAGGAAC TCAGCCAATCTTACTCTGCCTGTTTACCAAA AACATCACCTCTAGCAT | 301 |
| SHLP4 (15) | Rhesus | TAAGGAAAGATTACAATAAGTAAAAGGAA CTCAGCAAATCTAACCCTGCCTGTTTACCA AAAACATCACCTCTAGCAT | 302 |
| SHLP4 (18) | Rhesus | TAAGGAAAGGTTAAAAAAAGTAAAAGGAA CTCAACAAACTTAACCCCGCCTGTTTACCA AAAACATCACCACTAGCAT | 303 |
| SHLP4 (16) | Rhesus | TCTTAAGGAAAGGTTAAAAAAAGTAAAAG GAACTCGGCAAACTTAAACCCCACCTGTTT ACCAAAAACATCACCTCTAGCAT | 304 |
| SHLP4 (20) | Rhesus | TAAGGAAAGATTACAAAAAGTATAAGGAA CTCGGAAATCTTACCCCACCTGTTTACCAA AAACATCACCTCTAGCAT | 305 |
| SHLP4 (X) | Rhesus | TAAGGAAAGAACACAAAAGTAAAAGGAA CTTGGCAAATTTTACCCCGCCTGTTTACCAA AAACATCACCTCTAGCAT | 306 |
| SHLP4 (M) | Mouse | AAGGAAAGATCCAAAAAGATAAAAGGAAC TCGGCAAACAAGAACCCCGCCTGTTTACCA AAAACATCACCTCTAGCAT | 307 |
| SHLP4 (M) | Rat | TAAGGAAAGTTTAAAAAAGTAAAGGAACT CGGCAAACACGAACCCCGCCTGTTTACCAA AAACATCTCCTCTAGCAT | 308 |
| SHLP4 (M, 701a-b, 953a-b, | Guinea Pig | GGAAAGACAAAACAAAGCAAAGGAACTC GGCAAACACAAATCCCGCCTGTTTACCAAA | 309 |

TABLE 6-continued

Nucleic acid sequences encoding non-human SHLPs

| SHLP | Species | Nucleic acid sequence | SEQ ID (nt) |
|---|---|---|---|
| 1260, 1738, 1772, 1912, 2039, 2262, 2354, 2542, 2574, 2887) | | AACATCACCTCTAGCAT | |
| SHLP4 (13) | Guinea Pig | AGGAAAGACGAAACAAAGCAAAGGAACT CGGCAAACATAAATCCTGCCTGTTTACCAA AAACATCACCTCTAGCAT | 310 |
| SHLP4 (35) | Guinea Pig | AGGAAAGATGAAACAAAGCAAAGGAACT CGGCAAACACAAATCCCGCCTGATAACCAA AAACATCACCTCTAGCAT | 311 |
| SHLP4 (86) | Guinea Pig | AGGAAAGACAAAAAAAAAAAAAAGGCAAA AGGAACACGGCAAACACAAATCCCGCCTGT TTACCAAAAACATCACCTCTAGCAT | 312 |
| SHLP4 (141) | Guinea Pig | GGAAAGACAAAAAGCAAAGGAACTCGGT AAACATAAATCCTGCCTGTTTACCAAAAAC ATCACCTCTAGCAT | 313 |
| SHLP4 (243) | Guinea Pig | GGAAAGACAAAACAAAGCAAAGGAACTC GGCAAACACAAATCCCGCCTGTTTAACCAA AAACACCACCTCTAGCAT | 314 |
| SHLP4 (701) | Guinea Pig | AGGAAAGACAAAACAAAGCAAAGGAACT CGGCAAACACAAATCCCGCCTGTTACCAAA AACATCACCTCTAGCAT | 315 |
| SHLP4 (18811, 18812, 30562, 112167ₐ₋ₑ) | Cat | GGAAAGATTAAAAGAAGTAAAAGGAACTC GGCAAACACAAGCCCCGCCTGTTTACCAAA AACATCACCTCTAGCAT | 316 |
| SHLP4 (37160) | Cat | TAAGGAAAGATTAAAGGAAGTGAAAGGAA CTTGGCAAATGCAAACCCCGCCTGTTTACC AAAAACATCACCTCTAGCAT | 317 |
| SHLP4 (44282, 93736) | Cat | AAGGAAAGATGAAACAAAGTAAAAGGAAC TCAGCGAACACAAACCCCACCTGTTTACCA GTAAAATCACCTCTAGCAT | 318 |
| SHLP4 (112168) | Cat | ATAAGGAAAGATTAAAAGAAGTAAAAGGA ACTCGGCAAACACAAGTCCCGCCTGTTTAC CGAAAACATCACCTCTAGCAT | 319 |
| SHLP4 (172769) | Cat | GGAAAGATTAAAAGAAGTAAAAGGAACTC GGCAAACACAAGCCTCGCCTGTTTACCAAA AACATCACCTCTAACAT | 320 |
| SHLP4 (M) | Horse | ATAAGGAAAGATTAAAAGAAGTAAAAGGA ACTCGGCAAACACAAACCCCGCCTGTTTAC CAAAAACATCACCTCTAGCAT | 321 |
| SHLP4 (1) | Horse | CATAAGGAAAGATTAAAAGAAGTAAAAGG AACTCGGCAAACACAAACCCCGCATGTTTA CCGAAAACATCACCTCTAGCAT | 322 |
| SHLP4 (8) | Horse | TAAGGAAAGATTTAAAAAAGTAAAAGGAA CTCAGCAAACACAAACTCCGCCTGTTTACC AAAAACATCACCTCTAGCAT | 323 |
| SHLP4 (M) | Platypus | TAAGGAAAGATTAAAAGGAGTAAAAGGAA CTCGGCAAACTAGGATTTCGCCTGTTTACC AAAAACATCGCCTCTAGCAT | 324 |
| SHLP6 (M) | Chimp | ATGTTGGATCAGGACATCCCGATGGTGCAG CCGCTATTAAAGGTTCGTTTGTTCAACGATT AA | 325 |

TABLE 6-continued

Nucleic acid sequences encoding non-human SHLPs

| SHLP | Species | Nucleic acid sequence | SEQ ID (nt) |
|---|---|---|---|
| SHLP6 (1) | Chimp | ATGTTGGATCAGGACATCCCGATGGTGCAG CCGCTATTAAAGGTTCGTTTGTTCAACGATT AA | 326 |
| SHLP6 (4a) | Chimp | ATGTTGGATCAGGACATGCTGATGGTGCAG CCGCTATCAAAGGTTCGTTTGTTCAACGATT | 327 |
| SHLP6 (4b) | Chimp | ATGTTGGATCAGGACATCCTAATGGTGCAG CTGCTATTAAGGGTTTGTTTCTTCAGTGATT AA | 328 |
| SHLP6 (5) | Chimp | ATGTTGGATCAGGACATCCCGATGGTGCAG CCGCTATTAAAGGTTCGTTTGTTCAACGATT AA | 329 |
| SHLP6 (7) | Chimp | ATGTTGGATCAGGACATCCTGATGGTGCAG CCGCTATTAAAGGTTCGTTTGTTCAACGATT AA | 330 |
| SHLP6 (9) | Chimp | ATGTTGGATCAGGACATCCCGATGGTGCAG CCGCTATTAAAGGTTCGTTTGTTCAACGATT AA | 331 |
| SHLP6 (17) | Chimp | ATGTTGGATCAGGACATCCTAATGGTGCAG CCGGTATTAAGGGTTCGTTTGTTCAATGATTA | 332 |
| SHLP6 (M) | Orangutan | ATGTTGGATCAGGACATCCTAATGGTGCAG CCGCTATTAAAGGTTCGTTTGTTCAACGATT AA | 333 |
| SHLP6 (4a) | Orangutan | ATGTTGGATCAGGACATCCTAATGGTGTAG CTGCTATCAAGGGTTCGTTTGTTCCATGATT AA | 334 |
| SHLP6 (4b) | Orangutan | ATGTTGGATCAGGACATCCTGATGGTGCAG CCGCTATCAAAGTTTCATTTGTTCAAC | 335 |
| SHLP6 (4c) | Orangutan | ATGTTGGATCACGTCATCCTAATGGTGTAA CTGCTATTAAAGGTTCGTTTGTTCGACGATT GA | 336 |
| SHLP6 (9) | Orangutan | ATGTTGGATCAGGACATCCTAATGGTGTAG CCACTATTAAGGGTTCGTTTATTCAACAATT AA | 337 |
| SHLP6 (11) | Orangutan | ATGTTGGATCAGGACATCCTAATGGTGTAG CTGCTATTAAGGGTTTATTTGTTCAACAATT AA | 338 |
| SHLP6 (13a) | Orangutan | ATGTTGGATCAGGACATCCCAATGGTGCAG CCGCTATTAAAGGTTCGTTTGTTCAACGATT AA | 339 |
| SHLP6 (13b) | Orangutan | ATGTTGGATCAGGACATCCTAATGGTGTAG CTGCTATCAAGGGTTCGTTTGTTCAATGATTA | 340 |
| SHLP6 (14) | Orangutan | ATGTTGGATCAGGACATCCTAATGGTGTAG CCGCTAATAAGGTTCGTTTGTTCAA | 341 |
| SHLP6 (17a) | Orangutan | ATGTTGGATCAGGACATCCTAATGGTGCAG CCGCTATTAAAGGTTCGTTTGTTCAACGATT AA | 342 |
| SHLP6 (17b) | Orangutan | ATGTTGGATCAGGACATCCTAATGGTGCAG CCGCTATTAAGGGTTCGTTTGTTCAATGATTA | 343 |
| SHLP6 (17c) | Orangutan | ATGTTGGATCAGGACATCCCAAGGGTGCAG CTGCTATTAAAGTTTCGTTTGTTCAATGATTA | 344 |
| SHLP6 (1, 2, 4, 5, 6, 13) | Rhesus | ATGTTGGATCAGGACATCCTAATGGTGCAG CAGCTATCAAGGGTTCGTTTGTTCAACGATT AA | 345 |

TABLE 6-continued

Nucleic acid sequences encoding non-human SHLPs

| SHLP | Species | Nucleic acid sequence | SEQ ID (nt) |
|---|---|---|---|
| SHLP6 (5) | Rhesus | ATGTTGGATCAGGACATCCTAATGGTGCAG CAGCTATCAAGGGTTCTTTTGTTCAACAATT AA | 346 |
| SHLP6 (8) | Rhesus | ATGTTGCATCAGGACATCCTAATGGTGTAG CCGCTATCAAGGGTTCGTTTGTTCAATGATT AA | 347 |
| SHLP6 (18) | Rhesus | ATGTTGGATCAGGACATCCTGATGGTGTAG CAGCTATCAAGGGTTCGTTTGTTCAACGATT AA | 348 |
| SHLP6 (M) | Mouse | ATGTTGGATCAGGACATCCCAATGGTGTAG AAGCTATTAATGGTTCGTTTGTTCAACGATT AA | 349 |
| SHLP6 (M) | Rat | ATGTTGGATCAGGACATCCCAATGGTGCAG AAGCTATTAATGGTTCGTTTGTTCAACGATT AA | 350 |
| SHLP6 (unknown) | Opossum | ATGTTGGATCAGGACACCCCAATGGTGCAG CCGCTATTAAAGGTTCGTTTGTTCAACGATT AA | 351 |
| SHLP6 (unknown) | Platypus | ATGTTGGATCAGGACATCCAAATGGTGCAG CCGCTATTAATGGTTCGTTTGTTCAACGATT AA | 352 |
| SHLP6 (M, 35, 48, 701$_{a-c}$, 953$_{a-b}$, 1260, 1486, 1738, 1772, 1912, 2039, 2262, 2354, 2574, 2887) | Guinea Pig | ATGTTGGATCAGGACATCCTAATGGTGCAG CAGCTATTAAGGGTTCGTTTGTTCAACGATT AA | 353 |
| SHLP6 (13) | Guinea Pig | ATGTTGGATCTGGTCATCCTAATGGTGCAG CCGCTATCGAGGGTCCGTTTGTTCAACGATT AA | 354 |
| SHLP6 (79) | Guinea Pig | ATGCTGGATCAGGACGTCCTAATGGGGCAG CCACTATTAAGTGTTCGTTTGTTCAACGATT GA | 355 |
| SHLP6 (86) | Guinea Pig | ATGTTGGATCAGGACATCCTAATGGTGAGG CGGCTATTAAGGGTTCACTTGTTCAACGATT AA | 356 |
| SHLP6 (243) | Guinea Pig | ATGTTGGATCAGGACATCCTAATGGTGCAG CAGCTATTGAGGGTTCGTTTGTTCAACGATT AA | 357 |
| SHLP6 (18811, 18812) | Cat | ATGTTGGATCAGGACATCCCGATGGTGCAG CAGCTATCAAAGGTTCGTTTGTTCAACGATT AA | 358 |
| SHLP6 (30562, 66390, 112167$_{a-e}$) | Cat | ATGTTGGATCAAGACATCCCAATAGTACAG CAGCTATCAAAGGTTTGTTTGTTCAACGATT AA | 359 |
| SHLP6 (37160) | Cat | ATGTTGGATCAAGACATCCCAATAGTACAG CAGCTATCAAAGGTTTGTTTGTTCAACGATT AA | 360 |
| SHLP6 (63432) | Cat | ATGTTGGATCAGGACATCCCGATGGTGCAG CAGCTATCAAAGTTTCGTTTGTTCAAC | 361 |
| SHLP6 (92191) | Cat | ATGTTGGATCAGGACATCCCGATGGTGCAG CAGCTAGCGAAGGTTCGTTTGTTGGACGAT TAA | 362 |

TABLE 6-continued

Nucleic acid sequences encoding non-human SHLPs

| SHLP | Species | Nucleic acid sequence | SEQ ID (nt) |
|---|---|---|---|
| SHLP6 (M) | Dog | ATGTTGGATCAGGACATCCTAATGGTGCAG CAGCTATTAAGGGTTCGTTTGTTCAACGATT AA | 363 |
| SHLP6 (X) | Dog | ATGTTGGATCAGGACATCCTAATGGTGCAG CAGCTATTAAGGGTTAGTTTGTTCAACAATT AA | 364 |
| SHLP6 (M) | Horse | ATGTTGGATCAAGACATCCTAATGGTGCAA CCGCTATTAAGGGTTCGTTTGTTCAACGATT AA | 365 |
| SHLP6 (1) | Horse | ATGTTGGATCAAGACATCCTAATGGTGCAA CCGCTATTAAGGGTTTGTTTGTTCAACGATT AA | 366 |
| SHLP6 (M) | Cow | ATGTTGGATCAGGACATCCTGATGGTGCAA CCGCTATCAAAGGTTCGTTTGTTCAACGATT AA | 367 |
| SHLP6 (M) | Chicken | ATGTTGGATCAGGACAACCTAATGGTGCAA CCGCTATTAAGGGTTCGTTTGTTCAACGATT AA | 368 |
| SHLP6 (M) | Zebra Finch | ATGTTGGATCAGGACATCCTAGTGGTGCAG CCGCTACTAAGGGTTCGTTTGTTCAACGATT AA | 369 |
| SHLP6 (2) | Zebra Finch | ATGTTGGATCAGGACATCCTAGTGGTGCAG CCACTACTAAGGGTTCGTTTGTTCAATGATT TA | 370 |
| SHLP6 (927$_{a-b}$, 2224$_{a-b}$) | Lizard | ATGTTGGATCAGGACACCCAAATGGTGCAG CCGCTATTAAAGGTTCGTTTGTTCAACGATT AA | 371 |
| SHLP6 (18215) | X. tropicalis | ATGTTGGATCAGGGCATCCCAGTGGTGCAG CCGCTACTAAAGGTTCGTTTGTTCAACGATT AA | 372 |
| SHLP6 (M) | Zebrafish | ATGTTGGATCAGGACATCCTAATGGTGCAG CCGCTATTAAGGGTTCGTTTGTTCAACGATT AA | 373 |
| SHLP6 (unknown) | Tetradon | ATGTTGGATCAGGACATCCTAATGGTGCAG CCGCTATTAAGGGTTCGTTTGTTCAACGATT AA | 374 |
| SHLP6 (M) | Fugu | ATGTTGGATCAGGACATCCTAATGGTGCAG CCGCTATTAAAGGTTCGTTTGTTCAACGATT AA | 375 |
| SHLP6 (M) | Stickleback | ATGTTGGATCAGGACATCCTAATGGTGCAG CCGCTATTAAGGGTTCGTTTGTTCAACGATT AA | 376 |
| SHLP6 (M) | Medaka | ATGTTGGATCAGGACATCCTAATGGTGCAG CCGCTATTAAGGGTTTGTTTGTTCAACAATT AA | 377 |
| SHLP6 (M) | Lamprey | ATGTTGGATCGGGGCACCCCAATGGCGCAA AAGCTATTAAAGGTTCGTTTGTTCAACGATT AA | 378 |

In one aspect, novel peptides are provided herein comprising an amino acid sequence selected from SEQ ID NOs: 8-13, representing human SHLPs 1-6, respectively.

Also provided herein are peptide variants of SHLPs comprising an amino acid sequence selected from SEQ ID NOs: 8-13, representing human SHLPs 1-6, respectively, which is modified by the insertion, deletion, substitution, and/or addition of one or more amino acid residues. Peptides corresponding to SHLPs 1-6 and variants thereof are collectively referred to herein as "SHLPs." In addition, reference to a particular SHLP (e.g., SHLP6) includes the named SHLP as well as variants thereof. SHLPs provided herein may be derived from nuclear (genomic) DNA and/or mitochondrial DNA.

As used herein, the term "polynucleotide" means a polymeric form of nucleotides of at least 10 bases or base pairs in length, either ribonucleotides or deoxynucleotides or a modified form of either type of nucleotide, including single and double stranded forms of DNA.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as naturally occurring amino acids that are later modified, e.g., hydroxyproline, γ-carboxyglutamate, and O-phosphoserine. Amino acid analogs are compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium, where the peptide backbone and/or the R group are modified while the compound retains the same basic chemical structure as a naturally occurring amino acid. Amino acid mimetics refer to chemical compounds that have a structure that differs from the general chemical structure of an amino acid, but that functions in a manner similar to a naturally occurring amino acid.

The term "endogenous" refers to a protein, nucleic acid, lipid or other biomolecule produced or originating within the body or within cells, organs, or tissues of the body of a subject. In some aspects, SHLPs referred to herein comprise endogenous peptides encoded by the ORFs indicated in Table 1. Endogenous SHLPs provided herein can be from any species and are preferably from a mammal. In some preferred aspects, endogenous SHLP nucleic acids and peptides provided herein are human SHLP nucleic acids and peptides.

The term "exogenous" refers a protein, nucleic acid, lipid, or other biomolecule originating outside the body of a subject.

In some aspects, an "isolated" or "purified" SHLP or variants thereof is substantially free of cellular material or other contaminating proteins from the cell or tissue source from which the protein is derived, or substantially free of chemical precursors or other chemicals when chemically synthesized. For example, having less than about 30%, 20%, 10%, or 5% (by dry weight) of heterologous protein (also referred to herein as a "contaminating protein"), culture medium, and/or chemical precursors or other chemicals.

In some preferred aspects, SHLPs provided herein are functionally equivalent to endogenous SHLPs of SEQ ID NO:8-13 in that they possess at least one common structural and/or functional activity in a biological system, such as a cellular or animal model described herein. In some preferred aspects, variants of SHLPs provided herein exhibit one or more physiological or therapeutic activities associated with the corresponding human SHLP. Unless otherwise indicated, an activity of substantially the same quality or nature of that observed for a corresponding SHLP is sufficient to define a peptide as a variant of the SHLP.

In some aspects, functionally equivalent SHLPs comprise amino acid sequences which differ from SEQ ID NOs: 8-13 in the identities of no more than 10, 9, 8, 7, 6, 5, 4, 3, 2, or 1 nonessential amino acid residues. In further aspects, functionally equivalent SHLPs comprise amino acid sequences which differ from SEQ ID NOs: 8-13 in the identities of no more than three, or preferably no more than two, or more preferably no more than one essential amino acid residues.

In some aspects, SHLPs provided herein have neuroprotective activity against cell death associated with one or more neurodegenerative disease-related insults, such as but not limited to, cell death induced by mutant SOD1 in amyotrophic lateral sclerosis, mutant APP, PS-1, PS-22, and/or amyloid-beta (Aβ) peptides in Alzheimer's disease, and/or polyglutamine repeat mutations in Huntington's disease. In further aspects, SHLPs have general neuroprotective activity against a broad range of insults, including but not limited to, NMDA-induced excitotoxicity, cerebral ischemia/reperfusion injury, and/or prion peptide-induced apoptosis. Methods for assaying peptides for neuroprotective activity are described herein and are known in the art, including, e.g., in Hashimoto et al., *J. Neuroscience,* 21(23):9235-9245 (2001), Hashimoto et al., *Proc Natl Acad Sci USA,* 98:6336-6341 (2001)), Caricasole et al., *FASEB J.,* 16:1131-1133 (2002), Sponne et al., *Mol. Cell. Neurosci.,* 25:95-102 (2004), and Niikura et al., *Current Neuropharmacol.,* 4:139-147 (2006), all of which are herein incorporated by reference.

In further aspects, SHLPs provided herein have neuroprotective activity against neurotoxicity in the peripheral nervous system, such as but not limited to, neurotoxicity associated with chemotherapeutic agents, radiation therapy, anti-infective agents, and/or other therapeutics. For example, in various aspects, SHLPs provided herein may exert neuroprotective activity against peripheral neurotoxicity associated with Vinca alkaloids, platinum compounds, suramin, taxanes, and/or other chemotherapeutic agents.

In some aspects, SHLPs provided herein exhibit cell survival promoting (e.g., anti-apoptotic) activity against disease-associated cells and/or stimuli, such as but not limited to, cells of subjects suffering from diabetes, kidney disease, and/or cancer. For example, in some aspects, SHLPs have anti-apoptotic activity against pancreatic β-cells of diabetic subjects and/or tumor cells. Methods for assaying peptides for anti-apoptotic activity are described herein and are known in the art, including, e.g., Ikonen et al., *Proc Natl Acad Sci USA,* 100:13042-13047 (2003)), which is herein incorporated by reference.

In some aspects, SHLPs inhibit IGFBP-3-induced apoptosis of pancreatic β-cells of diabetic subjects. Methods for assaying binding to IGFBP-3 and IGFBP-3-induced cell death are known in the art and are described, e.g., in Ikonen et al., *Proc Natl Acad Sci USA,* 100:13042-13047 (2003)), which is herein incorporated by reference. In further aspects, SHLP activity is independent of IGFBP-3.

In further aspects, SHLPs provided herein have cell growth-stimulating activity against disease-associated cells, such as but not limited to, pancreatic β-cells of diabetic subjects.

In further aspects, SHLPs provided herein have differentiation-stimulating activity against disease-associated cells. For example, in some aspects, SHLPs stimulate insulin-induced differentiation of adipocytes from diabetic patients.

In some aspects, SHLPs provided herein are capable of homo- and/or hetero-dimerizing and/or multimerizing with one or more peptides, such as but not limited to, another SHLP or humanin (HN). Methods for assaying peptides for dimerization and multimerization are known in the art and are described, e.g., in U.S. Pat. Pub. No. 2005/0233413, which is herein incorporated by reference. In some aspects, one or more activities of an SHLP are dimerization- and/or multimerization-dependent.

In further aspects, SHLPs provided herein are subject to secretion by one or more cell types. Methods for assaying peptide secretory activity are known in the art and are described, e.g., in U.S. Pat. No. 7,314,864, which is herein incorporated by reference. In some aspects, one or more activities of an SHLP are dependent on secretory activity.

In some aspects, SHLPs provided herein have one or more cell protective activities. For example, in some aspects, SHLPs are capable of enhancing resistance to environmental stress, such as but not limited to, heat shock, serum withdrawal, chemotherapy, and/or radiation. In further aspects, SHLPs provided herein are capable of inhibiting intracellular production of reactive oxygen species (ROS). Methods for assaying peptides for stress resistance activity are described herein and are known in the art, including, e.g., Ikonen et al., *Proc Natl Acad Sci USA*, 100:13042-13047 (2003) and Kariya et al., *Neuroreport.*, 13:903-907 (2002), both of which are herein incorporated by reference.

In some aspects, SHLPs provided herein have anticancer activity. For example, in some aspects, SHLPs have pro-apoptotic activity against cancer cells, such as but not limited to, prostate cancer cells and/or breast cancer cells. In further aspects, SHLPs have anti-proliferative activity against cancer cells, such as but not limited to, prostate cancer cells and/or breast cancer cells. Methods for assaying SHLPs described herein for anticancer activity against additional cancers are known in the art and various well characterized human cancer cell lines can be obtained from, e.g., the American Type Culture Collection (ATCC).

In further aspects, SHLPs provided herein have anticancer activity in vivo. For example, in some aspects, SHLPs have growth inhibitory activity against tumors in vivo, such as but not limited to, prostate cancer tumors. In further aspects, SHLPs increase apoptosis, decreased angiogenesis, and/or reduce proliferation of tumors and/or tumor cells, such as but not limited to, prostate cancer tumors. Methods for assaying peptides for anticancer activity are described herein and are well known in the art.

In some aspects, SHLPs provided herein modulate the expression of one or more cancer-related genes, such as but not limited to, apoptosis genes, metastasis genes, and/or angiogenesis genes. For example, in various aspects, SHLPs modulate the expression of one or more cancer-related genes set forth in Table 8.

SHLP nucleic acids and peptides include fragments of full-length (e.g., naturally occurring) SHLP nucleic acids and peptides.

The invention also provides chimeric or fusion proteins. As used herein, a "chimeric protein" or "fusion protein" comprises an SHLP or variant thereof operably linked to a heterologous polypeptide (i.e., a polypeptide other than the SHLP or variant thereof). Within the fusion protein, the term "operably linked" indicates that the heterologous polypeptide is fused in-frame to the SHLP, via the N-terminus and/or C-terminus of the SHLP.

Fusion proteins may be produced by peptide synthesis or by expressing recombinant DNA. Examples of polypeptides that may comprise a fusion protein provided herein include, but are not limited to, tags, leader sequences, signal peptides, green fluorescent proteins (GFP), maltose-binding proteins, glutathione S-transferase (GST), antibodies and antibody fragments.

Fusion polypeptides are typically intended to facilitate polypeptide purification. For example, a leader sequence or signal peptide can induce extracellular secretion of a fusion polypeptide by genetically engineered host cells. Examples of purification tags and the like that are known in the art include, e.g., FLAG, 6×His, 10×His, influenza hemagglutinin (HA), VSV-GP fragments, T7-tag, HSV-tag, and E-tag.

SHLPs also include salts of peptides provided herein, including acid-addition salts and base-addition salts. Examples of acid-addition salts include: salts of mineral acids such as hydrochloride, sulfate, nitrate, hydrobromide, and phosphate; and salts of organic acids such as acetate, butyrate, succinate, citrate, oxalate, malate, methanesulfonate, benzoate, maleate, and tartrate. Examples of base-addition salts include: alkali metal salts (e.g., sodium salts and potassium salts) and alkaline-earth metal salts (e.g., calcium salts and magnesium salts); and salts formed with organic bases such as ammonium salts (e.g., ammonium salts, methylammonium salts and triethylammonium salts) and amino acid salts (e.g., lysine salts and arginine salts).

SHLPs also include hydrates and solvates of peptides provided herein.

In some aspects, an SHLP or variant thereof is at least about 30%, preferably 35%, 40%, 45%, 50%, 55%, 65%, 75%, 85%, 95% or 98% identical to an amino acid sequence of SEQ ID NO: 8-13.

In some aspects, an SHLP provided herein has an amino acid sequence which is "substantially identical" to the sequence of the corresponding human SHLP, in that the sequence is at least about 85%, 86%, 87%, 88%, 89%, 90%, 91%, 92%, 93%, 94%, 95%, 96%, 97%, or 98% or more identical to the sequence of a reference sequence, such as the corresponding endogenous human SHLP.

In further aspects, an SHLP or variant thereof comprises at least 5, 6, 7, 8, 9, 10, 11, 12, 13, 14, 15, or more contiguous amino acids of an amino acid sequence of SEQ ID NO: 8-13.

In another aspect, the invention pertains to isolated nucleic acid molecules that encode an SHLP or a variant thereof. As used herein, the term "nucleic acid" is intended to include DNA molecules (e.g., cDNA or genomic DNA), RNA molecules (e.g., mRNA), and analogs of the DNA or RNA, such as those generated using nucleotide analogs. The nucleic acid molecules can be single-stranded or double-stranded, and in some aspects are double-stranded DNA.

SHLP nucleic acids provided herein include, but are not limited to, probes and primers for detecting and/or amplifying DNAs and RNAs encoding an SHLP. SHLP nucleic acids provided herein also include nucleotides and nucleotide derivatives (for example, antisense oligonucleotides, DNAs encoding ribozymes, and the like) for modulating the expression of an SHLP.

Another aspect of the invention provides vectors, e.g., recombinant expression vectors, comprising a nucleic acid molecule of the invention. In another aspect, the invention provides host cells containing such a vector or engineered to contain and/or express a nucleic acid molecule of the invention. The invention also provides methods for producing a polypeptide of the invention by culturing, in a suitable medium, a host cell of the invention such that a polypeptide of the invention is produced.

In some aspects, an SHLP nucleic acid is identical, or at least 50%, 55%, 65%, 75%, 85%, 95%, or 98% identical to a sequence selected from SEQ ID NOS: 1-6, wherein the human mitochondrial DNA of Table 1 is accession number AF346981.1.

The degree of similarity between a nucleic acid sequence and one or more reference nucleic acid sequences can be expressed in terms of conditions under which the nucleic acid would hybridize to the reference nucleic acid. For example, in some aspects, an SHLP nucleic acid or variant thereof hybridizes under stringent conditions to a nucleotide sequence of Table 1 or a sequence selected from SEQ ID NOS: 1-6, or to a complement thereof. In various preferred aspects, an SHLP nucleic acid encodes a polypeptide that exhibits at least one structural and/or functional feature of an SHLP.

The phrase "stringent hybridization conditions" generally refers to conditions under which a probe will hybridize to its target subsequence, typically in a complex mixture of nucleic acids, but to no other sequences. In some aspects, "stringent hybridization conditions" are conditions for hybridization and washing under which nucleotide sequences at least 60%, 65%, 70%, 75%, or more identity typically remain hybridized. Stringent conditions are known to those skilled in the art and can be found, e.g., in Current Protocols in Molecular Biology, John Wiley & Sons, N.Y. (1989), 6.3.1-6.3.6.

Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

A preferred, non-limiting example of stringent hybridization conditions are hybridization in 6× sodium chloride/sodium citrate (SSC) at about 45 C., followed by one or more washes in 0.2×SSC, 0.1% SDS at 50-65 C. In various preferred aspects, the SHLP nucleic acid or variant thereof encodes a polypeptide that exhibits at least one structural and/or functional feature of an SHLP.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

For PCR, a temperature of about 36° C. is typical for low stringency amplification, although annealing temperatures can vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 seconds to 2 min., and an extension phase of about 72° C. for 1-2 min. Protocols and guidelines for low and high stringency amplification reactions are provided, e.g., in Innis et al PCR Protocols, A Guide to Methods and Applications, Academic Press, Inc. N.Y. (1990).

In some aspects, SHLP nucleic acids provided herein comprise antisense to the coding strand of a nucleic acid described herein.

An "isolated" nucleic acid molecule is one which is separated from other nucleic acid molecules that are present in the natural source of the nucleic acid molecule. Preferably, an "isolated" nucleic acid molecule is free of sequences (preferably protein encoding sequences) which naturally flank the nucleic acid (e.g., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

Nucleic acid molecules provided herein can be isolated using standard hybridization and cloning techniques (e.g., as described in Sambrook et al., eds., Molecular Cloning: A Laboratory Manual, 2nd ed., Cold Spring Harbor, Laboratory, Cold Spring Harbor Laboratory Press, Cold Spring Harbor, N.Y., 1989).

A nucleic acid molecule encoding a variant SHLP can be created by introducing one or more nucleotide substitutions, additions or deletions into an SHLP nucleotide sequence provided herein, such that one or more amino acid substitutions, additions or deletions are introduced into the encoded protein. Mutations can be introduced by standard techniques, such as site-directed mutagenesis and PCR-mediated mutagenesis.

In some aspects, isolated nucleic acids provided herein encompass mutants having at least about 70%, 75%, 80%, 85%, 90%, 95%, 97%, 98%, or 99% or higher identity to a nucleotide sequence of SEQ ID NOs: 1-6, representing the codings sequences of human SHLPs 1-6, respectively.

In some preferred aspects, SHLPs provided herein are limited to one or more (e.g., preferably less than 3, less than 2, or 1) conservative amino acid substitutions. In further aspects, the conservative amino acid substitution(s) are at one or more non-essential amino acid residues. In some aspects, one or more residues are determined as being non-essential for one or more biological activities of an SHLP, for example by making a series of peptides with random mutations along the length of the sequence, and screening the peptides for the biological activity.

A "conservative amino acid substitution" is one in which the amino acid residue is replaced with an amino acid residue having a similar side chain. Amino acid substitutions may be made on the basis of similarity in polarity, charge, solubility, hydrophobicity, hydrophilicity, and/or amphipathic nature. Families of amino acid residues having similar side chains have been defined in the art and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A predicted nonessential amino acid residue in an SHLP polypeptide can typically be replaced with another amino acid residue from the same side chain family.

In some aspects, a conservative variant of a nucleic acid or amino acid sequence provided herein comprises one or more conservative substitutions relative to a reference sequence at non-essential amino acids or codons coding for non-essential amino acids. A "non-essential" amino acid residue is a residue that can be altered from the wild-type sequence (e.g., a sequence of SEQ ID NO: 8-13) without abolishing or substantially altering the therapeutic activity of the peptide, whereas an "essential" amino acid residue is a residue cannot be altered without introducing such a change.

In some aspects, variant amino acid and/or nucleic acid sequences provided herein are "conservatively modified" variants of a reference sequence, such as an endogenous SHLP sequence. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Nucleic acid sequences described herein which encode a polypeptide include all possible silent variations of the nucleic acid. One of skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

Conservatively modified variants provided herein are in addition to and do not exclude polymorphic variants, interspecies homologs, and alleles of the invention.

The terms "identical" or percent "identity," in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region. Methods of aligning sequences for comparison are well-known in the art. Optimal alignment of sequences for comparison can be conducted, e.g., by the local homology algorithm of Smith & Waterman, Adv. Appl. Math., 1981, 2:482, by the homology alignment algorithm of Needleman & Wunsch, J. Mol. Biol., 1970, 48:443, by the search for similarity method of Pearson & Lipman, Proc. Nat'l. Acad. Sci. USA, 1988, 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology, Ausubel et al., eds. 1995 supplement)).

Sequences referred to herein can be aligned and sequence identity and other quantitative comparison measures can be determined using the BLAST or BLAST 2.0 sequence comparison algorithms, which are described in Altschul et al., Nuc. Acids Res., 25: 3389-3402, 1977 and Altschul et al., J. Mol. Biol. 215: 403-410, 1990, respectively. Software for performing BLAST analyses is publicly available through the National Center for Biotechnology Information (found on the web at the site: www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 1989, 89:10915) alignments (B) of 50, expectation (E) of 10, M=5, N=−4, and a comparison of both strands. In some aspects, the percent identity of nucleic acid sequences is determined using the ALIGN program of the GCG software package with a PAM120 weight residue table, a gap length penalty of 12, and a gap penalty of 4.

In other aspects, sequences can be aligned and compared by visual inspection, for example when dealing with short peptides. Unless an alternative window is specified, recited degree of identity is with respect to the full-length human SHLP. In some aspects, SHLPs provided herein have a specified degree of identity with a reference peptide.

In the case of an polynucleotide which is longer than or equivalent in length to the reference sequence, the comparison is made with the full length of the reference sequence. Where the polynucleotide is shorter than the reference sequence, the comparison is made to segment of the reference sequence of the same length.

SHLPs provided herein may be modified chemically and/or biologically. Examples of such modifications include, but are not limited to, functional group introduction such as alkylation, acylation, amidation, esterification, halogenation, amination, carboxylation, and pegylation, functional group conversion such as oxidation, reduction, addition, and elimination, glycosylation, lipid compound introduction, phosphorylation, and/or biotinylation. Such modification(s) may, for example, stabilize and/or enhance the biological activity an SHLP.

SHLPs can be produced according to any peptide synthesis technique known in the art. For example, SHLPs can be synthesized by a variety of chemical methods such as the azide method, acid chloride method, acid anhydride method, mixed anhydride method, DCC method, activated ester method (e.g., P-nitrophenyl ester, N-hydroxysuccinimide ester, and cyanomethyl ester methods), methods using Woodward's reagent K, carboimidazole method, oxidation-reduction method, and DCC-additive (HONB, HOBt, or HOSu)

method, as described, for example, in "The Peptides" Vol. 1 (1966) [Schroder and Lubke, Academic Press, New York, U.S.A.] or "Peptide Synthesis" [Izumiya et al., Maruzen Co., Ltd., (1975)]. Such methods can be applied to both solid-phase and liquid-phase syntheses.

A variety of commercially available peptide synthesizers can be utilized in conjunction with solid phase synthetic methods. The synthesis can be performed more efficiently by protecting and deprotecting functional groups, if necessary, as described, e.g., in Protective Groups in Organic Synthesis (T. W. Greene, John Wiley & Sons Inc., 1981).

Peptides can be desalted and purified according to known methods, including but not limited to, ion-exchange chromatography (e.g., DEAE-cellulose), partition chromatography (e.g., Sephadex LH-20 and Sephadex G-25), normal phase chromatography (e.g., silica gel), reverse phase chromatography (e.g., ODS-silica gel), and high performance liquid chromatography.

Nucleic acids provided herein can be used for producing the encoded SHLPs using recombinant expression methods known in the art. Typically, DNA encoding the polypeptide of interest is inserted into a recombinant vector containing cis elements (e.g., promoters and enhancers), splicing signals, polyA-addition signals, selective markers, ribosome-binding sequences (SD sequences), terminators, and the like to direct expression of the target nucleic acid. A prokaryotic or eukaryotic host cell is transformed with the vector, and the polypeptide of interest is separated and purified from the host cells or the host cell culture supernatant. Separation and purification of the polypeptide can be facilitated by optionally expressing the polypeptide in the form of a fusion polypeptide with a signal peptide for extracellular secretion and/or a tag for purification/detection. A signal peptide for extracellular secretion is preferably selected to be suitable for the host cell used for expression of the fusion protein. For example, if the host cell is an animal cell, the fusion protein could comprise a signal peptide from the N terminus of a growth and differentiation factor (e.g., a cytokine) or receptor thereof.

A variety of host-vector systems are known in the art for use with prokaryotic and eukaryotic host cells (e.g., *Escherichia coli, Bacillus subtilis*, yeast, Basidiomycetes, insect cells, plant cells, and mammal cells). Examples of such vectors include plasmid, phage, and virus vectors. Examples of therapeutic vectors include adenovirus vectors, adeno-associated virus vectors, herpes virus vectors, retrovirus vectors, and lentivirus vectors (e.g., Robbins and Ghivizzani, *Pharmacol. Ther.*, 80: 35-37 (1998); Engel and Kohn, *Front Biosci.*, 4: e26-33 (1999); and Lundstrom, *J. Recept. Signal. Transduct. Res.*, 19: 673-686 (1999)).

SHLPs provided herein include recombinant peptides (peptides made using recombinant techniques) in addition to synthetic and naturally occurring peptides. A recombinant protein can typically be distinguished from naturally occurring protein by one or more characteristics. For example, recombinant peptides can be isolated from some or all of the proteins and compounds with which it is normally associated in a wild type host. For example, isolated peptides provided herein are unaccompanied by at least some of the material with which they are normally associated in their natural state, typically constituting about 0.5% to about 5% by weight of the total protein in a given sample. In various aspects, a substantially pure peptide comprises at least about 75% by weight of the total protein, or at least about 80% by weight of the total protein, and typically at least about 90% by weight of the total protein.

In another aspect, methods are provided for modulating activity of an SHLP comprising contacting a cell with an agent that modulates, inhibits, and/or stimulates the activity or expression of an SHLP, such that activity or expression in the cell is modulated. In one aspect, the agent is an antibody that specifically binds to an SHLP or variant thereof.

In another aspect, the agent modulates expression of an SHLP or variant thereof by modulating transcription, splicing, or translation of an mRNA encoding an SHLP or variant thereof. In yet another aspect, the agent is a nucleic acid molecule having a nucleotide sequence that is antisense to the coding strand of an mRNA encoding an SHLP or variant thereof.

In yet a further aspect, the invention provides substantially purified antibodies or fragments thereof, and non-human antibodies or fragments thereof, which antibodies or fragments specifically bind to an SHLP or variant thereof. Preferably, antibodies against one SHLP (e.g., SHLP6) recognize an epitope which is unique to that SHLP relative to other SHLPs (e.g., SHLP2), such that the antibodies show little or no cross-reactivity between SHLPs. In some aspects, antibodies provided herein are capable of reducing, eliminating, and/or otherwise modulating an activity of the SHLP to which it selectively binds.

In various aspects, the substantially purified antibodies of the invention, or fragments thereof, can be human, non-human, chimeric and/or humanized antibodies. non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In some aspects, anti-SHLP antibodies provided herein are polyclonal antibodies. Polyclonal antibodies can be produced by methods known to those of skill in the art. In brief, a suitable immunogen, for example, a purified peptide is mixed with an adjuvant and injected into a host animal. Antigenic determinants on polypeptides are typically 3 to 10 amino acids in length. Accordingly, the immunogen can be a peptide of 3 or more amino acids, or more typically of least 5 amino acids, or preferably of at least 10 amino acids in length. The peptide immunogen may be coupled to an appropriate carrier (e.g., GST and keyhole limpet hemocyanin) or incorporated into an immunization vector, such as a recombinant vaccinia virus (see, U.S. Pat. No. 4,722,848). The host's immune response to the immunogen preparation is monitored by taking test bleeds and determining the titer of reactivity to the peptide of interest. When appropriately high titers of antibody are obtained, blood is collected from the animal and antisera are prepared. Further fractionation of the antisera can be performed to enrich for antibodies reactive to the peptide of interest. See, e.g., Coligan, Current Protocols in Immunology, Wiley/Greene, NY, 1991; and Harlow and Lane, supra, each incorporated herein by reference in their entirety.

In some aspects, an anti-SHLP antibody provided herein are monoclonal antibodies. The monoclonal antibodies can be prepared from a hybridoma which secretes an antibody having the desired reactivity and affinity. Immortalized antibody-producing cell lines can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol. 133:3001, 1984; Brodeur et al., Monoclonal Antibody Production Techniques and Applications, Marcel Dekker, Inc., New York, 1987, pp. 51-63, each incorporated herein by reference in their entirety). In some instances, it may be desirable to prepare monoclonal antibodies from a mammalian host, such as a mouse, a rodent, a primate, or a human. Methods for preparing monoclonal antibodies are described, e.g., in Stites et al. (eds.) Basic and Clinical Immunology (4th ed.) Lange Medical Publications, Los Altos, Calif., and references cited therein; Harlow and Lane, Supra; Goding, 1986; Monoclonal Antibodies: Principles and Practice (2d ed.) Academic Press, New York, N.Y.; and Kohler et al., Nature 256: 495-497, 1975, each incorporated herein by reference in their entirety.

Also provided herein are methods of treating a subject having, or at risk of having, a disease or condition treatable by an SHLP by administering an effective amount of an SHLP or a pharmaceutical composition thereof to the subject.

SHLPs provided herein can be administered by themselves, or they can be co-administered with one or more other agents, such as another agent provided herein or a different agent or agents. An SHLP and one or more additional agents can be co-administered simultaneously (in the same or separate formulations) or consecutively. Furthermore, SHLPs provided herein can be administered as an adjuvant therapy.

In some aspects, an SHLP is co-administered with one or more of a different SHLP provided herein, humanin, or a variant of humanin, such as but not limited to, humanin-S14G, humanin GF6A, or colivelin.

Methods provided herein can be used to treat any disease, condition, or disorder which is responsive to treatment with an SHLP. As used herein, "treating" includes, but is not limited to, prevention, amelioration, alleviation, and/or elimination of a disease, disorder, or condition being treated or one or more symptoms of the disease, disorder, or condition being treated, as well as improvement in the overall well being of a patient, as measured by objective and/or subjective criteria.

A "subject" of a method provided herein refers to any mammalian patient to which peptides or compositions of the invention can be beneficially administered. The term mammal refers to both humans and non-human primates, as well as experimental or veterinary animals, such as rabbits, rats, mice, and other animals. In some aspects, a subject in need of treatment with an SHLP is identified using a screening method for determining risk factors associated with a targeted or suspected disease or condition or to determine the status of an existing disease or condition.

In some aspects, an "effective amount" of an SHLP provided herein is an amount sufficient to provide a measurable reduction in symptoms or other beneficial effect with respect to a disease or condition targeted for treatment.

In some aspects, methods are provided herein for treating a condition for which apoptotic cell death, inflammation, autoimmunity, angiogenesis, and/or metastasis is an etiological determinant.

In some aspects, SHLPs are administered to treat a condition associated with cellular stress responses, such as but not limited to, the induction of heat shock proteins and/or metabolic and oxidative stress. The cellular stress response can be responsive to any stressor, including, e.g., thermal, immunological, cytokine, oxidative, metabolic, anoxic, endoplasmic reticulum, protein unfolding, nutritional, chemical, mechanical, osmotic and glycemic stresses.

In some aspects, SHLPs are administered according to a method provided herein to treat an inflammatory condition, such as but not limited to, diabetes, cardiovascular disease, kidney disease, retinopathy, obesity, metabolic disease, neurodegenerative disease, gastrointestinal disease, autoimmune disease, rheumatological disease or infectious disease.

In some aspects, the disease or condition is a neurodegenerative disease. Without being limited by a particular theory, it is believed that certain SHLPs provided herein have one or more activities capable of repairing and/or preventing neurodegenerative damage of neural cells and/or other cell types. In some aspects, the methods involving administering SHLP2, SHLP3, and/or a variant thereof to a subject suffering from a neurodegenerative disease. Advantageously, administering an SHLP according to methods provided herein provides a protective effect against neurodegenerative effects, including for example, cell death induced by the SOD1 mutant in amyotrophic lateral sclerosis subjects, mutant APP, PS-1, PS-22, or amyloid-beta (Aβ) peptides in Alzheimer's disease subjects, and/or polyglutamine repeat mutations in Huntington's disease subjects.

"Neurodegenerative diseases" treatable according to methods provided herein are progressive diseases resulting in the degeneration and/or loss of neurons, for example due to neuronal cell death (apoptosis). Examples of neurodegenerative diseases include, but are not limited to, cerebral degenerative diseases (e.g., Alzheimer's disease (AD), Parkinson's disease, progressive supranuclear palsy, and Huntington's disease (HD)), and spinal degenerative disease/motor neuron degenerative diseases (e.g., amyotrophic lateral sclerosis (ALS), (SMA: Werdnig-Hoffmann disease or Kugelberg-Welander syndrome), spinocerebellar ataxia, bulbospinal muscular atrophy (BSMA: Kennedy-Alter-Sung syndrome)).

A "motor neuron degenerative disease" is a neurodegenerative disease characterized by a progressive, retrograde disorder of upper and lower motor neurons that control motion in the body. In further aspects, SHLPs and compositions thereof are also effective in ameliorating conditions resulting from motor neuron degenerative disease, such as muscular atrophy, muscular weakness, bulbar palsy (muscular atrophy or weakness in the face, pharynx, and tongue, and aphasia or dysphagia caused thereby), muscular fasciculation, and respiratory disorder.

In further aspects, methods are provided herein for treating diabetes and/or diabetes related complications by administering an effective amount of an SHLP to a patient in need of treatment. Diabetes is characterized by a progressive inability to manage glucose metabolism, leading to elevated plasma glucose levels. Secondary complications that arise after prolonged exposure to elevated blood sugar, including cardiovascular complications, kidney disease, and retinopathies, pose the greatest health risks to diabetic patients and impose significant economic and social costs globally. Patients with Type 1 diabetes, or insulin-dependent diabetes mellitus (IDDM), produce little or no insulin and therefore exhibit impaired glucose regulation and utilization. Patients with Type 2 diabetes, or noninsulin dependent diabetes mellitus (NIDDM), typically have normal or even elevated plasma insulin levels but exhibit decreased sensitivity to the effects of insulin on glucose metabolism. Currently available diabetes therapies focus on managing the patient's blood sugar levels, as there are no known therapies capable of ameliorating the underlying deficiencies in insulin signaling and glucose metabolism.

Without being limited by a particular theory, it is believed that glucose handling and metabolism is impaired in some diabetes patients due to damage and/or death of insulin producing pancreatic β cells and/or other cells involved in insulin signaling, and that SHLPs provided herein have one or more activities capable of preventing and/or repairing such effects. For example, β cells are selectively targeted and destroyed by autoimmune processes in many Type I diabetic patients. Advantageously, SHLPs used for treating diabetes and/or related complications according to methods provided herein have anti-apoptotic activity against and/or stimulate proliferation of pancreatic β cells, such that administering the SHLPs increases the number of insulin producing β cells and the level of insulin produced by the patient. In some preferred aspects, the methods comprise administering SHLP2, SHLP3, and/or a variant thereof.

The present invention also includes methods of treating cancer comprising administering an effective amount of an SHLP or a variant thereof to a subject in need of treatment. In some preferred aspects, the methods comprise administering an effective amount of SHLP6 or a variant thereof.

SHLPs provided herein exert a variety of anticancer effects and can be used to treat a wide range of cancers and other proliferative disorders. A "cancer" refers generally to a disease characterized by uncontrolled, abnormal cell growth and proliferation. A "tumor" or "neoplasm" is an abnormal mass of tissue that results from excessive, uncontrolled, and progressive cell division.

Methods described herein are useful for treating cancers and proliferative disorders of any type, including but not limited to, carcinomas, sarcomas, soft tissue sarcomas, lymphomas, hematological cancers, leukemias, germ cell tumors, and cancers without solid tumors (e.g., hematopoietic cancers). In various aspects, SHLPs can be used to treat cancers and/or tumors originating from and/or effecting any tissue, including but not limited to, lung, breast, epithelium, large bowel, rectum, testicle, bladder, thyroid, gallbladder, bile duct, biliary tract, prostate, colon, stomach, esophagus, pancreas, liver, kidney, uterus, cervix, ovary, and brain tissues.

Non-limiting examples of specific cancers treatable with SHLPs include, but are not limited to, acute lymphoblastic leukemia, acute myeloid leukemia, chronic lymphocytic leukemia, chronic myelogenous leukemia, adrenocortical carcinoma, AIDS-related lymphoma, anal cancer, astrocytoma, cerebral basal cell carcinoma, bile duct cancer, extrahepatic bladder cancer, bladder cancer, bone cancer, osteosarcoma/malignant fibrous histiocytoma, brain stem glioma, brain tumor, brain stem glioma, cerebral astrocytoma/malignant glioma, ependymoma, medulloblastoma, supratentorial primitive neuroectodermal tumor, visual pathway and hypothalamic glioma, breast cancer, male bronchial adenomas/carcinoids, Burkitt's lymphoma, carcinoid tumor, gastrointestinal carcinoma of unknown primary central nervous system lymphoma, cervical cancer, chronic lymphocytic leukemia, chronic myelogenous leukemia, chronic myeloproliferative disorders, colon cancer, colorectal cancer, cutaneous t-cell lymphoma, mycosis fungoides and sezary syndrome, endometrial cancer, ependymoma, esophageal cancer, Ewing's family tumors, germ cell tumors, extrahepatic bile duct cancer, eye cancer, intraocular melanoma, retinoblastoma, gallbladder cancer, gastric (stomach) cancer, gastrointestinal carcinoid tumors, ovarian gestational trophoblastic tumors, glioma, hypothalamic skin cancer (melanoma), skin cancer (non-melanoma), skin carcinoma, small cell lung cancer, small intestine cancer, soft tissue sarcoma, squamous cell carcinoma, squamous neck cancer with occult primary, metastatic stomach (gastric) cancer, stomach (gastric) cancer, t-cell lymphoma, testicular cancer, thymoma, thymic carcinoma, thyroid cancer, transitional cell cancer of the renal pelvis, ureter trophoblastic tumors, transitional cell cancer, urethral cancer, uterine cancer, uterine sarcoma, vaginal cancer, hypothalamic glioma, vulvar cancer, Waldenstrom's macroglobulinemia, Wilms' tumor, hairy cell leukemia, head and neck cancer, hepatocellular (liver) cancer, Hodgkin's lymphoma, hypopharyngeal cancer, islet cell carcinoma (endocrine pancreas), Kaposi's sarcoma, kidney (renal cell) cancer, kidney cancer, laryngeal cancer, hairy cell lip and oral cavity cancer, liver cancer, lung cancer, non-small cell lung cancer, small cell lymphoma, Burkitt's lymphoma, cutaneous t-cell, Hodgkin's lymphoma, non-Hodgkin's lymphoma, Waldenstrom's malignant fibrous histiocytoma of bone/osteosarcoma medulloblastoma, intraocular (eye) merkel cell carcinoma, mesothelioma, malignant mesothelioma, metastatic squamous neck cancer with occult primary multiple endocrine neoplasia syndrome, multiple myeloma/plasma cell neoplasm mycosis fungoides myelodysplastic syndromes, myelodysplastic/myeloproliferative diseases, myelogenous leukemia, multiple myeloproliferative disorders, chronic nasal cavity and paranasal sinus cancer, nasopharyngeal cancer, pleuropulmonary blastoma, osteosarcoma/malignant fibrous histiocytoma of bone, pheochromocytoma, pineoblastoma, and supratentorial primitive neuroectodermal tumors.

In some preferred aspects, the cancer is breast cancer
In some preferred aspects, the cancer is prostate cancer.
SHLPs provided herein can have a variety of anticancer activities, such as but not limited to, inducing apoptosis in cancerous cells, inhibiting tumor angiogenesis, inhibiting tumor metastasis, modulating the cell cycle, inhibiting cancer cell proliferation, promoting cancer cell differentiation, inhibiting production of and/or protecting against reactive oxygen species, and enhancing stress resistance.

In some aspects, administering an SHLP according to a method provided herein enhances efficacy and/or decreases adverse effects of an established cancer therapy. For example, in some aspects, administering an SHLP according to a method provided herein protects non-cancerous cells against the adverse effects of a non-specific cancer therapy, such as radiation or chemotherapy. In further aspects, administering an SHLP according to a method provided herein enhances the anticancer activity of another cancer therapy, such as radiation or chemotherapy.

In some aspects, methods are provided herein for inducing cell death in cancer cells and/or tumor cells, the methods comprising administering an SHLP described herein in an amount sufficient to induce cancer and/or tumor cell death.

In some aspects, the SHLP administered to treat cancer according to a method provided herein is SHLP6 or a variant thereof. Somatic mutations (Ruiz-Pesini et al., Nucleic Acids Research, 35 (Database issue): D823-D828 (2007)) at several positions in and adjacent to the SHLP6 coding region (which was previously thought to be non-coding DNA) have been associated with prostate cancer (position 2923; Jeronimo et al., Oncogene, 20(37): 5195-5198 (2001)), lung cancer (position 2998; Lorenc et al., Mitochondrion, 3(2): 119-124 (2003)) and colon cancer (position 3014; Taylor et al., Journal of Clinical Investigation 112(9): 1351-1360 (2003)). These findings indicate that dysregulation of SHLP6 may be a key step in the development or progression of certain cancers. In further aspects, the SHLP is any of SHLPs 1-6 or a variant thereof.

The present invention also provides methods of treating a subject having a disorder characterized by aberrant activity and/or aberrant expression of an SHLP, SHLP nucleic acid, or variant thereof, by administering an agent which is a modulator of the activity of an SHLP or variant thereof or a modulator of the expression of an SHLP nucleic acid.

Also provided herein are pharmaceutical compositions comprising one or more SHLPs and at least one pharmaceutically acceptable carrier or excipient.

Nucleic acids, polypeptides, and antibodies ("active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The active ingredient of the pharmaceutical composition of the present invention may be DNA encoding the polypeptide of the present invention. When the DNA encoding the oligopeptide is used as a gene therapy agent for the disease described above, examples of administration methods thereof include a method which administers a vector incorporating the DNA therein. Examples of the vector include plasmids, adenovirus vectors, adeno-associated virus vectors, herpes virus vectors, vaccinia virus vectors, and retrovirus vectors. The therapeutic agent can be expressed in vivo with efficiency by infecting organisms with the viral vectors. Alternatively, a method which introduces the vector or the DNA into liposomes (e.g., positively charged liposomes and positively charged cholesterol) and administers the liposome can be used as an effective therapy.

When the pharmaceutical composition of the present invention is used as a preventive and/or therapeutic agent for the diseases described above, it can be administered to mammals such as humans, mice, rats, rabbits, dogs, and cats. The dose and number of doses of the pharmaceutical drug of the present invention may be changed appropriately according to the age, sex, and conditions of a subject to be administered, or administration routes.

A therapeutically effective amount of protein or polypeptide provided herein can range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Having now generally described various aspects and aspects of the invention, the same will be more readily understood through reference to the following examples which are provided by way of illustration, and are not intended to be limiting, unless specified.

EXAMPLES

Example 1

Expression patterns of SHLPs in vivo. To gain insights into the physiological roles of SHLPs, monoclonal antibodies were generated against SHLP2, SHLP3, and SHLP6 (Open Biosystems) and were used to assess expression patterns of the SHLPs across a variety of murine tissues. Male and female C57/Bl6 mice at 45 weeks of age were euthanized, and brain, liver, kidneys, heart, ovaries, skeletal muscle, breast, testes, prostate and pancreas tissues were harvested. SHLP expression levels in protein extracts isolated from the harvested tissues were measured immunologically using anti-SHLP antibodies. SHLPs were expressed in vivo according to the expression patterns summarized in table 7.

TABLE 7

| Endogenous SHLP expression | |
|---|---|
| Protein | Main Tissues of Expression |
| SHLP2 | Liver, kidney, pancreas, plasma |
| SHLP3 | Liver, kidney, heart, pancreas, plasma |
| SHLP6 | Prostate, testis, breast, brain |

Example 2

Figure 2:
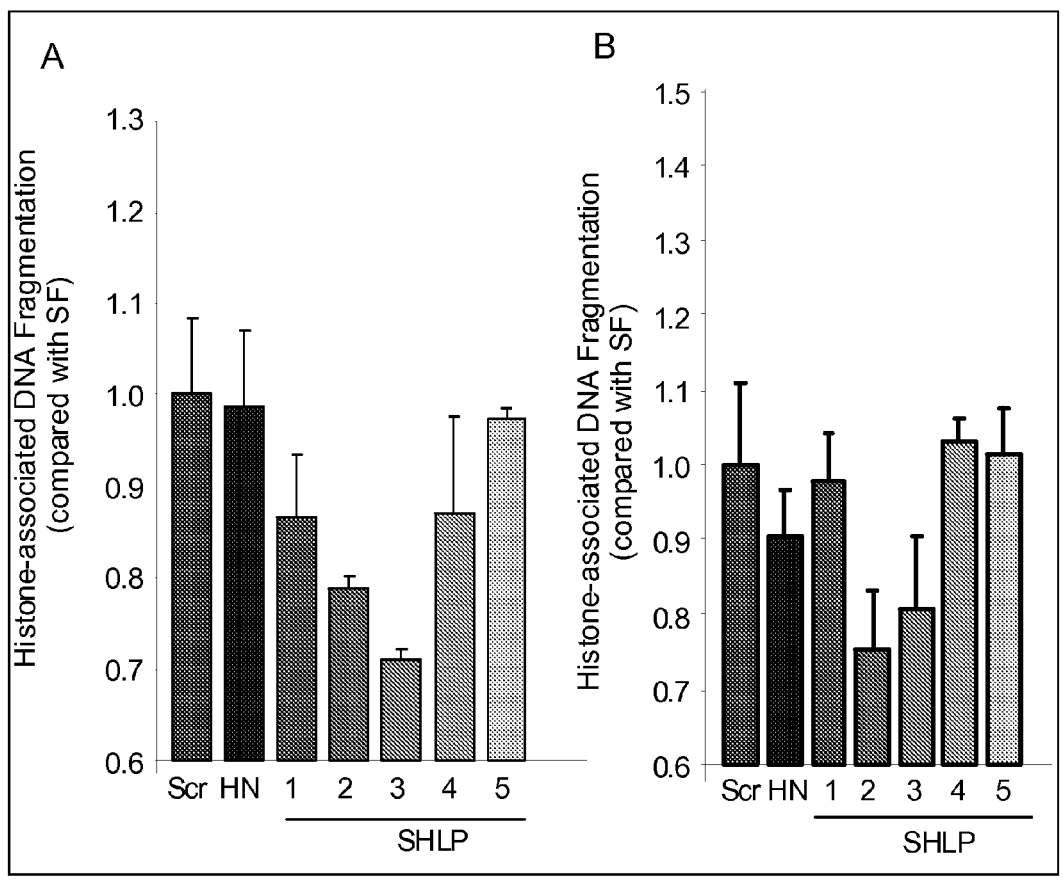
FIG. 2. SHLPs exert differential effects on apoptosis. 22RV1 (A) or NIT-1 (B) cells were incubated in SF media for 24 h followed by 24 h with 100 nM scrambled control (Scr) peptide, HN, or SHLP 1-5. Apoptosis was assessed by fragmentation of histone-associated DNA.

SHLPs are anti-apoptotic in 22RV1 prostate cancer cells and NIT-1 β-cells. Since HN has been shown to have anti-apoptotic actions in both cancer and pancreatic β-cells in vitro, it was hypothesized that SHLPs may also influence cell survival. Mouse NIT-1 insulinoma β-cells and 22RV1 human prostate cancer cells were serum starved for 24 h, followed by 24 h incubation with 100 nM scrambled control peptide, HN or SHLPs. Apoptosis was assessed and quantified by ELISA for fragmentation of histone-associated DNA. SHLPs exerted anti-apoptotic effects to varying effects in the two cell types (FIG. 2).

Example 3

Figure 3:
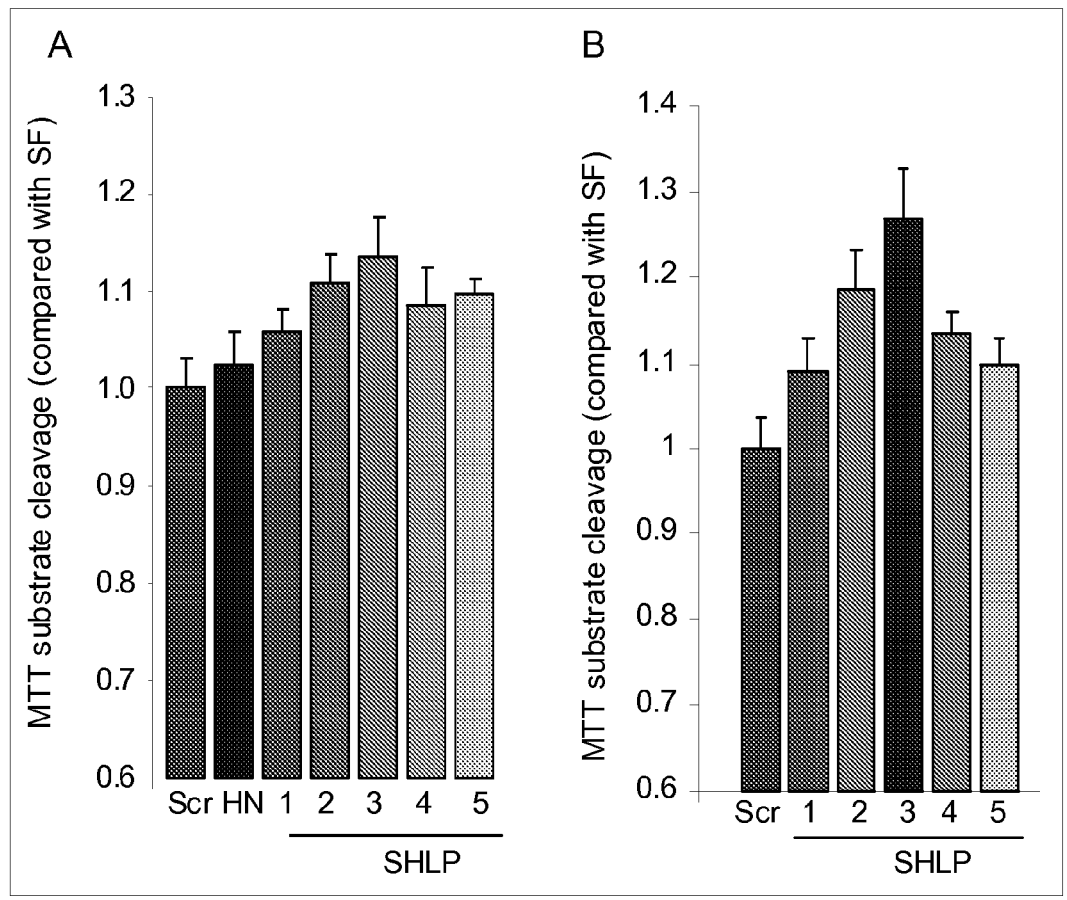
FIG. 3. SHLPs stimulate the proliferation of NIT-1 and 22RV1 cells. 22RV1 (A) or NIT-1 (B) cells were incubated in SF media for 24 h followed by 72 h with 100 nM scrambled control (Scr) peptide, HN, or SHLP 1-6. Cell number was assessed by cleavage of MTS substrate.

SHLPs exert distinct effects on cell proliferation. Whether SHLPs have the capacity to influence cell proliferation, in addition to their intrinsic effects on apoptosis induction, was also investigated. Mouse NIT-1 insulinoma β-cells and 22RV1 human prostate cancer cells were serum starved for 24 h, followed by 72 h incubation with 100 nM scrambled control peptide, HN or SHLPs. Cell number, as a measure of cell proliferation, was assessed by cleavage of MTT substrate. SHLPs 1, 4, and 5 slightly stimulated the proliferation of both cell types (FIGS. 3A&B). However, SHLPs 2 and 3 had a much greater effect, particularly in NIT-1 cells (FIG. 3B), suggesting that they may not only help protect β-cells from apoptotic cell death, but also stimulate their regeneration, indicating therapeutic potential in type I diabetes.

Example 4

SHLPs 2 and 3 Stimulate Adipocyte Differentiation of 3T3-L1 Cells in vitro. Our initial studies revealed that SHLPs can modulate the processes of cell proliferation and apoptosis. We next assessed the ability of SHLP2, 3 and 6 to modulate the differentiation of 3T3-L1 adipocytes. Differentiation was induced in murine 3T3-L1 fibroblasts by incubation in 1 µM dexamethasone, 100 nM insulin, and 500 µM lisobutyl-methyxanthine for 2 days, followed by incubation with 10 nM insulin in the presence of 100 nM scrambled peptide (control), SHLP2, SHLP3 or SHLP6 for 7 days. Differentiation was assessed by oil red-0 staining as a measure of oil droplet formation. Unlike SHLP6, SHLPs 2 and 3 strikingly induced adipocyte differentiation (FIG. 2), suggesting that MDPs can also affect cellular differentiation with direct relevance to type II diabetes.

Example 5

Figure 4:
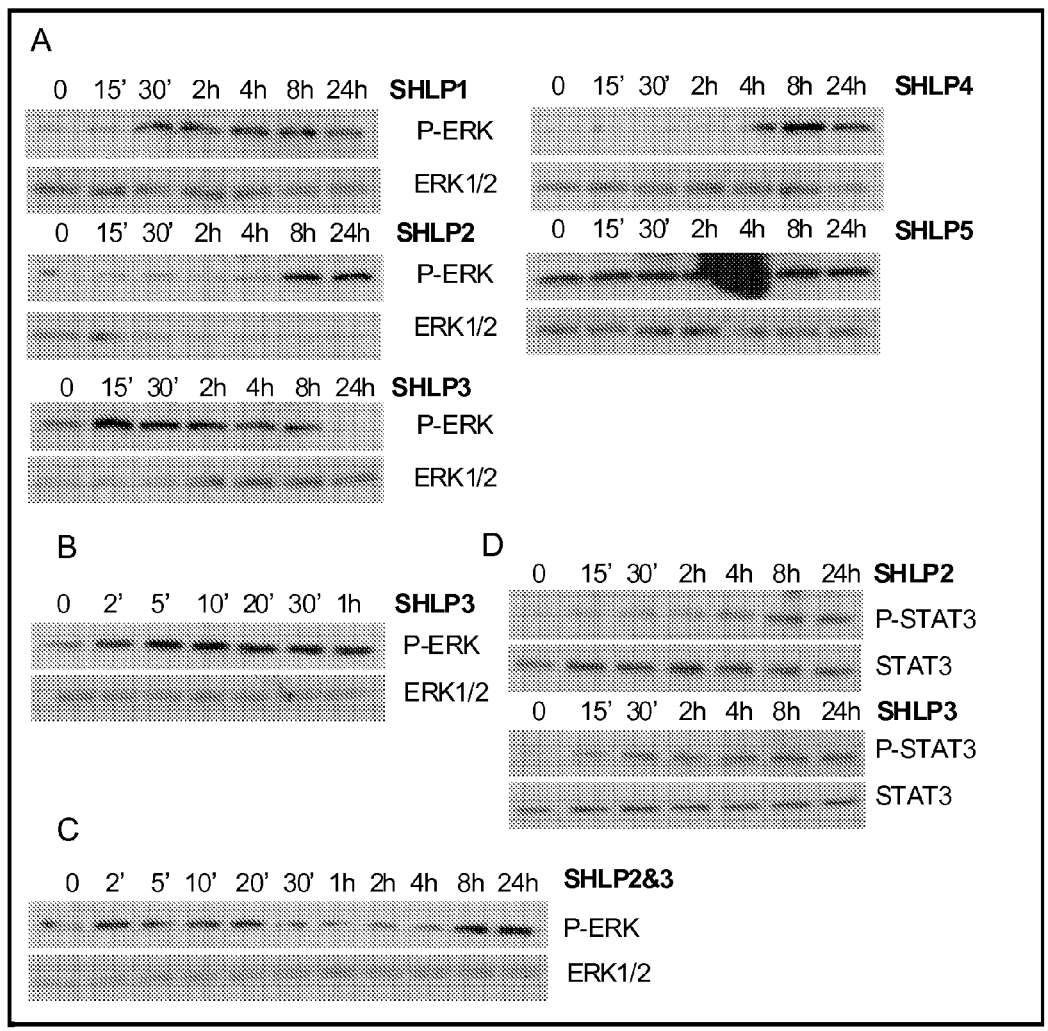
FIG. 4 ERK and STAT3 activation by SHLPs. 22RV1 cells were incubated in SF media for 24 h followed by treatment with 100 nM SHLP, as indicated. A-C, phospho and total ERK were assessed by immunoblotting. D, Phospho (Y305) and total STAT3 were assessed by immunoblotting.

Characterization of the intracellular signaling pathways activated by SHLPs. To determine a mechanism for the growth and apoptosis effects of SHLPs, SHLPs were tested for the ability to modulate activation of intracellular signaling pathways. 22RV1 cells in SF media were treated with 100 nM SHLP 1-5 and whole cell extracts were harvested after 15 min, 30 min, 2 h, 4 h, 8 h and 24 h. Proteins were separated by SDS-PAGE and analyzed by immunoblotting. Temporally distinct profiles for the activation of ERK were observed for each of SHLPs 1-5. SHLP1 caused a 5-fold increase in phosphorylation within 30 min, which was sustained for approximately 8 h, whereas SHLP2 caused a delayed but sustained activation after 8 h (FIG. 4A). SHLP3, in contrast, activated ERK rapidly within 2 min (FIG. 4B), but the degree of activation began to fall after 30 min and had returned to baseline by 8 h. SHLP4 displayed a similar activation profile to SHLP2, whilst SHLP5 had no observable effect on ERK phosphorylation.

To test the hypothesis that SHLPs may act in concert to regulate intracellular signaling, 22RV1 cells were co-treated with SHLPs 2 and 3, and ERK activation was assessed. Consistent with previous observations, results showed a "two-wave" activation—an immediate rapid phosphorylation, presumably corresponding to SHLP3, and a more delayed but sustained activation seemingly corresponding to SHLP2 (FIG. 4C).

Figure 5:
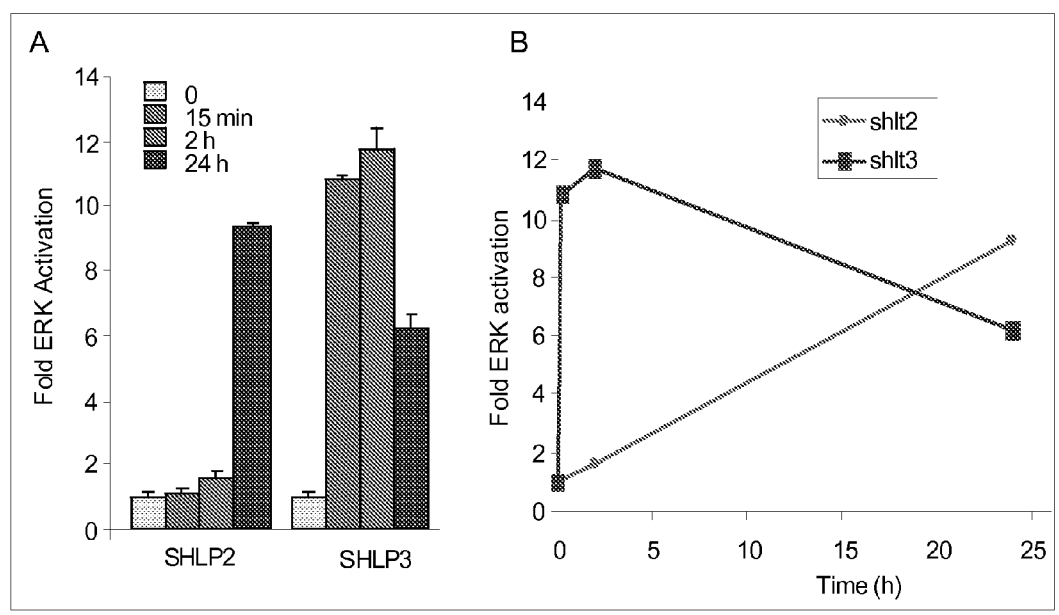
FIG. 5. ERK activation by SHLPs 2 and 3. 22RV1 cells were incubated in SF media for 24 h followed by treatment with 100 nM SHLP2 or 3 as indicated. Cell lysates were harvested at the indicated times, and ERK activation was assessed by ELISA, following manufacturer's instructions.

Since HN causes activation of STAT3, SHLPs 2 and 3 were also tested for effects on STAT3. Both peptides significantly enhanced STAT3 activation (FIG. 4D). To more accurately quantify the ERK phosphorylation caused by SHLPs 2 and 3, we repeated the experiment as described above but used a commercially available ERK ELISA to assess ERK phosphorylation. Optimal ERK activation by SHLP2 was 9-fold after 24 h, whilst optimal activation by SHLP3 was 12-fold after 2 h (FIG. 5).

Figure 6:
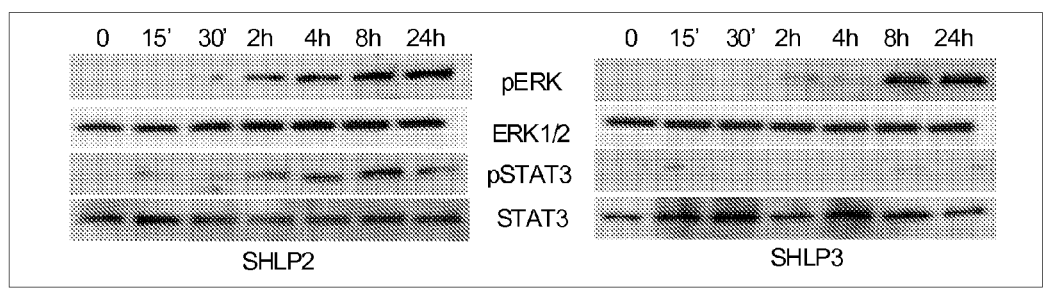
FIG. 6. Activation of ERK and STAT3 by SHLP2 and 3 in NIT-1 cells. NIT-1 cells were incubated in SF media for 24 h followed by treatment with 100 nM SHLP, as indicated. Phospho and total ERK, and phospho (Y305) and total STAT3 were assessed by immunoblotting.
Figure 7:
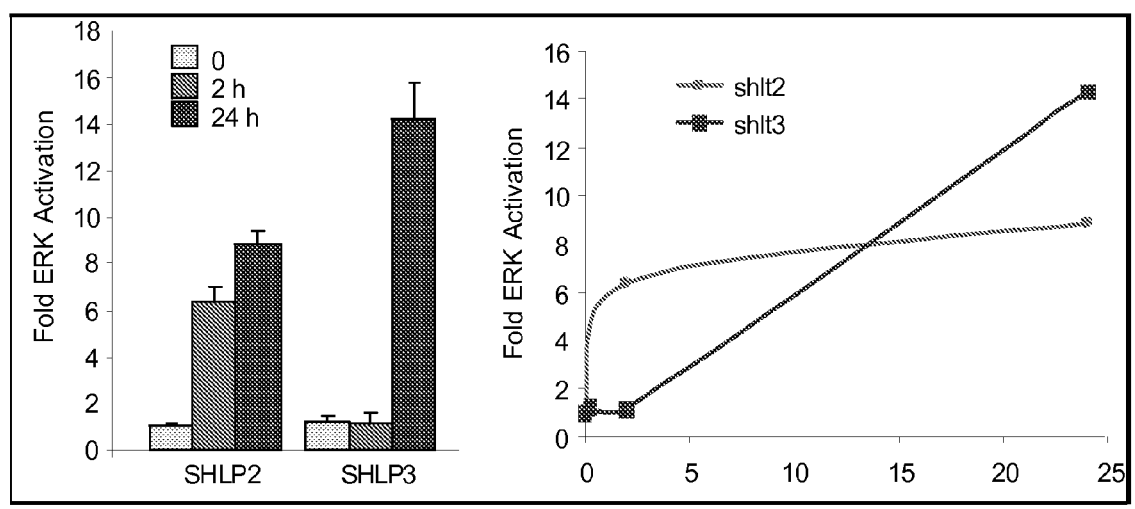
FIG. 7 Quantitation of ERK activation by SHLP2 and 3 in NIT-1 cells. NIT-1 cells were incubated in SF media for 24 h followed by treatment with 100 nM SHLP2 or 3 as indicated. Cell lysates were harvested at the indicated times, and ERK activation was assessed by ELISA, following manufacturer's instructions.

In addition to 22RV1, the effects of SHLPs on ERK and STAT3 phosphorylation were also studied in NIT-1 pancreatic β-cells. Interestingly, the activation profiles were different than those observed in 22RV1 cells. SHLP2-stimulated ERK phosphorylation was detected within 30 min, and the intensity continued to increase until 24 h (FIG. 6). In contrast, SHLP3 caused a more delayed response, which stimulated ERK phosphorylation by 8 h and sustained the stimulation for 24 h. Indeed, the activation profile caused by SHLP3 in NIT-1 is remarkably similar to that stimulated by SHLP2 in 22RV1. When ERK activation was quantified by ELISA, a 6-fold and 9-fold activation was observed after 2 and 24 h, respectively, by SHLP2. SHLP3 caused no detectable increase in ERK phosphorylation after 2 h, but by 24 h had stimulated activity 15-fold (FIG. 7). Similarly, STAT3 activation by SHLP2 was temporally similar to the timing of ERK activation observed after SHLP2 treatment. In contrast, SHLP3 appeared to only slightly stimulate STAT3 phosphorylation (FIG. 6).

The distinct actions of SHLPs in different cell systems indicates that SHLPs may have tissue-specific effects, suggests that different receptors and/or different binding partners may be present in various cell and/or tissue types.

Example 6

Figure 8:
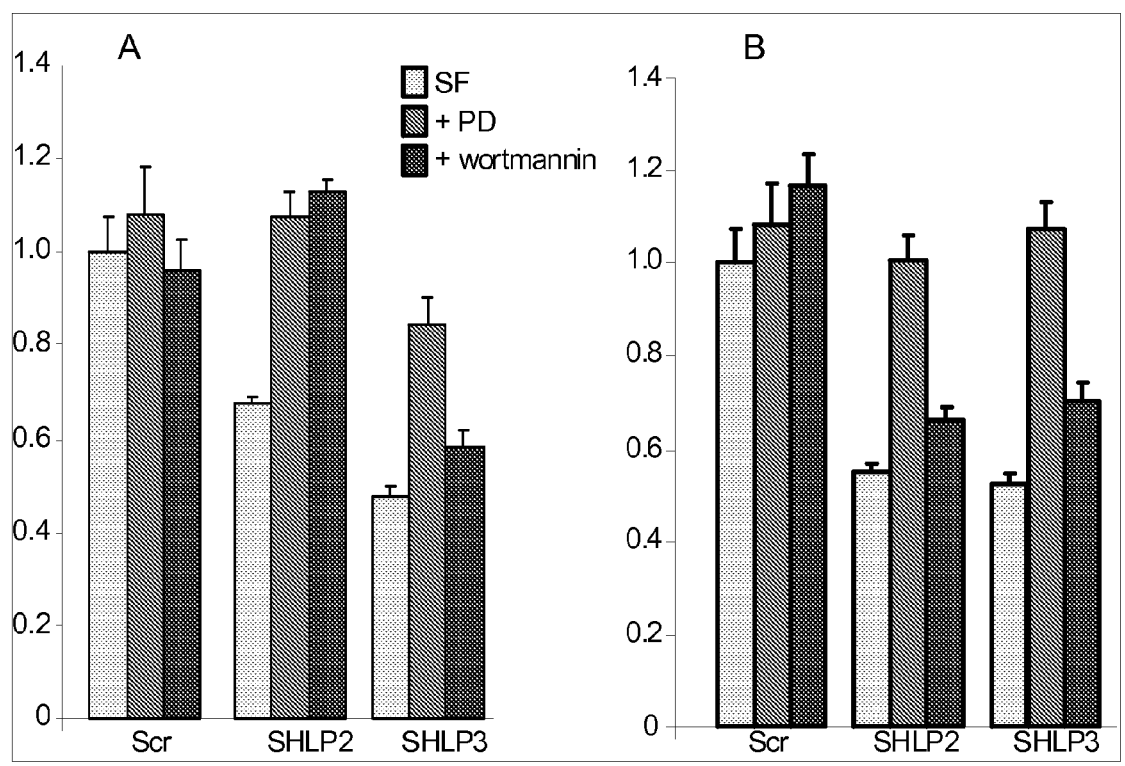
FIG. 8 Apoptosis inhibition by SHLP2 and 3 requires ERK activation in 22RV1 and NIT-1 cells. 22RV1 (A) or NIT-1 (B) cells were incubated in SF media±25 µM PD98059 or 1 µM wortmannin for 24 h followed by 24 h with 100 nM scrambled control (Scr) peptide, SHLP2 or SHLP3. Apoptosis was assessed by fragmentation of histone-associated DNA.

ERK activation is necessary for SHLP-induced inhibition of apoptosis in NIT-1 and 22RV1 cells. To determine the significance of ERK activation for apoptosis inhibition by SHLPs 2 and 3, PD98059 (PD), a specific chemical inhibitor of ERK1/2, was utilized. 22RV1 and NIT-1 cells were serum starved for 24 h in the presence or absence of 25 µM PD or 1 µM wortmannin (PI3-kinase inhibitor; negative control), followed by 24 h incubation with 100 µM scrambled control peptide, SHLP2 or SHLP3. Apoptosis was then assessed by ELISA for fragmentation of histone-associated DNA. As expected, apoptosis was significantly inhibited by SHLP2 and 3 in both 22RV1 and NIT-1 cells. However, pre-treatment with PD98059 abrogated the affects of both SHLPs 2 and 3, indicating that ERK activation is necessary for or facilitates the inhibitory effects of each (FIG. 8). Interestingly, pre-treatment with wortmannin in 22RV1 cells also inhibited SHLP2-induced cell survival, suggesting that SHLP2 activated a PI3-kinase-ERK signalling cascade in this cell system, but not in NIT-1 cells. Overall, these data support a protective role for SHLPs on beta cells in a manner that is relevant to type-1 diabetes.

Example 7

Figure 9:
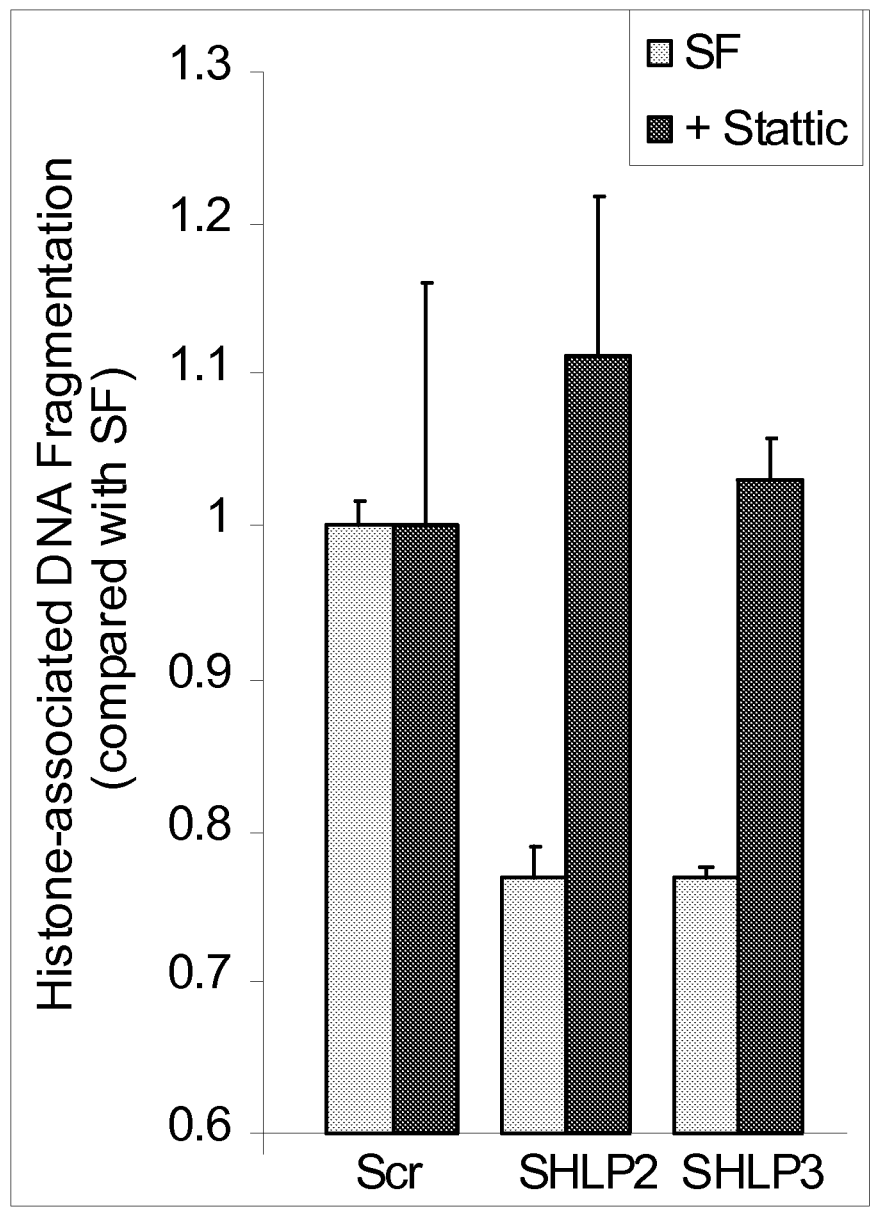
FIG. 9 STAT3 activation is necessary for SHLP-induced cell survival in 22RV1 cells. 22RV1 cells were incubated in SF media±20 µM stattic for 24 h followed by 24 h with 100 nM scrambled control (Scr) peptide, SHLP2 or SHLP3. Apoptosis was assessed by fragmentation of histone-associated DNA.

STAT3 Activation is also necessary for SHLP-induced cell survival in 22RV1 cells. Since SHLPs 2 and 3 both stimulate STAT3 phosphorylation in addition to ERK activation, the hypothesis that STAT3 activation occurs downstream of ERK1/2 was tested using a specific chemical inhibitor against STAT3, stattic. 22RV1 cells were incubated for 24 h in SF media in the presence or absence of 20 µM stattic followed by 24 h incubation with 100 nM scrambled control peptide, SHLP2 or SHLP3. Apoptosis was assessed by ELISA for fragmentation of histone-associated DNA. Pre-treatment with STAT3 inhibitor abrogated the protective effects of both SHLPs (FIG. 9). These data suggest that both ERK and STAT3 activation are necessary for SHLP-induced inhibition of apoptosis, suggesting that STAT3 is downstream of ERK in the signaling cascades activated by SHLPs 2 and 3.

Example 8

Figure 10:
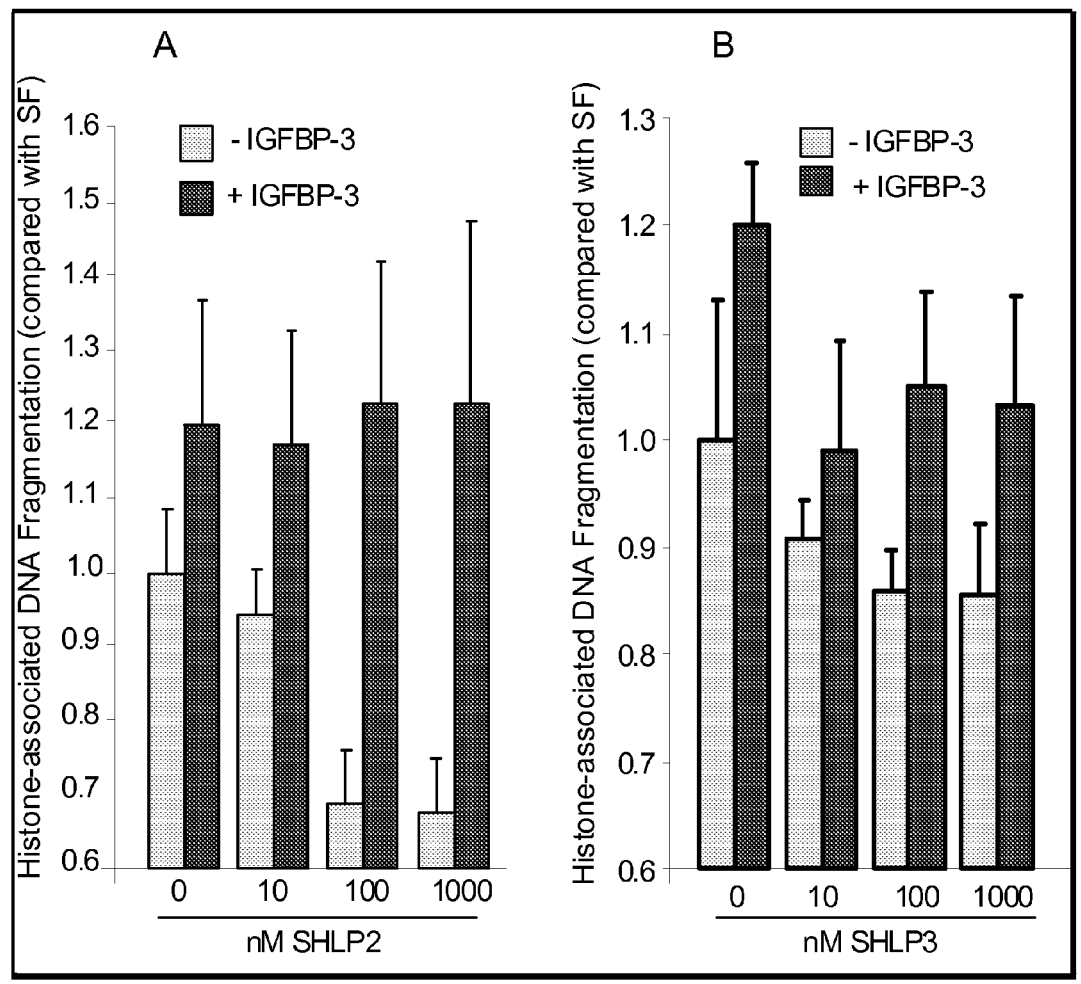
FIG. 10 Effects of co-treatment with IGFBP-3 and SHLPs on apoptosis induction in NIT-1 cells. NIT-1 cells were incubated in SF media for 24 h followed by treatment with 1 µg/ml IGFBP-3±SHLP2 or 3 as indicated for 24 h. Apoptosis was assessed by ELISA for fragmentation of histone-associated DNA FIG. 11 Co-treatment with SHLP combinations leads to change of function in 22RV1 and NIT-1 cells. 22RV1 (A) and NIT-1 (B) cells were incubated in SF media for 24 h, followed by 24 h with 100 nM HN±SHLPs as indicated. Apoptosis was assessed by ELISA for fragmentation of histone-associated DNA.

Role of IGFBP-3 in effects of SHLPs on cell survival. Since IGFBP-3 is an important regulator of HN action, IGFBP-3 was tested for a possible role in regulating the anti- or pro-apoptotic actions of SHLPs. NIT-1 cells were incubated with 1 µg/ml IGFBP-3±0, 10, 100 or 1000 nM SHLP2 or 3 for 24 h. Apoptosis induction was assessed by ELISA for fragmentation of histone-associated DNA. As expected, incubation of NIT-1 cells with IGFBP-3 led to the induction of apoptosis. Incubation with SHLP2 led to a dose dependent inhibition of apoptosis that was unaffected by the presence of IGFBP-3 (FIG. 10A). Although treatment with SHLP led to reduced levels of apoptosis, interestingly SHLP3 demonstrated the ability to inhibit IGFBP-3-induced apoptosis (FIG. 10B), suggesting a possible interaction with the IGF system.

Example 9

Figure 11:
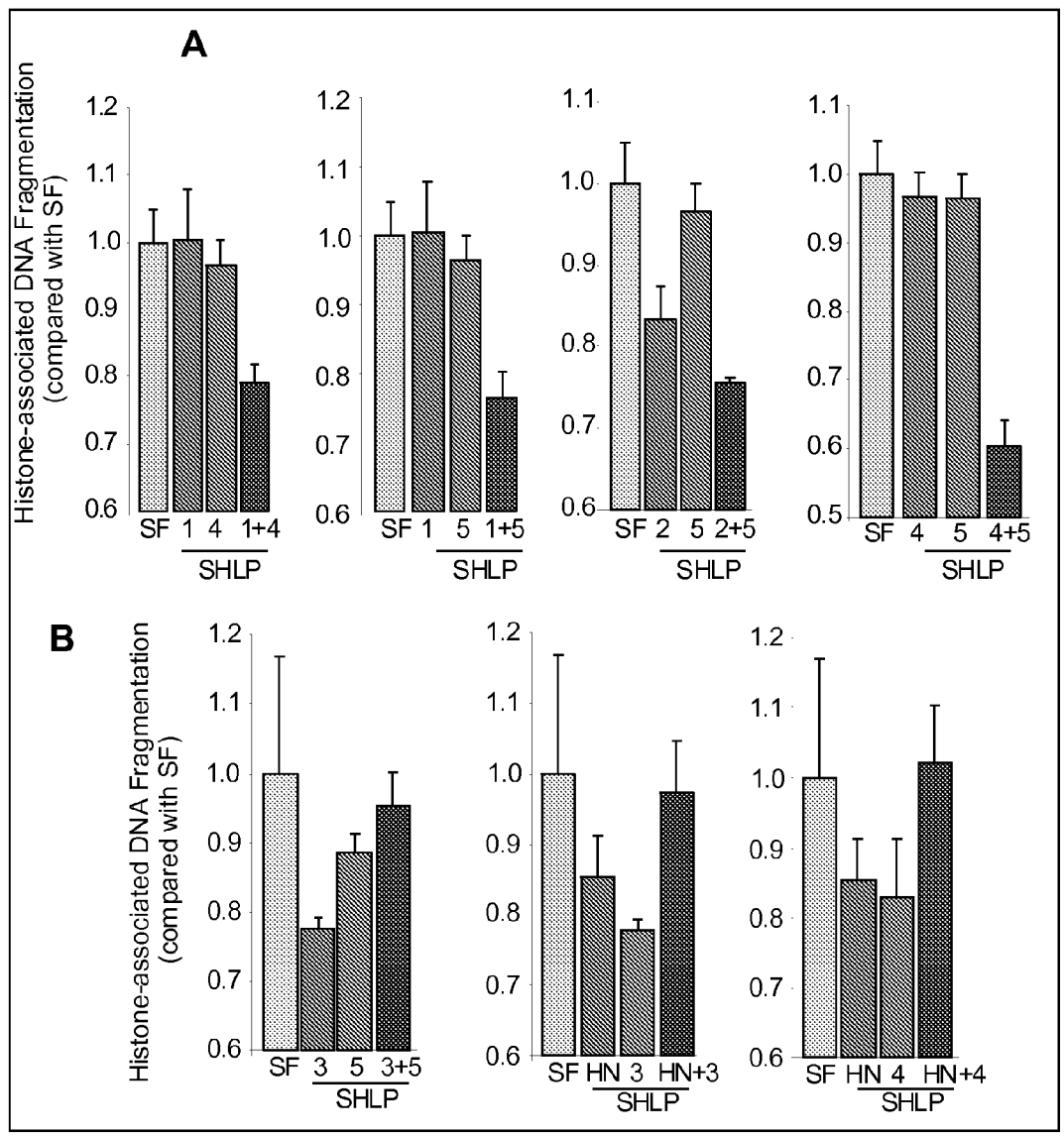

Co-incubation of SHLPs. To evaluate therapeutic uses involving co-treatment with SHLPs, the effect of HN±SHLPs on apoptosis was tested in both 22RV1 and NIT-1 cells. Cells were incubated in SF media for 24 h followed by 24 h with 100 nM HN, SHLP or peptide combination. Apoptosis was assessed by ELISA for fragmentation of histone-associated DNA. Cells were treated with all possible double peptide combinations. Although many peptide combinations had no additive or combined effects compared with the actions of the peptides individually, co-treatment with certain combinations led to unexpected functional changes (FIG. 11). For example, treatment with SHLPs 1&5, or 4&5 individually had minimal effect of survival in 22RV1 cells (FIG. 11A). However, when added together, the peptides potently promoted cell survival. Thus, specific SHLPs may either act on complementary pathways, or interact with each other, leading to change of function of one or both peptides. When the same experiments were repeated in NIT-1 cells, similar, but different, change of function effects were observed (FIG. 11B). For example, the addition of HN with either SHLP3 or 4 led to blocking of the anti-apoptotic effects observed with either peptide individually.

Figure 12:
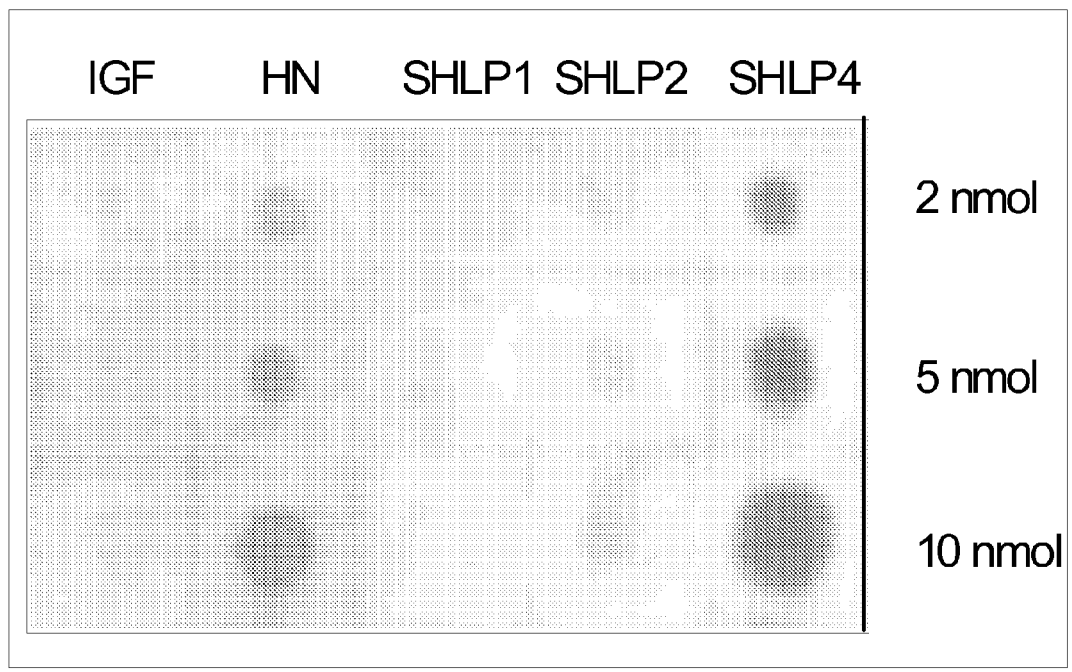
FIG. 12 HN binds to SHLP2 and SHLP4. 2, 5 and 10 nmol of IGF-1 (negative control), HN, SHLP1, 2 or 4 were dotted on to nitrocellulose membrane and left to dry. The membrane was blocked, incubated with biotinylated-HN and streptavidin-HRP and exposed by autoradiography.

To test a dimerization hypothesis, we performed a dot-blot using biotinylated-HN. Two, 5 or 10 nmol IGF-I (negative control), HN (positive control) or SHLP peptide were dotted on to nitrocellulose membrane, and their ability to bind to biotinylated-HN was assessed immunologically. HN was observed to dimerize/multimerize with itself. In addition, although no interaction was observed between HN with SHLP1, weak interaction was seen with SHLP2, and seemingly very strong interactions was seen between HN and SHLP4 (FIG. 12). These data suggest that interactions may occur between SHLPs and/or HN. Specific interactions that occur may be determined using, e.g., dot blots with biotinylated SHLPs, and/or antibodies against specific SHLPs.

Example 10

Figure 13:
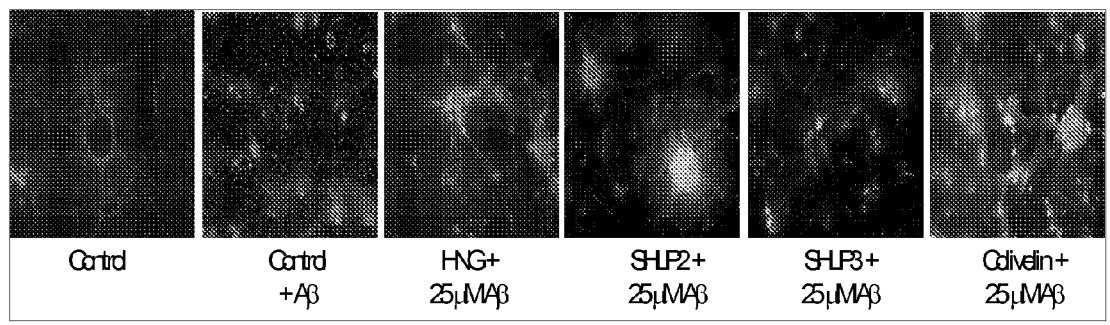
FIG. 13 SHLPs 2 and 3 function as neuro-protective factors. Murine primary cortical neurons were incubated for 72 h with 25 µM Aβ1-43 in the presence or absence of 100 nM HNG, SHLP2, SHLP3 or 10 nM colivelin. Neuronal viability was observed by fluorescence microscopy after Calcein-AM staining FIG. 14 SHLPs 2 and 3 enhance yeast survival against heat shock. S. cerevisiae was incubated in reducing concentrations with HN or SHLPs as indicated. The ability of yeast to survive heat shock at 60 and 90° C. were compared.

SHLPs protect neurons from Aβ-induced apoptosis. When it was first discovered, HN was described as a potent neural survival factor with clinical implications as a therapeutic agent against neurodegenerative diseases such as Alzheimer's Disease. Since many of the SHLPs appear to be functionally related to HN, SHLPs were tested as potential neuroprotective factors. Mouse primary cortical neurons were incubated with 25 µM Aβ1-43 in the presence or absence of 100 nM SHLP2 or 3, HNG (positive control) or 1 nM colivelin (positive control). After 72 h, neuronal viability was assessed by Calcein-AM staining followed by fluorescence microscopy (FIG. 13). Incubation of neurons with Aβ led to dramatic cell death which could be inhibited by incubation with the hyper-potent HN analog HNG ($3^{rd}$ panel) or the highly potent HN-derivative colivelin ($6^{th}$ panel). SHLP2 and SHLP3 both demonstrated an ability to protect the neurons from the cell death caused by Aβ-treatment.

Example 11

Figure 14:
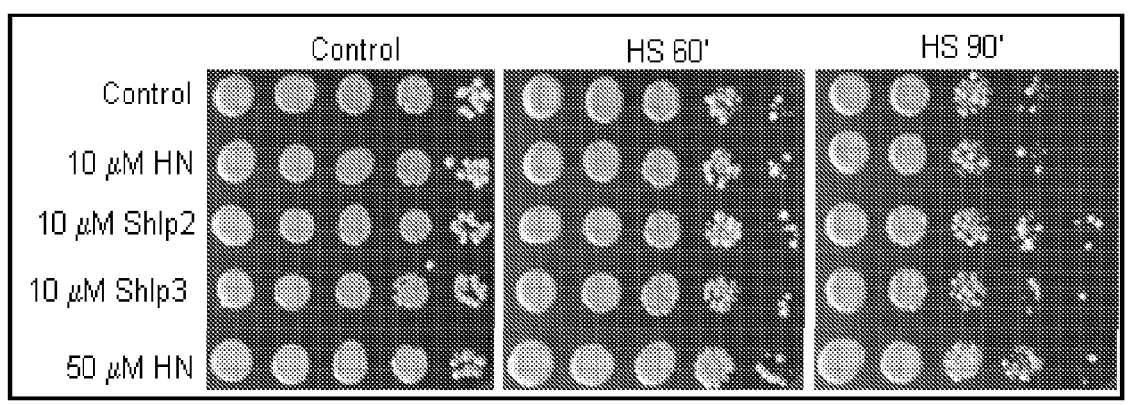
Figure 15:
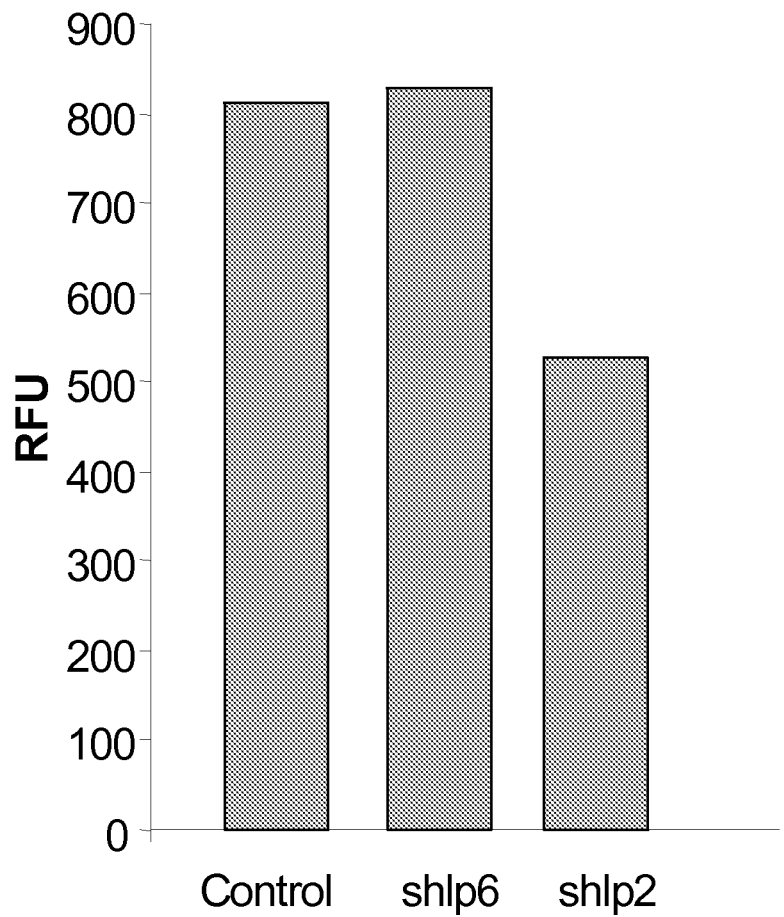
FIG. 15. SHLP2 suppresses production of reactive oxygen species (ROS).
Figure 16:
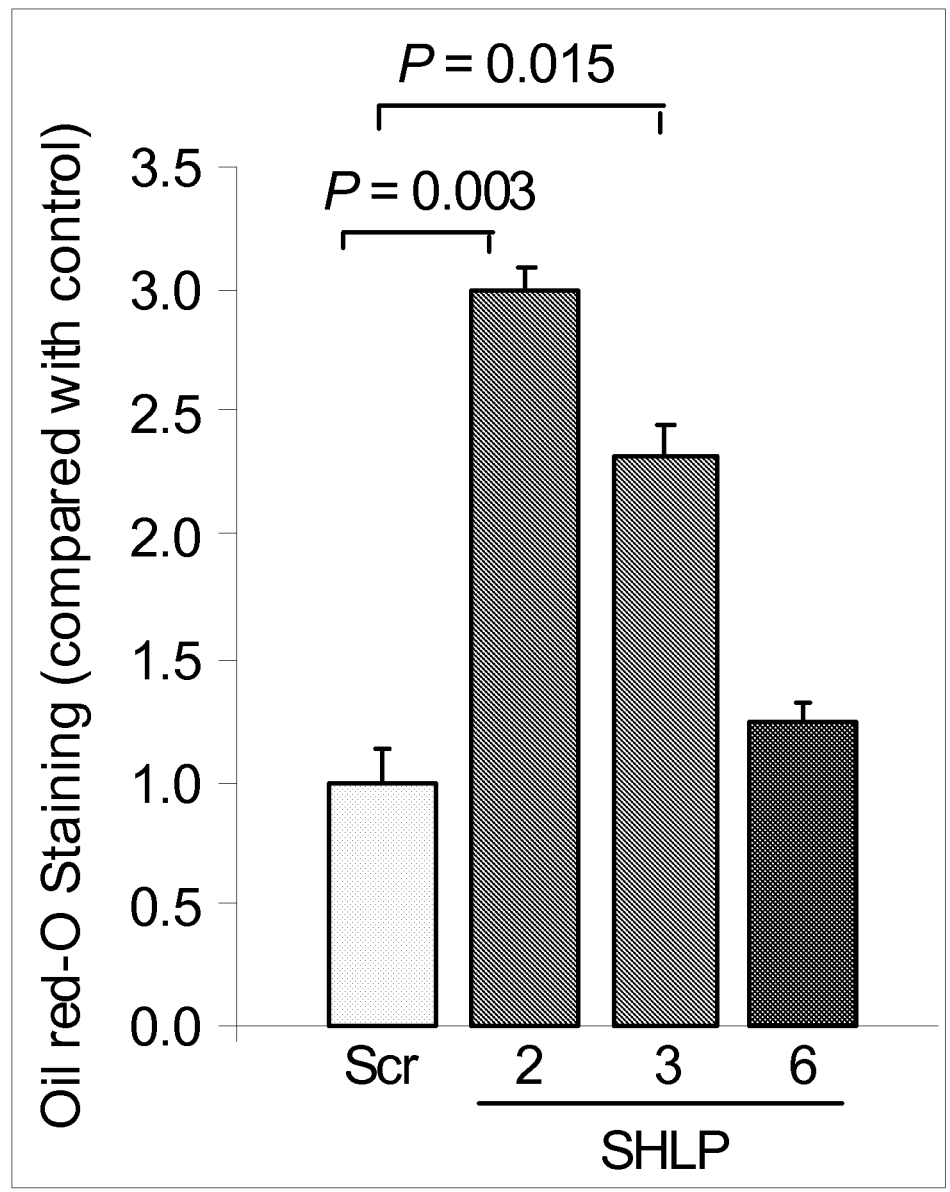
FIG. 16. SHLP2 and 3 stimulate 3T3-L1 adipocyte differentiation. 3T3-L1 adipocytes were incubated with 100 nM scrambled (control) peptide, SHLP2, 3 or 6 for 7 days, and differentiation was assessed by oil red-O staining. Staining intensity was quantified; n=3.
Figure 17:
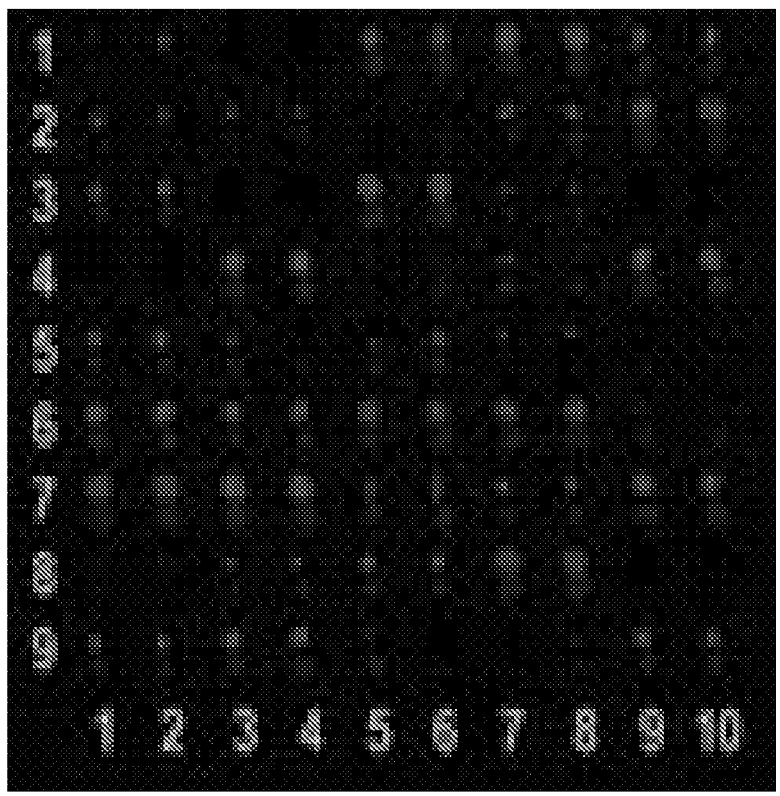
FIG. 17. Analysis of cellular markers affected by SHLP6 treatment. Cells were incubated in SF media for 24 h followed by treatment with 1 µM SHLP6 for 2 h. Cell lysates were harvested and hybridized to an antibody microarray (Kinexus), a panel of which is shown. Red indicates SHLP6-treated and blue control.
Figure 18:
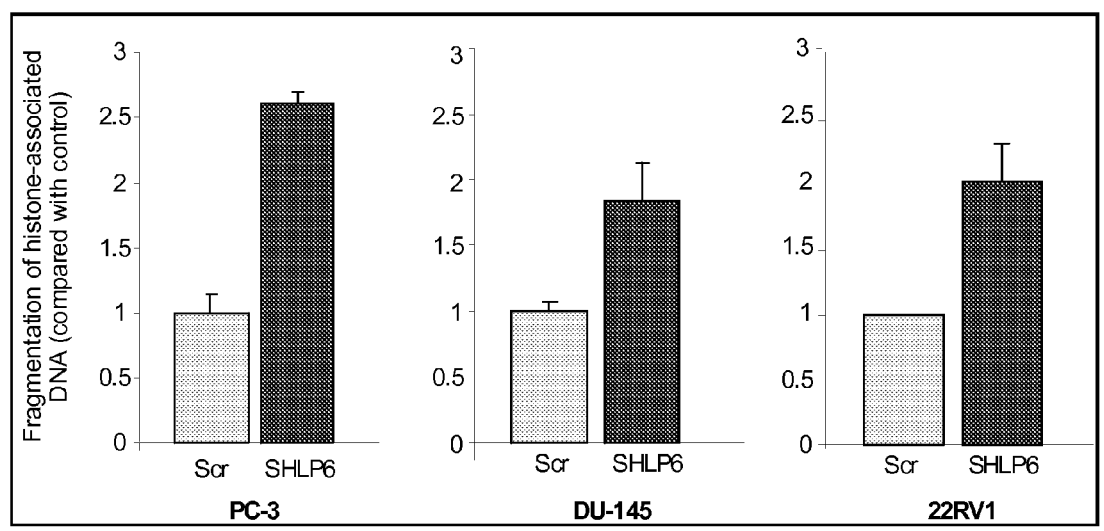
FIG. 18. SHLP6 is a potent inducer of apoptosis in prostate cancer cells in vitro. PC-3, DU-145 or 22RV1 cells were incubated in SF media for 24 h followed by 24 h with 1 µM scrambled control (Scr) peptide or SHLP6. Apoptosis was assessed by fragmentation of histone-associated DNA FIG. 19. SHLP6 has a variable effect on prostate cancer cell proliferation. DU-145, LAPC4, LNCaP, 22RV1 or PC-3 cells were incubated in SF media for 24 h followed by 72 h with 1 µM scrambled control (Scr) peptide or SHLP6. Cell number was assessed by cleavage of MTS substrate FIG. 20. SHLP6 increases tumor apoptosis, and decreases tumor angiogenesis and proliferation. Harvested tumors were stained by immunohistochemistry for TUNEL (apoptosis), VEGF (angiogenesis) and PCNA (proliferation) after 1 week treatment with SHLP6.

SHLPs enhance stress resistance in yeast. The ability of SHLPs to enhance stress resistance in yeast was tested. The ability of yeast to survive heat shock after being treated with different peptides is a commonly used method to test the ability of peptides to enhance yeast survival. However, few factors have been demonstrated to be protective in this regard, and many growth factors actually have the opposite effect. Treatment with 10 µM of HN SHLP2 or 3 allowed the yeast to withstand 90° heat shock (FIG. 14), suggesting that the SHLPs and or humanin may have protective effects atypical of common growth factors—this unexpected property suggests that SHLPs would be useful in cancer therapy.

Example 12

SHLPs suppress intracellular production of Reactive Oxygen Species (ROS). ROS production was monitored by following the conversion of the oxidant-sensitive dye dihydroethidine to the fluorescent ethidium (DHE) for measuring the cellular ability to produce Reactive Oxygen Species. HAEC'S plated on glass cover slips were incubated over night with 0.1 nM SHLP2 or SHLP6 versus regular cultured medium. For ROS measurement, cells were incubated for 30 min with 10 µM DHE in HBSS containing calcium magnesium and glucose at 37° c. Then cells were treated with Oxidized LDL 100 µg protein/ml for 30 minutes at 37° c. Samples were imaged under fluorescence microscope with a Texas Red filter corresponding to the fluorescence of DHE. Average fluorescence intensity was used to evaluate the changes of intracellular ROS generation, results are expressed in relative fluorescence unit (RFU) representing average intensity per cell area. SHLP2 suppresses ROS production, providing additional evidence that it protects against oxidative stress.

Example 13

Pro-apoptotic effect on human prostate cancer cells in vitro. To assess the ability of SHLP6 to induce apoptosis in human prostate cancer cells, PC-3, 22RV1 or DU145 cells were incubated in serum free (SF) media for 24 h followed by 24 h incubation with 1 µM scrambled (control) peptide or SHLP6. Apoptosis was assessed by ELISA for fragmentation of histone-associated DNA. In each cell line tested, SHLP6 induced apoptosis by at least 2-fold (FIG. 2), confirming highly significant physiological effects of this novel peptide. To determine whether the effects of SHLP6 were specific to induction of apoptosis, or if it also elicited growth-inhibitory effects, PC-3, DU-145, 22RV1, LAPC4 and LNCaP cells were incubated in SF media for 24 h followed by 72 h incubation with 1 µM SHLP6. Cell number, as a measure of cell proliferation, was assessed by cleavage of MTS substrate. Interestingly, SHLP6 only had an anti-proliferative effect in LAPC4 cells (FIG. 3), suggesting that its effects are influenced by p53, AR or PTEN status, or a combination of the three, and that its predominant anti-cancer effects involve induction of apoptosis, as opposed to inhibition of cell proliferation.

Example 14

Pro-apoptotic and anti-proliferative effects on human breast cancer cells in vitro. To assess the ability of SHLP6 to induce apoptosis in human breast cancer cells, we incubated MCF-7 cells in serum free (SF) media for 24 h followed by 24 h incubation with 1 µM scrambled (control) peptide or SHLP6. Apoptosis was assessed by ELISA for fragmentation of histone-associated DNA. SHLP6 potently induced apoptosis, confirming highly significant physiological effects of this novel peptide (FIG. 5A). To determine whether the effects of SHLP6 were specific to induction of apoptosis, or if it also elicited growth-inhibitory effects, we incubated MCF-7 cells in SF media for 24 h followed by 72 h incubation with 1 µM SHLP6 or control peptide. Cell number, as a measure of cell proliferation, was assessed by cleavage of MTS substrate. SHLP6 also inhibited proliferation (FIG. 5B), suggesting that its predominant anti-cancer effects involve both the induction or apoptosis and inhibition of cell proliferation.

Example 15

Figure 20:
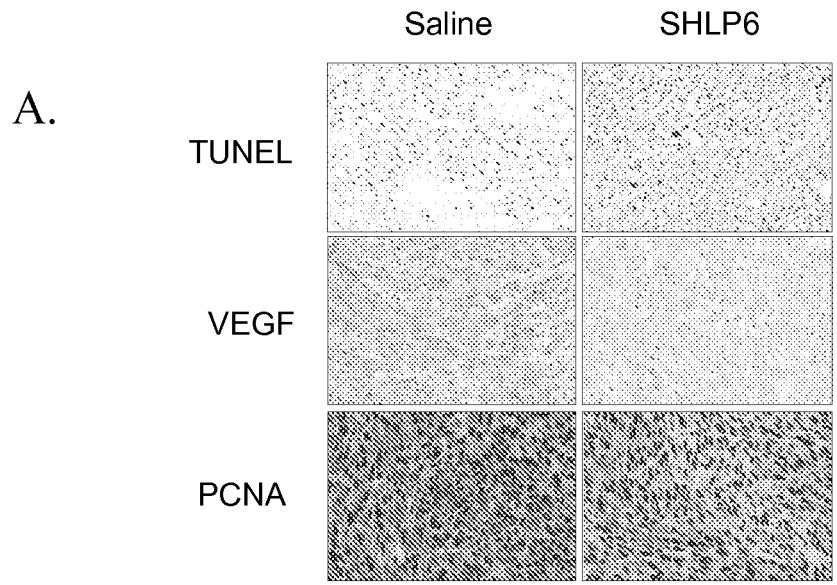
Figure 20:
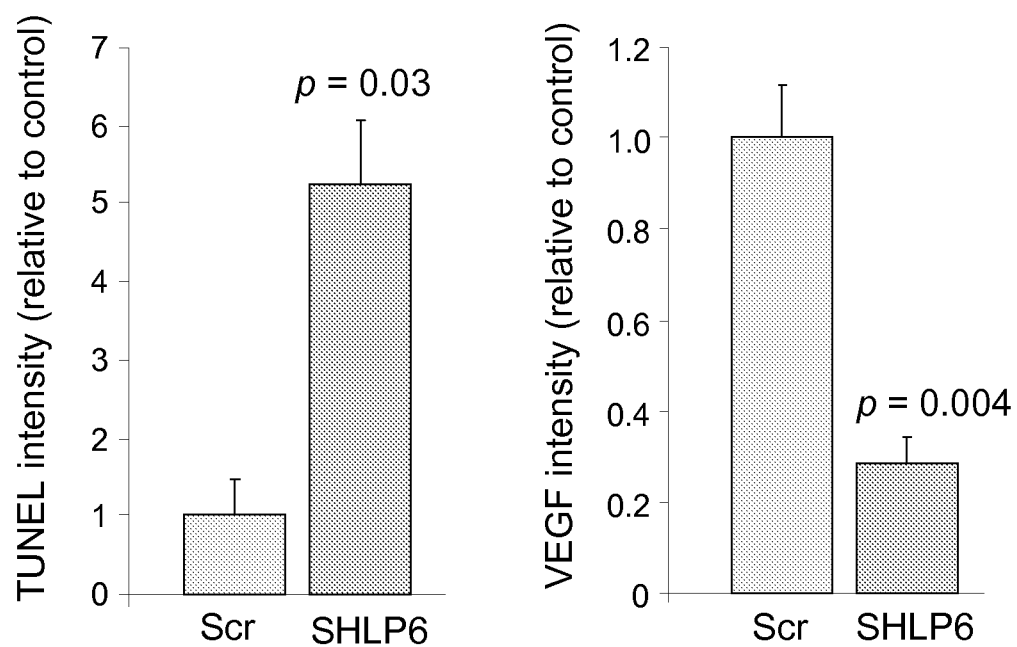

Inhibition of 22RV1 xenograft tumor growth and angiogenesis in vivo. In light of the pro-apoptotic actions of SHLP6 in vitro and the association of many cancers with mitochondrial dysfunction, the effect of SHLP6 on tumor growth was investigated in vivo. SCID mice harboring 22RV1 prostate cancer xenografts were treated with 4 mg/kg/day SHLP6 or scrambled control peptide by daily i.p. injection for 7 days. Subjects exhibited no detectable signs of toxicity. Remarkably, considering the relatively short-term of treatment, tumors injected with SHLP6 were found to be significantly (~30%) smaller than control tumors (p=0.04; FIG. 20). The findings provides direct, in vivo evidence that SHLP6 is capable of reducing tumor size and volume (not shown).

Figure 19:
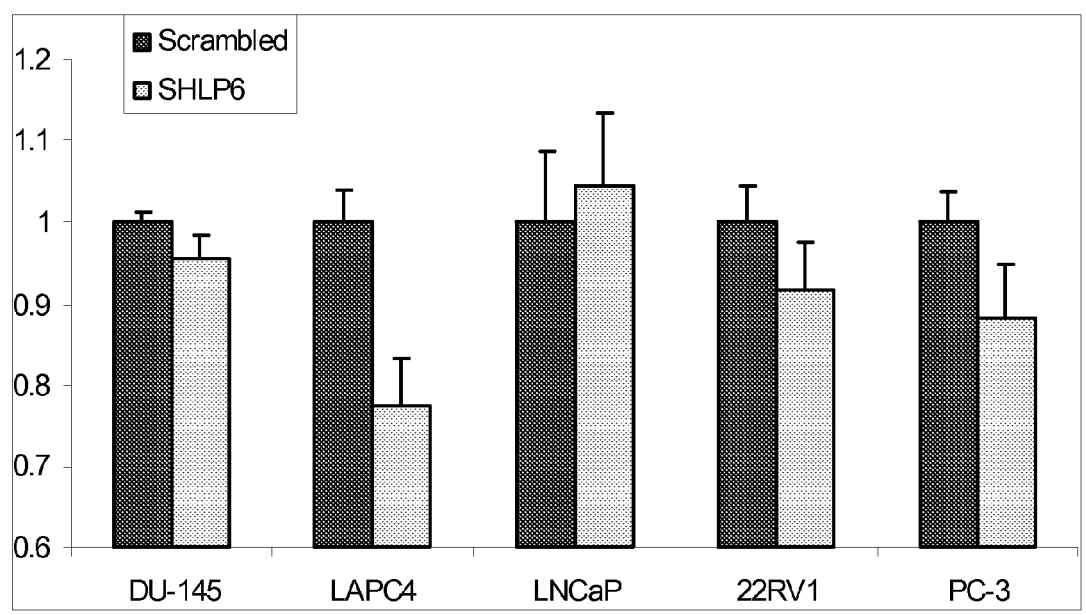

To assess the mechanism underlying the reduction in tumor growth, tumor apoptosis (TUNEL), angiogenesis (VEGF) and tumor cell proliferation (PCNA; not shown) were assessed by IHC (FIG. 19). Tumors treated with SHLP6 exhibited increased apoptosis, decreased angiogenesis and reduced proliferation, indicating that SHLP6 acts via multiple mechanisms to inhibit tumor growth. SHLP6 therefore has great potential as an anti-cancer agent.

The anticancer activity of SHLP6 is confirmed and further elucidated by conducting immunohistochemical analyses of xenograft tumors for angiogenic, apoptotic and proliferative markers, and by analyzing serum factors, including IGF-1, HN, GH and IGFBP-3.

Example 16

Figure 21:
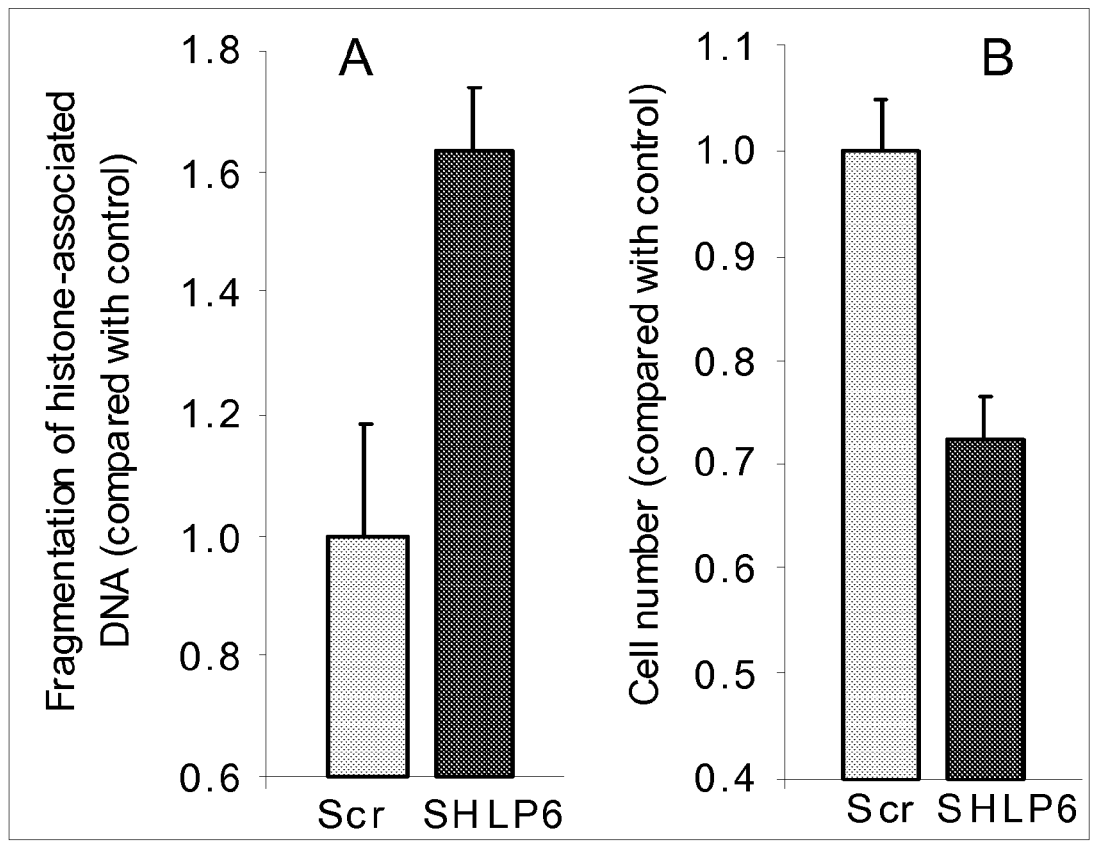
FIG. 21. SHLP6 is a potent apoptosis-inducer and growth-suppressor in breast cancer cells in vitro. A, Apoptosis was assessed in MCF-7 cells after 24 h incubation with 1 µM scrambled control (Scr) peptide or SHLP6. B, MCF-7 cells were incubated in SF media for 24 h followed by 72 h with SHLP6 or control FIG. 22. Reduction of tumor size and volume in mice i.p. injected with SHLP6. 22RV1 Xenografts were given daily i.p. injection with 4 mg/kg/day SHLP6 or scrambled control peptide for 7 days. Tumor volume was measured daily (A), and tumors were weighed at the end of the treatment period (B).
Figure 22:
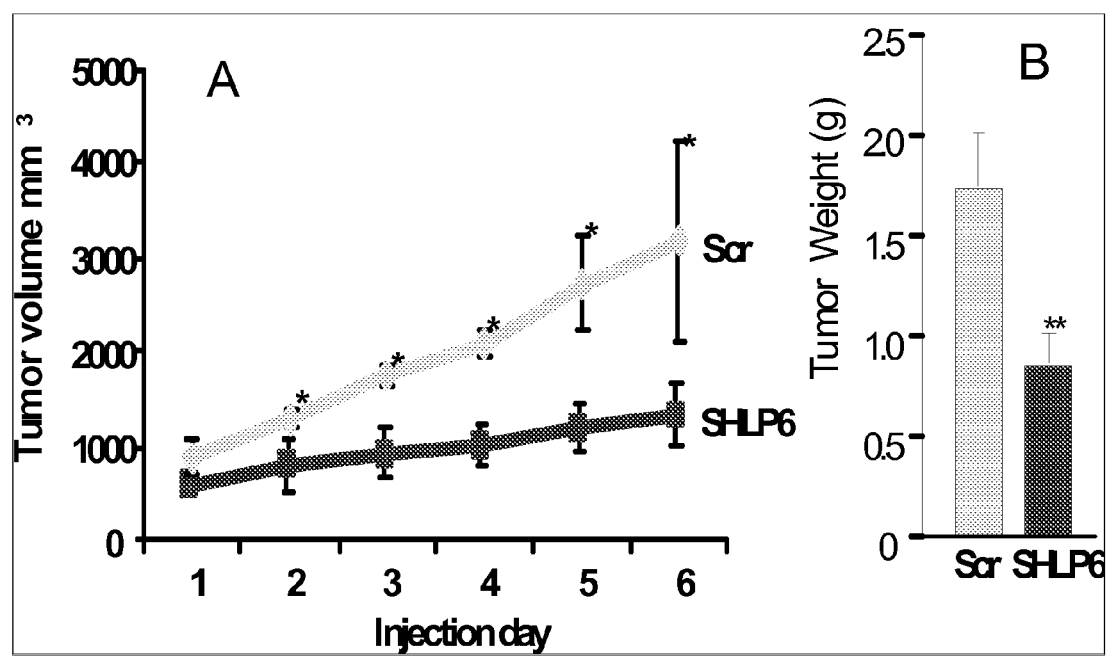
Figure 23:
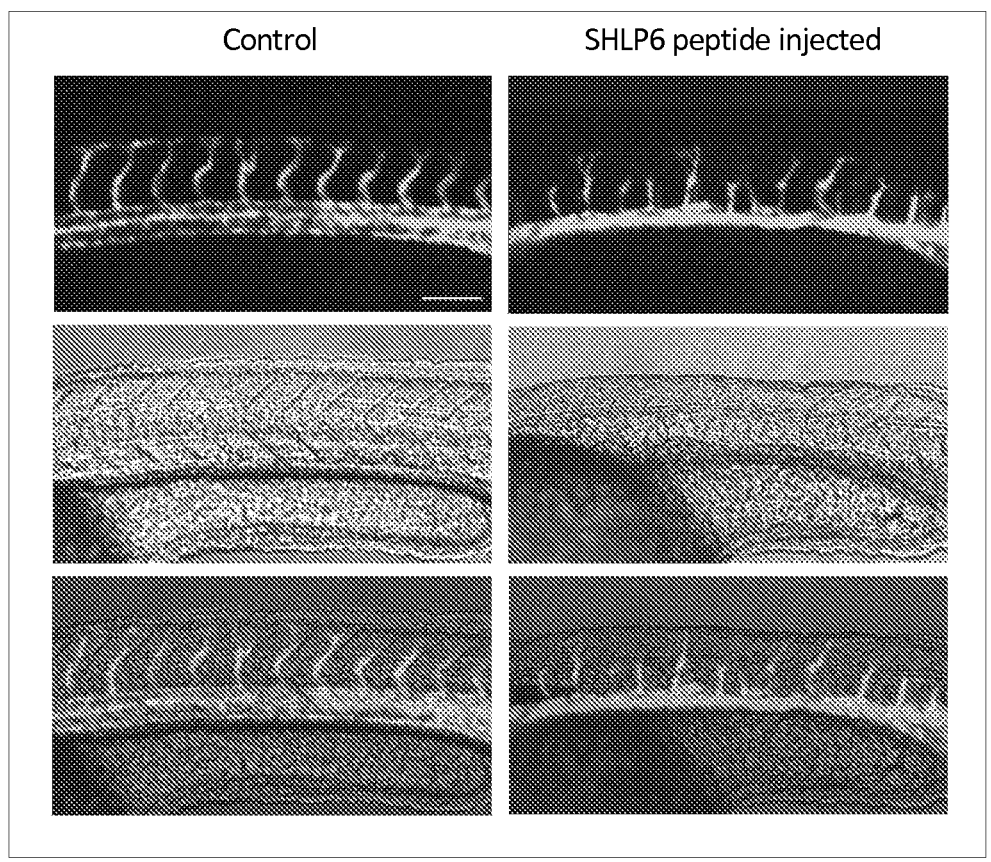
FIG. 23. SHLP6 peptide significantly inhibits vessel formation in zebrafish embryos in vivo. SHLP6 peptide was injected into zebrafish embryos having a vascular system engineered to express green fluorescent protein (GFP), allowing for visualization of blood vessel growth and development. SHLP6 significantly inhibited vessel formation at 48 hpf.

Inhibition of angiogenesis in zebrafish in vivo. To investigate the effect of SHLP6 on angiogenesis in vivo, SHLP6 was injected into embryos of zebrafish having vascular systems engineered to express GFP. SHLP6 significantly inhibited vessel formation at 48 hpf (FIG. 21).

Example 17

Modulation of cancer-associated gene expression. To narrow down the mechanism of action of SHLP6 in prostate cancer cells, the SuperArray RT2 Profiler™ PCR Array: Human Cancer PathwayFinder™ array was used to assay the expression of cancer-associated genes. The array consisted of a 96 well format containing 84 key genes frequently dysregulated in cancer, including genes involved in cell cycle control, DNA damage repair, apoptosis and cell senescence, signal transduction, transcription factors, adhesion, angiogenesis, invasion and metastasis, as well as housekeeping and control genes. 22RV1 cells were incubated in SF media for 24 h followed by incubation with 1 µM SHLP6 or scrambled (control) peptide. RNA was isolated using Trizol, and cDNA was isolated. Real-time PCR analysis was then carried out using SYBR green on a standard ABI real-time PCR machine. A number of genes implicated in apoptosis, adhesion, metastasis and angiogenesis of tumors were up- or down-regulated by SHLP6 treatment (Table 8).

Of the genes upregulated were common apoptosis genes, including Apaf-1 (one component of the cellular apoptosome), Bax and Bcl-x (which can be anti-apoptotic when spliced in to Bcl-xl, and pro-apoptotic when spliced in to Bcl-xs). Several anti-metastasis genes, including TIMP1, NME1 and NME4, were also upregulated. However, the most dramatic change in mRNA expression we observed was for VEGF-A, whose expression was down-regulated more than 70-fold by SHLP6. These observations suggest that the therapeutic potential of SHLP6 is not limited to inducing tumor apoptosis, but may also be extended to anti-angiogenic, anti-metastatic effects in prostate cancer. The observed gene changes are verifiable by, e.g., immunoblotting.

TABLE 8

Genes up- or down-regulated by SHLP6.

| Gene | Fold-Change in Expression | Protein Function |
| --- | --- | --- |
| Apaf-1 | +3 | Apoptotic peptidase activating factor-1; forms part of apoptosome with ATP and cytochrome c |
| BAX | +2 | pro-apoptotic |
| Bcl-2 | +5.5 | Apoptosis regulator |
| Bcl-x | +49 | Depends on splicing; Bcl-xl is anti-apoptotic and Bcl-Xs is pro-apoptotic |
| PI3-kinase p85α | +4 | Regulatory subunit; inhibits tumor formation in some cancers |
| NME1 | +2.5 | NME = non-metastatic, metastasis suppressor |
| NME4 | +4 | |
| Integrin α1 | +2.5 | Regulate cell: cell and cell: ECM contact; regulate signaling from ECM to the cell |
| Integrin α2 | +4 | |
| Integrin α3 | +2 | |
| TIMP1 | +2 | MMP (matrix metalloproteinase) inhibitor; metastasis suppressor |
| COL18A1 | +2 | Endostatin; angiogenesis inhibitor |
| IFNA1 (IFNα) | +2.5 | Angiogenesis inhibitor |
| VEGF-A | −70 | Pro-angiogenic |

Example 18

Modulation of signaling pathways. SHLP6 had no detectable effect on expression levels of survival-related signaling molecules (Akt, ERK, STAT3, JNK) as measured by western blotting. To investigate the effect of SHLP6 on a wider range of signaling pathways, cells were incubated with 1 µM SHLP6 for 2 h and cell lysates were analyzed using an antibody microarray (Kinexus; Vancouver, BC). The array comprised over 650 antibodies encompassing more than 240 protein kinases, 28 phosphatases and 90 other cell signaling proteins that regulate cell proliferation, stress and apoptosis. In addition, the array contained over 270 phospho-site antibodies, allowing changes in the activity of target proteins to be assessed in addition to changes in expression levels. SHLP6 treatment had wide-ranging effects, affecting proteins involved in the regulation of the cell cycle, inflammation, apoptosis and transcription (examples are provided in Table 9). The data indicate that SHLP6 has wide-ranging effects on cellular function.

TABLE 9

| Cellular markers affected by SHLP6. | |
| --- | --- |
| Protein | Fold Change |
| STAT5A Y694 | 0.34 |
| STAT6 (induces expression of anti-apoptotic Bcl-2 family members) | 0.40 |
| EGFR | 0.55 |
| pRb (tumor suppressor) | 1.45 |

TABLE 9-continued

| Cellular markers affected by SHLP6. | |
| --- | --- |
| Protein | Fold Change |
| Caldesmon (calmodulin binding protein; inhibits ATPase activity) | 2.35 |
| ERP72 (ER protein; ER-specific chaperone) | 3.92 |

Those skilled in the art will recognize, or be able to ascertain using no more than routine experimentation, many equivalents to the specific aspects of the invention described herein. Such equivalents are intended to be encompassed by the following claims.

What is claimed:

1. An isolated small humanin-like peptide (SHLP) consisting of an amino acid sequence at least 90% identical to MGVKFFTLSTRFFPSVQRAVPLWTNS (SEQ ID NO: 9), wherein the SHLP has at least one therapeutic activity selected from the group consisting of:
  inhibiting cell death induced by amyloid-beta (Aβ) peptides in Alzheimer's disease,
  inhibiting apoptosis in pancreatic β-cells,
  stimulating insulin-induced differentiation of adipocytes,
  enhancing cellular resistance to environmental stress, and
  inhibiting intracellular production of reactive oxygen species (ROS).

2. A pharmaceutical composition comprising (i) a small humanin-like peptide (SHLP) consisting of an amino acid sequence at least 90% identical to MGVKFFTLSTRFFPSVQRAVPLWTNS (SEQ ID NO: 9); and (ii) at least one pharmaceutically acceptable excipient,
  wherein the SHLP has at least one therapeutic activity selected from the group consisting of inhibiting cell death induced by amyloid-beta (Aβ) peptides in Alzheimer's disease, inhibiting apoptosis in pancreatic β-cells, stimulating insulin-induced differentiation of adipocytes, enhancing cellular resistance to environmental stress, and inhibiting intracellular production of reactive oxygen species (ROS).

* * * * *

SEQUENCE LISTING

<160> NUMBER OF SEQ ID NOS: 387

<210> SEQ ID NO 1
<211> LENGTH: 75
<212> TYPE: DNA
<213> ORGANISM: Homo sapiens

<400> SEQUENCE: 1
ttaccccgcc tgtttaccaa aaacatcacc tctagcatca ccagtattag aggcaccgcc     60
tgcccagtga cacat                                                     75

<210> SEQ ID NO 2
<211> LENGTH: 81
<212> TYPE: DNA
<213> ORGANISM: Homo sapiens

<400> SEQUENCE: 2
ttaactgtta gtccaaagag gaacagctct ttggacacta ggaaaaaacc ttgtagagag     60
agtaaaaaat ttaacaccca t                                              81

<210> SEQ ID NO 3
<211> LENGTH: 117
<212> TYPE: DNA
<213> ORGANISM: Homo sapiens

<400> SEQUENCE: 3
ctaccagaca accttagcca aaccatttac ccaaataaag tataggcgat agaaattgaa     60
acctggcgca atagatatag taccgcaagg gaaagatgaa aaattataac caagcat       117

<210> SEQ ID NO 4
<211> LENGTH: 81
<212> TYPE: DNA
<213> ORGANISM: Homo sapiens

<400> SEQUENCE: 4
tcataaggaa aggttaaaaa aagtaaaagg aactcggcaa atcttacccc gcctgtttac     60
caaaaacatc acctctagca t                                              81

<210> SEQ ID NO 5
<211> LENGTH: 75
<212> TYPE: DNA
<213> ORGANISM: Homo sapiens

<400> SEQUENCE: 5
ctaaactacc aaacctgcat taaaaatttc ggttggggcg acctcggagc agaacccaac     60

-continued

```
ctccgagcag tacat                                              75

<210> SEQ ID NO 6
<211> LENGTH: 63
<212> TYPE: DNA
<213> ORGANISM: Homo sapiens

<400> SEQUENCE: 6
atgttggatc aggacatccc aatggtgcag ccgctattaa aggttcgttt gttcaacgat   60
taa                                                                63

<210> SEQ ID NO 7

<400> SEQUENCE: 7

000

<210> SEQ ID NO 8
<211> LENGTH: 24
<212> TYPE: PRT
<213> ORGANISM: Homo sapiens

<400> SEQUENCE: 8

Met Cys His Trp Ala Gly Gly Ala Ser Asn Thr Gly Asp Ala Arg Gly
1               5                   10                  15

Asp Val Phe Gly Lys Gln Ala Gly
            20

<210> SEQ ID NO 9
<211> LENGTH: 26
<212> TYPE: PRT
<213> ORGANISM: Homo sapiens

<400> SEQUENCE: 9

Met Gly Val Lys Phe Phe Thr Leu Ser Thr Arg Phe Phe Pro Ser Val
1               5                   10                  15

Gln Arg Ala Val Pro Leu Trp Thr Asn Ser
            20                  25

<210> SEQ ID NO 10
<211> LENGTH: 38
<212> TYPE: PRT
<213> ORGANISM: Homo sapiens

<400> SEQUENCE: 10

Met Leu Gly Tyr Asn Phe Ser Ser Phe Pro Cys Gly Thr Ile Ser Ile
1               5                   10                  15

Ala Pro Gly Phe Asn Tyr Arg Leu Tyr Phe Ile Trp Val Asn Gly
            20                  25                  30

Leu Ala Lys Val Val Trp
        35

<210> SEQ ID NO 11
<211> LENGTH: 26
<212> TYPE: PRT
<213> ORGANISM: Homo sapiens

<400> SEQUENCE: 11

Met Leu Glu Val Met Phe Leu Val Asn Arg Arg Gly Lys Ile Cys Arg
1               5                   10                  15

Val Pro Phe Thr Phe Asn Leu Ser Leu
            20                  25
```

```
<210> SEQ ID NO 12
<211> LENGTH: 24
<212> TYPE: PRT
<213> ORGANISM: Homo sapiens

<400> SEQUENCE: 12

Met Tyr Cys Ser Glu Val Gly Phe Cys Ser Glu Val Ala Pro Thr Glu
1               5                   10                  15

Ile Phe Asn Ala Gly Leu Val Val
            20

<210> SEQ ID NO 13
<211> LENGTH: 20
<212> TYPE: PRT
<213> ORGANISM: Homo sapiens

<400> SEQUENCE: 13

Met Leu Asp Gln Asp Ile Pro Met Val Gln Pro Leu Leu Lys Val Arg
1               5                   10                  15

Leu Phe Asn Asp
            20

<210> SEQ ID NO 14
<211> LENGTH: 24
<212> TYPE: PRT
<213> ORGANISM: Unknown
<220> FEATURE:
<223> OTHER INFORMATION: Description of Unknown: Humanin peptide

<400> SEQUENCE: 14

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19
<211> LENGTH: 24
<212> TYPE: PRT
<213> ORGANISM: Unknown
<220> FEATURE:
<223> OTHER INFORMATION: Description of Unknown: Humanin peptide
```

-continued

```
<400> SEQUENCE: 19

Met Ala Pro Arg Gly Phe Ser Cys Leu Leu Leu Ser Thr Ser Glu Ile
1               5                   10                  15

Asp Leu Pro Val Lys Arg Arg Ala
            20

<210> SEQ ID NO 20
<211> LENGTH: 24
<212> TYPE: PRT
<213> ORGANISM: Unknown
<220> FEATURE:
<223> OTHER INFORMATION: Description of Unknown: Humanin peptide

<400> SEQUENCE: 20

Met Ala Pro Arg Gly Phe Ser Cys Leu Leu Leu Ser Thr Ser Glu Ile
1               5                   10                  15

Asp Leu Pro Val Lys Arg Arg Ala
            20

<210> SEQ ID NO 21
<211> LENGTH: 22
<212> TYPE: PRT
<213> ORGANISM: Unknown
<220> FEATURE:
<223> OTHER INFORMATION: Description of Unknown: Humanin peptide

<400> SEQUENCE: 21

Met Ala Pro Arg Gly Phe Ser Cys Leu Leu Leu Ser Thr Ser Glu Ile
1               5                   10                  15

Asp Leu Pro Val Lys Arg
            20

<210> SEQ ID NO 22
<211> LENGTH: 23
<212> TYPE: PRT
<213> ORGANISM: Unknown
<220> FEATURE:
<223> OTHER INFORMATION: Description of Unknown: Humanin peptide

<400> SEQUENCE: 22

Met Thr Pro Arg Gly Phe Ser Cys Leu Leu Leu Pro Thr Ser Glu Thr
1               5                   10                  15

Asp Leu Pro Val Lys Arg Arg
            20

<210> SEQ ID NO 23
<211> LENGTH: 26
<212> TYPE: PRT
<213> ORGANISM: Homo sapiens

<400> SEQUENCE: 23

Met Gly Ile Lys Phe Phe Thr Leu Phe Thr Arg Phe Phe Pro Ser Val
1               5                   10                  15

Gln Arg Ala Val Pro Leu Trp Thr Asn Ser
            20                  25

<210> SEQ ID NO 24
<211> LENGTH: 26
<212> TYPE: PRT
<213> ORGANISM: Homo sapiens

<400> SEQUENCE: 24

Met Leu Glu Val Met Phe Leu Val Asn Arg Arg Gly Lys Ile Cys Arg
1               5                   10                  15
```

Val Pro Phe Thr Phe Phe Asn Leu Ser Leu
            20                  25

<210> SEQ ID NO 25
<211> LENGTH: 26
<212> TYPE: PRT
<213> ORGANISM: Homo sapiens

<400> SEQUENCE: 25

Met Leu Glu Val Met Phe Leu Val Asn Arg Arg Gly Lys Ile Cys Arg
1               5                   10                  15

Val Pro Phe Thr Phe Phe Asn Leu Ser Leu
            20                  25

<210> SEQ ID NO 26
<211> LENGTH: 26
<212> TYPE: PRT
<213> ORGANISM: Homo sapiens

<400> SEQUENCE: 26

Met Leu Glu Val Met Phe Leu Val Asn Arg Arg Gly Lys Ile Cys Arg
1               5                   10                  15

Val Pro Phe Thr Phe Phe Asn Leu Ser Leu
            20                  25

<210> SEQ ID NO 27
<211> LENGTH: 26
<212> TYPE: PRT
<213> ORGANISM: Homo sapiens

<400> SEQUENCE: 27

Met Leu Glu Val Met Phe Leu Val Asn Arg Arg Gly Lys Ile Cys Arg
1               5                   10                  15

Val Pro Phe Thr Phe Phe Asn Leu Ser Leu
            20                  25

<210> SEQ ID NO 28
<211> LENGTH: 26
<212> TYPE: PRT
<213> ORGANISM: Homo sapiens

<400> SEQUENCE: 28

Met Leu Glu Val Met Phe Leu Val Asn Arg Trp Gly Lys Val Cys Arg
1               5                   10                  15

Val Pro Phe Thr Phe Phe Asn Leu Ser Leu
            20                  25

<210> SEQ ID NO 29
<211> LENGTH: 22
<212> TYPE: PRT
<213> ORGANISM: Homo sapiens

<400> SEQUENCE: 29

Met Leu Glu Val Met Phe Leu Val Asn Arg Gln Gly Lys Ile Cys Arg
1               5                   10                  15

Val Pro Phe Asn Phe Phe
            20

<210> SEQ ID NO 30
<211> LENGTH: 25
<212> TYPE: PRT
<213> ORGANISM: Homo sapiens -continued

<400> SEQUENCE: 30

Met Leu Glu Val Met Phe Leu Val Asn Arg Gln Gly Lys Ile Cys Val
1               5                   10                  15

Pro Phe Thr Phe Cys Lys Leu Ser Leu
            20                  25

<210> SEQ ID NO 31
<211> LENGTH: 26
<212> TYPE: PRT
<213> ORGANISM: Homo sapiens

<400> SEQUENCE: 31

Met Leu Glu Val Met Phe Leu Val Asn Arg Trp Gly Lys Ile Cys Arg
1               5                   10                  15

Val Pro Phe Thr Phe Cys Asn Ile Ser Leu
            20                  25

<210> SEQ ID NO 32
<211> LENGTH: 25
<212> TYPE: PRT
<213> ORGANISM: Homo sapiens

<400> SEQUENCE: 32

Met Leu Glu Val Met Phe Leu Ile Asn Arg Arg Gly Lys Ile Arg Val
1               5                   10                  15

Pro Phe Thr Phe Phe Asn Leu Ser Leu
            20                  25

<210> SEQ ID NO 33
<211> LENGTH: 26
<212> TYPE: PRT
<213> ORGANISM: Homo sapiens

<400> SEQUENCE: 33

Met Leu Glu Val Met Phe Leu Val Asn Arg Arg Gly Lys Ile Cys Gly
1               5                   10                  15

Val Pro Phe Thr Phe Cys Ile Leu Ser Leu
            20                  25

<210> SEQ ID NO 34
<211> LENGTH: 25
<212> TYPE: PRT
<213> ORGANISM: Homo sapiens

<400> SEQUENCE: 34

Met Leu Glu Val Met Phe Leu Val Asn Arg Gln Asp Lys Ile Cys Val
1               5                   10                  15

Pro Phe Thr Phe Cys Asn Leu Ser Leu
            20                  25

<210> SEQ ID NO 35
<211> LENGTH: 25
<212> TYPE: PRT
<213> ORGANISM: Homo sapiens

<400> SEQUENCE: 35

Met Leu Glu Val Met Phe Leu Val Asn Arg Arg Gly Lys Ile Gly Ile
1               5                   10                  15

Pro Phe Thr Phe Cys Asn Leu Ser Leu
            20                  25

<210> SEQ ID NO 36

```
<211> LENGTH: 20
<212> TYPE: PRT
<213> ORGANISM: Homo sapiens

<400> SEQUENCE: 36

Met Leu Glu Val Met Phe Leu Val Asn Arg Arg Gly Lys Ile Cys Val
1               5                   10                  15

Pro Phe Ile Phe
            20

<210> SEQ ID NO 37
<211> LENGTH: 26
<212> TYPE: PRT
<213> ORGANISM: Homo sapiens

<400> SEQUENCE: 37

Met Leu Ala Val Met Phe Leu Val Asn Lys Leu Gly Lys Ile Cys Arg
1               5                   10                  15

Val Pro Phe Thr Val Cys Asn Leu Ser Leu
            20                  25

<210> SEQ ID NO 38
<211> LENGTH: 22
<212> TYPE: PRT
<213> ORGANISM: Homo sapiens

<400> SEQUENCE: 38

Val Phe Leu Val Asn Arg Gln Ser Met Ile Cys Arg Val Pro Phe Thr
1               5                   10                  15

Phe Cys Asn Leu Ser Leu
            20

<210> SEQ ID NO 39
<211> LENGTH: 26
<212> TYPE: PRT
<213> ORGANISM: Homo sapiens

<400> SEQUENCE: 39

Met Leu Glu Val Val Phe Leu Val Asn Arg Gln Gly Lys Ile Cys Gln
1               5                   10                  15

Phe Pro Phe Thr Phe Cys Asn Leu Ser Leu
            20                  25

<210> SEQ ID NO 40
<211> LENGTH: 26
<212> TYPE: PRT
<213> ORGANISM: Homo sapiens

<400> SEQUENCE: 40

Met Leu Glu Val Met Phe Leu Val Asn Arg Arg Asp Lys Ile Cys Gln
1               5                   10                  15

Val Pro Phe Thr Phe Cys Asn Phe Ser Leu
            20                  25

<210> SEQ ID NO 41
<211> LENGTH: 26
<212> TYPE: PRT
<213> ORGANISM: Homo sapiens

<400> SEQUENCE: 41

Met Leu Gly Val Met Phe Leu Val Glu Arg Trp Gly Glu Met Cys Arg
1               5                   10                  15

Val Pro Phe Thr Phe Cys Asn Leu Ser Leu
```

<210> SEQ ID NO 42
<211> LENGTH: 20
<212> TYPE: PRT
<213> ORGANISM: Homo sapiens

<400> SEQUENCE: 42

Met Leu Asp Gln Asp Ile Pro Met Val Gln Pro Leu Leu Lys Val Arg
1               5                   10                  15

Leu Phe Asn Asp
            20

<210> SEQ ID NO 43
<211> LENGTH: 19
<212> TYPE: PRT
<213> ORGANISM: Homo sapiens

<400> SEQUENCE: 43

Met Leu Asp Gln Asp Ile Leu Met Val Leu Leu Leu Arg Val Arg Leu
1               5                   10                  15

Phe Asn Asp

<210> SEQ ID NO 44
<211> LENGTH: 20
<212> TYPE: PRT
<213> ORGANISM: Homo sapiens

<400> SEQUENCE: 44

Met Leu Asp Gln Asp Ile Leu Ile Val Gln Pro Leu Leu Arg Val His
1               5                   10                  15

Leu Phe Asn Asp
            20

<210> SEQ ID NO 45
<211> LENGTH: 20
<212> TYPE: PRT
<213> ORGANISM: Homo sapiens

<400> SEQUENCE: 45

Met Leu Asp Gln Asp Met Leu Met Val Gln Pro Leu Ser Lys Val Arg
1               5                   10                  15

Leu Phe Asn Asp
            20

<210> SEQ ID NO 46
<211> LENGTH: 19
<212> TYPE: PRT
<213> ORGANISM: Homo sapiens

<400> SEQUENCE: 46

Met Leu Asp Gln Asp Ile Gln Met Val Pro Leu Leu Arg Val Cys Leu
1               5                   10                  15

Phe Lys Asp

<210> SEQ ID NO 47
<211> LENGTH: 19
<212> TYPE: PRT
<213> ORGANISM: Homo sapiens

<400> SEQUENCE: 47

Met Leu Asp Gln Asp Val Leu Met Val Pro Leu Ile Arg Val Arg Leu
1               5                   10                  15

<210> SEQ ID NO 48
<211> LENGTH: 19
<212> TYPE: PRT
<213> ORGANISM: Homo sapiens

<400> SEQUENCE: 48

Met Leu Asp Gln Asp Ile Leu Met Val Pro Leu Leu Arg Val His Leu
1               5                   10                  15

Phe Asn Asp

<210> SEQ ID NO 49
<211> LENGTH: 80
<212> TYPE: DNA
<213> ORGANISM: Homo sapiens

<400> SEQUENCE: 49
ttaactgtta gtccaaagag gaacagctct ttggacacta ggaaaaaacc ttgtaaagag      60
agtaaaaaat ttaataccca                                                 80

<210> SEQ ID NO 50
<211> LENGTH: 79
<212> TYPE: DNA
<213> ORGANISM: Homo sapiens

<400> SEQUENCE: 50
ataaggaaag gttaaaaaaa gtaaaggaa ctcggcaaat cttaccccgc ctgtttacca       60
aaaacatcac ctctagcat                                                  79

<210> SEQ ID NO 51
<211> LENGTH: 81
<212> TYPE: DNA
<213> ORGANISM: Homo sapiens

<400> SEQUENCE: 51
tcataaggaa aggttaaaaa aagtaaaagg aactcggcaa atcttacccc gcctgtttac      60
caaaaacatc acctctagca t                                               81

<210> SEQ ID NO 52
<211> LENGTH: 81
<212> TYPE: DNA
<213> ORGANISM: Homo sapiens

<400> SEQUENCE: 52
tcataaggaa aggttaaaaa aagtaaaagg aactcggcaa atcttacccc gcctgtttac      60
caaaaacatc acctctagca t                                               81

<210> SEQ ID NO 53
<211> LENGTH: 81
<212> TYPE: DNA
<213> ORGANISM: Homo sapiens

<400> SEQUENCE: 53
tcataaggaa aggttaaaaa aagtaaaagg aactcggcaa atcttacccc gcctgtttac      60
caaaaacatc acctctagca t                                               81

<210> SEQ ID NO 54
<211> LENGTH: 77
<212> TYPE: DNA

-continued

<213> ORGANISM: Homo sapiens

<400> SEQUENCE: 54
aaggaaaggt taaaaaaagt aaaaggaact cggcaaacct taccccacct gtttaccaaa    60
aacatcacct ctagcat    77

<210> SEQ ID NO 55
<211> LENGTH: 79
<212> TYPE: DNA
<213> ORGANISM: Homo sapiens

<400> SEQUENCE: 55
taaggaaagg ttaaaaaaaa ttaaaaggaa ctcggcaaat tttaccctgc ctgtttacca    60
aaaacatcac ctctagcat    79

<210> SEQ ID NO 56
<211> LENGTH: 78
<212> TYPE: DNA
<213> ORGANISM: Homo sapiens

<400> SEQUENCE: 56
taaggaaagt ttcaaaaaag taaaaggaac tcagcaaatc ttaccctgcc tgtttaccaa    60
aaacatcacc tctagcat    78

<210> SEQ ID NO 57
<211> LENGTH: 78
<212> TYPE: DNA
<213> ORGANISM: Homo sapiens

<400> SEQUENCE: 57
taaggaaata ttcaaaaaag taaaaggaac tcggcaaatc ttaccccacc tgtttaccaa    60
aaacatcacc tctagcat    78

<210> SEQ ID NO 58
<211> LENGTH: 77
<212> TYPE: DNA
<213> ORGANISM: Homo sapiens

<400> SEQUENCE: 58
aaggaaaggt taaaaaaagt aaaaggaact cagcgaatct taccctcct gtttatcaaa    60 aacatcacct ctagcat    77

<210> SEQ ID NO 59
<211> LENGTH: 78
<212> TYPE: DNA
<213> ORGANISM: Homo sapiens

<400> SEQUENCE: 59
taaggaaaga ttacaaaaag taaaaggaac tcagcaaatc ttatcctgcc tgtttaccaa    60
aaacatcacc tctagcat    78

<210> SEQ ID NO 60
<211> LENGTH: 78
<212> TYPE: DNA
<213> ORGANISM: Homo sapiens

<400> SEQUENCE: 60
taaggaaaga ttacaaaaag taaaaggaat tcagccaatc ttaccccgcc tgtttaccaa    60
aaacatcacc tctagcat    78

```
<210> SEQ ID NO 61
<211> LENGTH: 79
<212> TYPE: DNA
<213> ORGANISM: Homo sapiens

<400> SEQUENCE: 61
taaggaaaca ttacaaaaaa ataaaaggaa ctcagcaaat cttacccgc ctgtttacca      60 aaaacatcac ctctagcat                                                  79

<210> SEQ ID NO 62
<211> LENGTH: 78
<212> TYPE: DNA
<213> ORGANISM: Homo sapiens

<400> SEQUENCE: 62
taaggaaaga ttacaaacag taaaaggaac tcggcaaatc ttacccagct tgtttaccaa     60
aaacatcacc gctagcat                                                   78

<210> SEQ ID NO 63
<211> LENGTH: 77
<212> TYPE: DNA
<213> ORGANISM: Homo sapiens

<400> SEQUENCE: 63
taaggaaaga ttacaaaaag taaaaggaac tcggcaaatc atactctgcc tgtttaccaa     60
aaacacacct ctagcat                                                    77

<210> SEQ ID NO 64
<211> LENGTH: 78
<212> TYPE: DNA
<213> ORGANISM: Homo sapiens

<400> SEQUENCE: 64
taaggaaaga ttacaaaaag taaaaggaaa ttggcaaatc ttaccttgcc tgtttaccaa     60
aaacaccacc tctagcat                                                   78

<210> SEQ ID NO 65
<211> LENGTH: 78
<212> TYPE: DNA
<213> ORGANISM: Homo sapiens

<400> SEQUENCE: 65
taaggaaaaa ttacaaaaag taaaaggaac ttggcaaatc ttgtcccgcc tatttaccaa     60
aaacatcacc tctagcat                                                   78

<210> SEQ ID NO 66
<211> LENGTH: 78
<212> TYPE: DNA
<213> ORGANISM: Homo sapiens

<400> SEQUENCE: 66
taaggaaaga ttacaaaaag taaaaggaac tcggcacatt tcaccccatc tctctaccaa     60
aaacatcacc cctagcat                                                   78

<210> SEQ ID NO 67
<211> LENGTH: 81
<212> TYPE: DNA
<213> ORGANISM: Homo sapiens

<400> SEQUENCE: 67
```

```
taaggaaaga ttttttaaaa agtaaaagga actcagcaaa aggaaacccg tcttgtttac    60
caaaaacatc acctctagca t                                              81

<210> SEQ ID NO 68
<211> LENGTH: 63
<212> TYPE: DNA
<213> ORGANISM: Homo sapiens

<400> SEQUENCE: 68
atgttggatc aggacatccc aatggtgcag ccgctattaa aggttcgttt gttcaacgat    60
taa                                                                  63

<210> SEQ ID NO 69
<211> LENGTH: 63
<212> TYPE: DNA
<213> ORGANISM: Homo sapiens

<400> SEQUENCE: 69
atgttggatc aggacatcct aatggtgtag ctgctattaa gggttcgttt gttcaatgat    60
taa                                                                  63

<210> SEQ ID NO 70
<211> LENGTH: 63
<212> TYPE: DNA
<213> ORGANISM: Homo sapiens

<400> SEQUENCE: 70
atgttggatc aggacatcct aattgtacag ccactattaa gggttcattt gttcaacgat    60
taa                                                                  63

<210> SEQ ID NO 71
<211> LENGTH: 61
<212> TYPE: DNA
<213> ORGANISM: Homo sapiens

<400> SEQUENCE: 71
atgttggatc aggacatgct gatggtgcag ccgctatcaa aggttcgttt gttcaatgat    60
t                                                                    61

<210> SEQ ID NO 72
<211> LENGTH: 63
<212> TYPE: DNA
<213> ORGANISM: Homo sapiens

<400> SEQUENCE: 72
atgttggatc aggacatcca aatggtgtag ccactattaa gggtttgtct gttcaaagat    60
taa                                                                  63

<210> SEQ ID NO 73
<211> LENGTH: 63
<212> TYPE: DNA
<213> ORGANISM: Homo sapiens

<400> SEQUENCE: 73
atgttggatc aggacgtcct aatggtgtag ccgctaataa gggttcgttt gttcaatgat    60
caa                                                                  63

<210> SEQ ID NO 74
<211> LENGTH: 63
<212> TYPE: DNA
```

```
<213> ORGANISM: Homo sapiens

<400> SEQUENCE: 74
atgttggatc aggacatcct aatggtgtag ccgctattaa gggttcattt attcaatgat    60
taa                                                                  63

<210> SEQ ID NO 75
<211> LENGTH: 24
<212> TYPE: PRT
<213> ORGANISM: Pan sp.

<400> SEQUENCE: 75

Met Cys His Arg Ala Gly Gly Ala Ser Asn Thr Gly Asn Ala Arg Gly
1               5                   10                  15

Asp Val Phe Gly Lys Gln Ala Gly
            20

<210> SEQ ID NO 76
<211> LENGTH: 24
<212> TYPE: PRT
<213> ORGANISM: Pongo sp.

<400> SEQUENCE: 76

Met Cys His Arg Ala Gly Gly Ala Ser Asn Thr Gly Asn Ala Arg Gly
1               5                   10                  15

Asp Val Phe Gly Lys Gln Ala Gly
            20

<210> SEQ ID NO 77
<211> LENGTH: 23
<212> TYPE: PRT
<213> ORGANISM: Macaca mulatta

<400> SEQUENCE: 77

Met Cys Trp Ala Gly Ser Asp Ser His Thr Gly Asn Ala Arg Gly Asp
1               5                   10                  15

Val Phe Gly Lys Gln Met Gly
            20

<210> SEQ ID NO 78
<211> LENGTH: 21
<212> TYPE: PRT
<213> ORGANISM: Macaca mulatta

<400> SEQUENCE: 78

Met Cys His Trp Ala Gly Gly Ala Ser Asn Thr Gly Asn Ala Arg Gly
1               5                   10                  15

Asp Val Phe Gly Lys
            20

<210> SEQ ID NO 79
<211> LENGTH: 34
<212> TYPE: PRT
<213> ORGANISM: Macaca mulatta

<400> SEQUENCE: 79

Met Cys His Trp Ala Gly Ser Ala Ser Asn Thr Ser Asn Ala Arg Gly
1               5                   10                  15

Asp Val Phe Gly Lys Gln Ala Glu Val Lys Phe Ala Glu Phe Leu Leu
            20                  25                  30

Leu Phe
```

```
<210> SEQ ID NO 80
<211> LENGTH: 34
<212> TYPE: PRT
<213> ORGANISM: Macaca mulatta

<400> SEQUENCE: 80

Met Cys Gln Trp Ala Gly Gly Ala Ser Asn Thr Gly Asn Ala Ser Gly
1               5                   10                  15

Asp Val Phe Gly Lys Gln Ala Gly Leu Ser Leu Leu Ser Phe Tyr
            20                  25                  30

Phe Phe

<210> SEQ ID NO 81
<211> LENGTH: 37
<212> TYPE: PRT
<213> ORGANISM: Unknown
<220> FEATURE:
<223> OTHER INFORMATION: Description of Unknown: Cat polypeptide

<400> SEQUENCE: 81

Met Ser Leu Gly Arg Pro Cys Leu Asn Thr Lys Asn Ala Arg Gly Asp
1               5                   10                  15

Val Ile Gly Lys Gln Ala Gly Ser Val Phe Val Glu Ser Leu Leu Leu
            20                  25                  30

Leu Leu Ile Phe Leu
        35

<210> SEQ ID NO 82
<211> LENGTH: 16
<212> TYPE: PRT
<213> ORGANISM: Pan sp.

<400> SEQUENCE: 82

Met Gly Val Lys Phe Phe Thr Leu Phe Thr Arg Phe Phe Pro Ser Val
1               5                   10                  15

<210> SEQ ID NO 83
<211> LENGTH: 16
<212> TYPE: PRT
<213> ORGANISM: Pan sp.

<400> SEQUENCE: 83

Met Gly Val Lys Phe Phe Thr Leu Phe Thr Arg Phe Phe Pro Ser Val
1               5                   10                  15

<210> SEQ ID NO 84
<211> LENGTH: 26
<212> TYPE: PRT
<213> ORGANISM: Pan sp.

<400> SEQUENCE: 84

Met Gly Ile Lys Phe Phe Thr Leu Phe Thr Arg Phe Phe Pro Ser Val
1               5                   10                  15

Gln Arg Ala Val Pro Leu Trp Thr Asn Ser
            20                  25

<210> SEQ ID NO 85
<211> LENGTH: 26
<212> TYPE: PRT
<213> ORGANISM: Pan sp.

<400> SEQUENCE: 85

Met Gly Ile Lys Phe Phe Thr Leu Phe Thr Ser Phe Phe Pro Ser Val
```

```
                1               5                   10                  15
Gln Arg Ala Val Pro Leu Trp Thr Asn Ser
            20                  25
```

<210> SEQ ID NO 86
<211> LENGTH: 16
<212> TYPE: PRT
<213> ORGANISM: Pongo sp.

<400> SEQUENCE: 86

```
Met Gly Val Val Phe Phe Thr Leu Phe Leu Arg Phe Phe Pro Ser Val
1               5                   10                  15
```

<210> SEQ ID NO 87
<211> LENGTH: 13
<212> TYPE: PRT
<213> ORGANISM: Pongo sp.

<400> SEQUENCE: 87

```
Met Gly Val Val Phe Leu Leu Ser Phe Gln Gly Phe Ser
1               5                   10
```

<210> SEQ ID NO 88
<211> LENGTH: 47
<212> TYPE: PRT
<213> ORGANISM: Pan sp.

<400> SEQUENCE: 88

```
Met Leu Glu Val Met Phe Leu Val Asn Arg Arg Gly Lys Ile Cys Arg
1               5                   10                  15

Val Pro Phe Thr Phe Phe Asn Leu Ser Leu Trp Ala Cys Leu Cys Trp
            20                  25                  30

Val Asn Ser Gly Gly Asn Asn Gly Leu Leu Val Asp Cys Arg Tyr
            35                  40                  45
```

<210> SEQ ID NO 89
<211> LENGTH: 35
<212> TYPE: PRT
<213> ORGANISM: Pan sp.

<400> SEQUENCE: 89

```
Met Leu Glu Val Ile Phe Leu Val Asn Arg Pro Ser Lys Ile Cys Arg
1               5                   10                  15

Val Pro Phe Thr Phe Cys Asn Leu Ser Leu Glu His Ala Cys Val Gly
            20                  25                  30

Leu Thr Glu
            35
```

<210> SEQ ID NO 90
<211> LENGTH: 50
<212> TYPE: PRT
<213> ORGANISM: Pan sp.

<400> SEQUENCE: 90

```
Met Leu Glu Val Val Phe Leu Val Asn Arg Gln Gly Lys Ile Cys Arg
1               5                   10                  15

Phe Pro Phe Thr Phe Cys Asn Leu Ser Leu Glu Tyr Asp Cys Val Gly
            20                  25                  30

Leu Thr Val Lys Ile Thr Gly Tyr Leu Leu Tyr Arg Leu Leu Ile Leu
            35                  40                  45

Gly Cys
    50
```

<210> SEQ ID NO 91
<211> LENGTH: 15
<212> TYPE: PRT
<213> ORGANISM: Pan sp.

<400> SEQUENCE: 91

Met Leu Glu Val Met Phe Leu Val Asn Arg Gln Gly Lys Ile Cys
1               5                   10                  15

<210> SEQ ID NO 92
<211> LENGTH: 35
<212> TYPE: PRT
<213> ORGANISM: Pan sp.

<400> SEQUENCE: 92

Met Leu Glu Val Met Phe Leu Val Asn Arg Trp Gly Lys Ile Cys His
1               5                   10                  15

Val Pro Leu Thr Phe Cys Asn Leu Ser Leu Glu His Thr Leu Val Gly
            20                  25                  30

Leu Thr Val
        35

<210> SEQ ID NO 93
<211> LENGTH: 42
<212> TYPE: PRT
<213> ORGANISM: Pan sp.

<400> SEQUENCE: 93

Met Leu Glu Val Arg Phe Leu Val Asn Arg Arg Gly Lys Ile Cys Arg
1               5                   10                  15

Val Gln Leu Leu Phe Leu Thr Phe Pro Cys Gly His Ala Cys Val Gly
            20                  25                  30

Leu Thr Val Gly Val Ile Met Ala Cys Trp
        35                  40

<210> SEQ ID NO 94
<211> LENGTH: 55
<212> TYPE: PRT
<213> ORGANISM: Pan sp.

<400> SEQUENCE: 94

Met Leu Glu Val Met Phe Leu Val Asn Arg Arg Gly Lys Ile Cys Arg
1               5                   10                  15

Val Pro Phe Thr Phe Phe Asn Leu Ser Leu Trp Ala Cys Leu Cys Trp
            20                  25                  30

Val Asn Ser Arg Ser Asn Thr Val Ser Phe Phe Tyr Ile Trp Leu Ala
        35                  40                  45

Asn Tyr Pro Ser Thr Ile Cys
    50                  55

<210> SEQ ID NO 95
<211> LENGTH: 26
<212> TYPE: PRT
<213> ORGANISM: Pan sp.

<400> SEQUENCE: 95

Met Leu Glu Val Met Phe Leu Val Asn Arg Arg Gly Lys Ile Cys Arg
1               5                   10                  15

Val Pro Phe Thr Phe Phe Asn Leu Ser Leu
            20                  25

```
<210> SEQ ID NO 96
<211> LENGTH: 22
<212> TYPE: PRT
<213> ORGANISM: Pan sp.

<400> SEQUENCE: 96

Met Leu Glu Val Met Phe Leu Val Asn Arg Gln Gly Lys Ile Cys Arg
1               5                   10                  15

Val Pro Phe Asn Phe Phe
            20

<210> SEQ ID NO 97
<211> LENGTH: 35
<212> TYPE: PRT
<213> ORGANISM: Pan sp.

<400> SEQUENCE: 97

Met Leu Glu Val Met Phe Leu Val Asn Arg Gln Gly Lys Thr Cys Arg
1               5                   10                  15

Val Pro Phe Ser Phe Cys Asn Leu Ser Leu Glu His Thr Cys Val Gly
            20                  25                  30

Leu Thr Val
        35

<210> SEQ ID NO 98
<211> LENGTH: 32
<212> TYPE: PRT
<213> ORGANISM: Pan sp.

<400> SEQUENCE: 98

Met Leu Glu Val Met Phe Leu Val Asn Arg Arg Asp Lys Ile Cys Gln
1               5                   10                  15

Val Pro Phe Thr Phe Cys Asn Phe Ser Leu Glu His Thr Cys Val Gly
            20                  25                  30

<210> SEQ ID NO 99
<211> LENGTH: 35
<212> TYPE: PRT
<213> ORGANISM: Pan sp.

<400> SEQUENCE: 99

Met Leu Glu Val Met Phe Leu Val Asn Arg Gln Gly Met Ile Cys Arg
1               5                   10                  15

Val Leu Phe Thr Phe Cys Ser Pro Ser Leu Glu His Thr Cys Val Arg
            20                  25                  30

Leu Lys Met
        35

<210> SEQ ID NO 100
<211> LENGTH: 47
<212> TYPE: PRT
<213> ORGANISM: Pan sp.

<400> SEQUENCE: 100

Met Leu Glu Val Met Phe Leu Val Asn Arg Arg Gly Lys Ile Cys Arg
1               5                   10                  15

Val Pro Phe Thr Phe Phe Asn Leu Ser Leu Trp Ala Cys Leu Cys Trp
            20                  25                  30

Val Asn Ser Gly Gly Asn Asn Gly Leu Leu Val Asp Cys Arg Tyr
        35                  40                  45
```

```
<210> SEQ ID NO 101
<211> LENGTH: 10
<212> TYPE: PRT
<213> ORGANISM: Pan sp.

<400> SEQUENCE: 101

Met Leu Glu Val Met Phe Leu Val Asn Arg
1               5                   10

<210> SEQ ID NO 102
<211> LENGTH: 15
<212> TYPE: PRT
<213> ORGANISM: Pan sp.

<400> SEQUENCE: 102

Met Leu Gln Val Met Phe Leu Val Asn Arg Arg Gly Lys Ile Gly
1               5                   10                  15

<210> SEQ ID NO 103
<211> LENGTH: 44
<212> TYPE: PRT
<213> ORGANISM: Pan sp.

<400> SEQUENCE: 103

Met Leu Glu Val Met Phe Leu Val Asn Arg Arg Gly Lys Ile Cys Arg
1               5                   10                  15

Val Pro Phe Thr Phe Phe Asn Leu Ser Leu Trp Ala Cys Leu Cys Trp
            20                  25                  30

Val Asn Ser Gly Gly Asn Ser Glu Ala Gln Val Cys
        35                  40

<210> SEQ ID NO 104
<211> LENGTH: 47
<212> TYPE: PRT
<213> ORGANISM: Pan sp.

<400> SEQUENCE: 104

Met Leu Glu Val Met Phe Leu Val Asn Arg Arg Gly Lys Val Cys Arg
1               5                   10                  15

Val Pro Phe Thr Phe Phe Asn Leu Ser Leu Trp Ala Cys Leu Cys Trp
            20                  25                  30

Val Asn Ser Gly Gly Asn Asn Gly Leu Leu Val Gly Cys Arg Tyr
        35                  40                  45

<210> SEQ ID NO 105
<211> LENGTH: 26
<212> TYPE: PRT
<213> ORGANISM: Pan sp.

<400> SEQUENCE: 105

Met Leu Glu Val Met Phe Leu Val Ser Arg Trp Gly Lys Ile Cys Arg
1               5                   10                  15

Val Pro Phe Thr Phe Phe Asn Leu Ser Leu
            20                  25

<210> SEQ ID NO 106
<211> LENGTH: 35
<212> TYPE: PRT
<213> ORGANISM: Pan sp.

<400> SEQUENCE: 106

Met Leu Glu Val Met Phe Leu Val Asn Lys Leu Gly Lys Ile Cys Arg
1               5                   10                  15
```

Val Pro Phe Thr Val Cys Asn Leu Ser Leu Glu His Thr Cys Val Gly
            20                  25                  30

Leu Thr Val
        35

<210> SEQ ID NO 107
<211> LENGTH: 10
<212> TYPE: PRT
<213> ORGANISM: Pan sp.

<400> SEQUENCE: 107

Met Leu Glu Val Met Phe Leu Val Asn Arg
1               5                   10

<210> SEQ ID NO 108
<211> LENGTH: 35
<212> TYPE: PRT
<213> ORGANISM: Pan sp.

<400> SEQUENCE: 108

Met Leu Glu Val Met Phe Leu Val Asn Arg Arg Gly Lys Ile Cys Gly
1               5                   10                  15

Val Pro Phe Thr Phe Cys Ile Leu Ser Leu Glu His Thr Cys Val Gly
            20                  25                  30

Leu Thr Val
        35

<210> SEQ ID NO 109
<211> LENGTH: 15
<212> TYPE: PRT
<213> ORGANISM: Pan sp.

<400> SEQUENCE: 109

Met Leu Glu Val Met Phe Leu Val Asn Arg Gln Gly Thr Ile Cys
1               5                   10                  15

<210> SEQ ID NO 110
<211> LENGTH: 15
<212> TYPE: PRT
<213> ORGANISM: Pan sp.

<400> SEQUENCE: 110

Met Leu Glu Val Met Phe Leu Val Asn Arg Gln Gly Thr Ile Cys
1               5                   10                  15

<210> SEQ ID NO 111
<211> LENGTH: 15
<212> TYPE: PRT
<213> ORGANISM: Pan sp.

<400> SEQUENCE: 111

Met Leu Glu Val Met Phe Leu Val Asn Arg Gln Gly Thr Ile Cys
1               5                   10                  15

<210> SEQ ID NO 112
<211> LENGTH: 26
<212> TYPE: PRT
<213> ORGANISM: Pongo sp.

<400> SEQUENCE: 112

Met Leu Glu Val Met Phe Leu Val Asn Arg Arg Gly Glu Ile Cys Arg
1               5                   10                  15

Val Pro Phe Thr Phe Phe Asn Leu Ser Leu
            20                  25

<210> SEQ ID NO 113
<211> LENGTH: 15
<212> TYPE: PRT
<213> ORGANISM: Pongo sp.

<400> SEQUENCE: 113

Met Leu Glu Val Met Phe Leu Val Asn Ser Gln Gly Met Ile Cys
1               5                   10                  15

<210> SEQ ID NO 114
<211> LENGTH: 50
<212> TYPE: PRT
<213> ORGANISM: Pongo sp.

<400> SEQUENCE: 114

Met Leu Glu Met Val Phe Leu Val Asn Arg Gln Gly Lys Ile Cys Arg
1               5                   10                  15

Phe Pro Phe Thr Phe Cys Asn Leu Ser Leu Glu Tyr Asp Cys Val Gly
            20                  25                  30

Leu Thr Val Lys Ile Thr Gly Cys Leu Leu Tyr His Leu Leu Ile Leu
        35                  40                  45

Asp Cys
    50

<210> SEQ ID NO 115
<211> LENGTH: 35
<212> TYPE: PRT
<213> ORGANISM: Pongo sp.

<400> SEQUENCE: 115

Met Leu Glu Val Met Phe Leu Val Asn Arg Trp Gly Lys Ile Cys Arg
1               5                   10                  15

Val Pro Leu Thr Phe Cys Asn Leu Ser Leu Glu His Thr Leu Val Gly
            20                  25                  30

Leu Thr Val
        35

<210> SEQ ID NO 116
<211> LENGTH: 35
<212> TYPE: PRT
<213> ORGANISM: Pongo sp.

<400> SEQUENCE: 116

Met Leu Glu Val Met Phe Leu Val Asn Arg Trp Gly Lys Ile Cys Arg
1               5                   10                  15

Val Pro Leu Thr Phe Cys Asn Leu Ser Leu Glu His Ala Leu Val Gly
            20                  25                  30

Leu Thr Val
        35

<210> SEQ ID NO 117
<211> LENGTH: 47
<212> TYPE: PRT
<213> ORGANISM: Pongo sp.

<400> SEQUENCE: 117

Met Leu Glu Val Met Phe Leu Val Asn Arg Gln Gly Lys Ile Cys Gln
1               5                   10                  15

Val Pro Phe Thr Phe Asn Leu Ser Tyr Lys His Ala Cys Val Gly
            20                  25                  30

```
Leu Thr Val Trp Val Ala Pro Val Cys Leu Lys Pro Ala Thr Leu
         35                  40                  45
```

<210> SEQ ID NO 118
<211> LENGTH: 35
<212> TYPE: PRT
<213> ORGANISM: Pongo sp.

<400> SEQUENCE: 118

```
Met Leu Glu Val Met Phe Leu Val Asn Arg Gln Gly Lys Ile Cys Arg
1               5                  10                  15

Val Pro Phe Thr Leu Phe Asn Leu Ser Leu Glu His Ala Cys Val Gly
            20                  25                  30

Leu Thr Val
         35
```

<210> SEQ ID NO 119
<211> LENGTH: 32
<212> TYPE: PRT
<213> ORGANISM: Pongo sp.

<400> SEQUENCE: 119

```
Met Leu Glu Val Met Phe Leu Val Asn Arg Trp Asp Lys Ile Cys Gln
1               5                  10                  15

Val Pro Phe Thr Phe Cys Asn Phe Ser Leu Glu His Thr Cys Val Gly
            20                  25                  30
```

<210> SEQ ID NO 120
<211> LENGTH: 24
<212> TYPE: PRT
<213> ORGANISM: Pongo sp.

<400> SEQUENCE: 120

```
Met Leu Glu Val Met Phe Leu Val Asn Arg Trp Gly Lys Ile Cys Leu
1               5                  10                  15

Val Pro Phe Phe Val Ile Phe Pro
            20
```

<210> SEQ ID NO 121
<211> LENGTH: 15
<212> TYPE: PRT
<213> ORGANISM: Pongo sp.

<400> SEQUENCE: 121

```
Met Leu Glu Val Met Phe Leu Val Asn Ser Arg Gly Lys Ile Cys
1               5                  10                  15
```

<210> SEQ ID NO 122
<211> LENGTH: 15
<212> TYPE: PRT
<213> ORGANISM: Pongo sp.

<400> SEQUENCE: 122

```
Met Leu Gly Val Met Phe Leu Val Lys Arg Arg Ser Glu Met Cys
1               5                  10                  15
```

<210> SEQ ID NO 123
<211> LENGTH: 15
<212> TYPE: PRT
<213> ORGANISM: Pongo sp.

<400> SEQUENCE: 123

```
Met Leu Glu Val Met Phe Leu Val Asn Arg Gln Gly Lys Ile Cys
1               5                  10                  15
```

```
<210> SEQ ID NO 124
<211> LENGTH: 25
<212> TYPE: PRT
<213> ORGANISM: Pongo sp.

<400> SEQUENCE: 124

Met Leu Glu Val Met Phe Leu Val Asn Arg Arg Gly Glu Ile Cys Arg
1               5                   10                  15

Val Pro Phe Thr Phe Phe Asn Leu Ser
            20                  25

<210> SEQ ID NO 125
<211> LENGTH: 26
<212> TYPE: PRT
<213> ORGANISM: Pongo sp.

<400> SEQUENCE: 125

Met Leu Glu Val Met Phe Leu Val Asn Arg Arg Gly Glu Ile Cys Arg
1               5                   10                  15

Val Pro Phe Thr Phe Phe Asn Leu Ser Leu
            20                  25

<210> SEQ ID NO 126
<211> LENGTH: 35
<212> TYPE: PRT
<213> ORGANISM: Pongo sp.

<400> SEQUENCE: 126

Met Leu Glu Val Met Phe Leu Val Asn Lys Leu Gly Lys Ile Cys Arg
1               5                   10                  15

Val Pro Phe Thr Val Cys Asn Leu Ser Leu Glu His Thr Cys Val Gly
            20                  25                  30

Leu Thr Val
        35

<210> SEQ ID NO 127
<211> LENGTH: 35
<212> TYPE: PRT
<213> ORGANISM: Pongo sp.

<400> SEQUENCE: 127

Met Leu Glu Val Met Phe Leu Val Asn Arg Arg Asp Lys Ile Cys Gln
1               5                   10                  15

Val Pro Phe Thr Phe Cys Asn Leu Ser Leu Glu His Thr Cys Val Gly
            20                  25                  30

Leu Thr Val
        35

<210> SEQ ID NO 128
<211> LENGTH: 15
<212> TYPE: PRT
<213> ORGANISM: Pongo sp.

<400> SEQUENCE: 128

Met Leu Glu Val Met Phe Leu Val Asn Arg Arg Gly Lys Ile Cys
1               5                   10                  15

<210> SEQ ID NO 129
<211> LENGTH: 35
<212> TYPE: PRT
<213> ORGANISM: Pongo sp.
```

-continued

<400> SEQUENCE: 129

Met Leu Glu Val Met Phe Leu Val Asn Arg Trp Gly Lys Ile Cys Gly
1               5                   10                  15

Val Pro Phe Thr Phe Cys Ile Leu Ser Leu Glu His Thr Cys Val Gly
            20                  25                  30

Leu Thr Val
        35

<210> SEQ ID NO 130
<211> LENGTH: 22
<212> TYPE: PRT
<213> ORGANISM: Macaca mulatta

<400> SEQUENCE: 130

Met Leu Glu Val Met Phe Leu Val Asn Arg Arg Gly Leu Ser Leu Pro
1               5                   10                  15

Ser Ser Phe Tyr Phe Phe
            20

<210> SEQ ID NO 131
<211> LENGTH: 35
<212> TYPE: PRT
<213> ORGANISM: Macaca mulatta

<400> SEQUENCE: 131

Met Leu Glu Val Ile Phe Leu Val Asn Arg Pro Ser Lys Ile Cys Arg
1               5                   10                  15

Ala Pro Phe Thr Phe Cys Asn Leu Ser Leu Ala His Ala Cys Val Gly
            20                  25                  30

Leu Thr Glu
        35

<210> SEQ ID NO 132
<211> LENGTH: 15
<212> TYPE: PRT
<213> ORGANISM: Macaca mulatta

<400> SEQUENCE: 132

Met Leu Glu Val Met Phe Leu Val Asn Arg Gln Gly Lys Ile Cys
1               5                   10                  15

<210> SEQ ID NO 133
<211> LENGTH: 22
<212> TYPE: PRT
<213> ORGANISM: Macaca mulatta

<400> SEQUENCE: 133

Met Leu Glu Val Met Phe Leu Val Asn Arg Arg Gly Leu Ser Leu Pro
1               5                   10                  15

Ser Ser Phe Tyr Phe Phe
            20

<210> SEQ ID NO 134
<211> LENGTH: 15
<212> TYPE: PRT
<213> ORGANISM: Macaca mulatta

<400> SEQUENCE: 134

Met Leu Glu Val Met Phe Leu Val Asn Arg Gln Gly Lys Ile Cys
1               5                   10                  15

<210> SEQ ID NO 135

```
<211> LENGTH: 29
<212> TYPE: PRT
<213> ORGANISM: Macaca mulatta

<400> SEQUENCE: 135

Met Leu Glu Val Met Phe Leu Val Asn Arg Trp Gly Lys Ile Cys His
1               5                   10                  15

Val Pro Phe Thr Phe Leu Gln Ser Ser Leu Glu Asp Thr
            20                  25

<210> SEQ ID NO 136
<211> LENGTH: 22
<212> TYPE: PRT
<213> ORGANISM: Macaca mulatta

<400> SEQUENCE: 136

Met Leu Glu Val Met Phe Leu Val Asn Arg Arg Gly Leu Ser Leu Pro
1               5                   10                  15

Ser Ser Phe Tyr Phe Phe
            20

<210> SEQ ID NO 137
<211> LENGTH: 12
<212> TYPE: PRT
<213> ORGANISM: Macaca mulatta

<400> SEQUENCE: 137

Met Leu Glu Val Met Phe Leu Val Asn Arg Trp Gly
1               5                   10

<210> SEQ ID NO 138
<211> LENGTH: 22
<212> TYPE: PRT
<213> ORGANISM: Macaca mulatta

<400> SEQUENCE: 138

Met Leu Glu Val Met Phe Leu Val Asn Arg Arg Gly Leu Ser Leu Pro
1               5                   10                  15

Ser Ser Phe Tyr Leu Phe
            20

<210> SEQ ID NO 139
<211> LENGTH: 12
<212> TYPE: PRT
<213> ORGANISM: Macaca mulatta

<400> SEQUENCE: 139

Met Leu Glu Val Met Phe Leu Val Asn Arg Arg Gly
1               5                   10

<210> SEQ ID NO 140
<211> LENGTH: 35
<212> TYPE: PRT
<213> ORGANISM: Macaca mulatta

<400> SEQUENCE: 140

Met Leu Glu Val Met Phe Leu Val Asn Arg Trp Asp Lys Ile Cys Arg
1               5                   10                  15

Val Pro Phe Ser Phe Cys Asn Leu Ser Leu Glu His Ala Cys Val Gly
            20                  25                  30

Leu Ala Val
        35
```

```
<210> SEQ ID NO 141
<211> LENGTH: 32
<212> TYPE: PRT
<213> ORGANISM: Macaca mulatta

<400> SEQUENCE: 141

Met Leu Glu Val Met Phe Leu Val Ser Arg Trp Asp Lys Ile Cys Gln
1               5                   10                  15

Val Pro Phe Thr Phe Cys Tyr Leu Ser Leu Glu His Thr Cys Val Gly
            20                  25                  30

<210> SEQ ID NO 142
<211> LENGTH: 29
<212> TYPE: PRT
<213> ORGANISM: Macaca mulatta

<400> SEQUENCE: 142

Met Leu Gly Val Met Phe Leu Val Asn Arg Arg Gly Glu Ile Cys Arg
1               5                   10                  15

Val Ser Phe Thr Phe Cys Asn Leu Ser Leu Glu His Ala
            20                  25

<210> SEQ ID NO 143
<211> LENGTH: 15
<212> TYPE: PRT
<213> ORGANISM: Macaca mulatta

<400> SEQUENCE: 143

Met Leu Glu Val Met Phe Leu Val Asn Arg Gln Cys Lys Ile Cys
1               5                   10                  15

<210> SEQ ID NO 144
<211> LENGTH: 25
<212> TYPE: PRT
<213> ORGANISM: Macaca mulatta

<400> SEQUENCE: 144

Met Leu Glu Val Met Ile Ser Val Asn Arg Arg Leu Lys Phe Ala Glu
1               5                   10                  15

Phe Leu Leu Leu Phe Leu Thr Phe Pro
            20                  25

<210> SEQ ID NO 145
<211> LENGTH: 35
<212> TYPE: PRT
<213> ORGANISM: Macaca mulatta

<400> SEQUENCE: 145

Met Leu Glu Val Met Phe Leu Val Asn Arg Pro Gly Lys Ile Cys Gln
1               5                   10                  15

Val Pro Phe Thr Phe Phe Asn Leu Ser Leu Glu His Thr Cys Val Gly
            20                  25                  30

Ile Thr Val
        35

<210> SEQ ID NO 146
<211> LENGTH: 45
<212> TYPE: PRT
<213> ORGANISM: Macaca mulatta

<400> SEQUENCE: 146

Met Leu Asp Val Met Phe Leu Val Asn Arg Gln Gly Arg Ile Cys Gln
1               5                   10                  15
```

-continued

Val Pro Phe Thr Phe Cys Asn Val Ser Leu Glu His Ala Cys Val Gly
              20                  25                  30

Leu Thr Val Gln Ile Ile Gly Val Tyr Tyr Ile Tyr
         35                  40                  45

<210> SEQ ID NO 147
<211> LENGTH: 35
<212> TYPE: PRT
<213> ORGANISM: Macaca mulatta

<400> SEQUENCE: 147

Met Leu Glu Val Met Phe Leu Val Asn Arg Gln Gly Met Ile Cys Gln
1               5                   10                  15

Ile Pro Phe Thr Phe Cys Asn Ile Ser Leu Glu His Thr Cys Val Gly
              20                  25                  30

Leu Ile Val
         35

<210> SEQ ID NO 148
<211> LENGTH: 15
<212> TYPE: PRT
<213> ORGANISM: Macaca mulatta

<400> SEQUENCE: 148

Met Leu Glu Val Met Phe Leu Val Asn Arg Gln Ser Lys Ile Gly
1               5                   10                  15

<210> SEQ ID NO 149
<211> LENGTH: 12
<212> TYPE: PRT
<213> ORGANISM: Macaca mulatta

<400> SEQUENCE: 149

Met Leu Glu Val Met Phe Leu Val Asn Arg Gln Gly
1               5                   10

<210> SEQ ID NO 150
<211> LENGTH: 22
<212> TYPE: PRT
<213> ORGANISM: Macaca mulatta

<400> SEQUENCE: 150

Met Leu Glu Val Met Phe Leu Val Asn Arg Trp Gly Leu Ser Leu Pro
1               5                   10                  15

Ser Ser Phe Tyr Phe Phe
              20

<210> SEQ ID NO 151
<211> LENGTH: 12
<212> TYPE: PRT
<213> ORGANISM: Macaca mulatta

<400> SEQUENCE: 151

Met Leu Val Val Met Phe Leu Val Asn Arg Arg Gly
1               5                   10

<210> SEQ ID NO 152
<211> LENGTH: 25
<212> TYPE: PRT
<213> ORGANISM: Macaca mulatta

<400> SEQUENCE: 152

Met Leu Glu Val Met Phe Leu Val Asn Arg Trp Gly Lys Ile Ser Glu
1               5                   10                  15

```
Phe Leu Ile Leu Phe Val Ile Phe Pro
            20                  25

<210> SEQ ID NO 153
<211> LENGTH: 35
<212> TYPE: PRT
<213> ORGANISM: Macaca mulatta

<400> SEQUENCE: 153

Met Leu Glu Val Met Phe Leu Val Asn Arg Arg Gly Lys Ile Cys Gln
1               5                   10                  15

Val Pro Phe Thr Phe Cys Val Leu Ser Leu Gln His Ala Cys Val Gly
            20                  25                  30

Leu Thr Val
        35

<210> SEQ ID NO 154
<211> LENGTH: 26
<212> TYPE: PRT
<213> ORGANISM: Mus sp.

<400> SEQUENCE: 154

Met Leu Glu Val Met Phe Leu Val Asn Arg Arg Gly Ser Cys Leu Pro
1               5                   10                  15

Ser Ser Phe Tyr Leu Phe Gly Ser Phe Leu
            20                  25

<210> SEQ ID NO 155
<211> LENGTH: 25
<212> TYPE: PRT
<213> ORGANISM: Rattus sp.

<400> SEQUENCE: 155

Met Leu Glu Glu Met Phe Leu Val Asn Arg Arg Gly Ser Cys Leu Pro
1               5                   10                  15

Ser Ser Phe Thr Phe Leu Asn Phe Pro
            20                  25

<210> SEQ ID NO 156
<211> LENGTH: 33
<212> TYPE: PRT
<213> ORGANISM: Cavia sp.

<400> SEQUENCE: 156

Met Leu Glu Val Met Phe Leu Val Asn Arg Gln Asp Leu Cys Leu Pro
1               5                   10                  15

Ser Ser Phe Cys Phe Val Ser Ser Phe Leu Ser Ser Thr Pro Val Ser
            20                  25                  30

Asp

<210> SEQ ID NO 157
<211> LENGTH: 33
<212> TYPE: PRT
<213> ORGANISM: Cavia sp.

<400> SEQUENCE: 157

Met Leu Glu Val Met Phe Leu Val Ile Arg Arg Asp Leu Cys Leu Pro
1               5                   10                  15

Ser Ser Phe Cys Phe Val Ser Ser Phe Leu Ser Ser Thr Pro Val Ser
            20                  25                  30

Gly
```

```
<210> SEQ ID NO 158
<211> LENGTH: 29
<212> TYPE: PRT
<213> ORGANISM: Cavia sp.

<400> SEQUENCE: 158

Met Leu Glu Val Met Phe Leu Val Asn Arg Arg Asp Leu Cys Leu Pro
1               5                   10                  15

Cys Ser Phe Cys Leu Phe Phe Phe Val Phe Pro Glu
            20                  25

<210> SEQ ID NO 159
<211> LENGTH: 32
<212> TYPE: PRT
<213> ORGANISM: Cavia sp.

<400> SEQUENCE: 159

Met Leu Glu Val Met Phe Leu Val Asn Arg Gln Asp Leu Cys Leu Pro
1               5                   10                  15

Ser Ser Phe Cys Phe Leu Ser Phe Pro Ser Ser Thr Pro Met Ser Asp
            20                  25                  30

<210> SEQ ID NO 160
<211> LENGTH: 27
<212> TYPE: PRT
<213> ORGANISM: Cavia sp.

<400> SEQUENCE: 160

Met Leu Glu Val Val Phe Leu Val Lys Gln Ala Gly Phe Val Phe Ala
1               5                   10                  15

Glu Phe Leu Leu Leu Cys Phe Val Phe Pro Glu
            20                  25

<210> SEQ ID NO 161
<211> LENGTH: 25
<212> TYPE: PRT
<213> ORGANISM: Cavia sp.

<400> SEQUENCE: 161

Met Leu Glu Val Met Phe Leu Val Thr Gly Gly Ile Cys Val Cys Arg
1               5                   10                  15

Val Pro Phe Ala Leu Phe Cys Leu Ser
            20                  25

<210> SEQ ID NO 162
<211> LENGTH: 22
<212> TYPE: PRT
<213> ORGANISM: Unknown
<220> FEATURE:
<223> OTHER INFORMATION: Description of Unknown: Cat peptide

<400> SEQUENCE: 162

Met Leu Glu Val Met Phe Leu Val Asn Arg Arg Gly Leu Cys Leu Pro
1               5                   10                  15

Ser Ser Phe Tyr Phe Phe
            20

<210> SEQ ID NO 163
<211> LENGTH: 22
<212> TYPE: PRT
<213> ORGANISM: Unknown
<220> FEATURE:
<223> OTHER INFORMATION: Description of Unknown: Cat peptide
```

```
<400> SEQUENCE: 163

Met Leu Glu Val Met Phe Leu Val Asn Arg Arg Gly Leu His Leu Pro
1               5                   10                  15

Ser Ser Phe His Phe Leu
            20

<210> SEQ ID NO 164
<211> LENGTH: 39
<212> TYPE: PRT
<213> ORGANISM: Unknown
<220> FEATURE:
<223> OTHER INFORMATION: Description of Unknown: Cat polypeptide

<400> SEQUENCE: 164

Met Leu Glu Val Ile Leu Leu Val Asn Arg Trp Gly Leu Cys Ser Leu
1               5                   10                  15

Ser Ser Phe Tyr Phe Val Ser Ser Phe Leu Asp Cys Leu Ser Val Leu
            20                  25                  30

Gly Gln Gln Leu Val Trp Tyr
        35

<210> SEQ ID NO 165
<211> LENGTH: 22
<212> TYPE: PRT
<213> ORGANISM: Unknown
<220> FEATURE:
<223> OTHER INFORMATION: Description of Unknown: Cat peptide

<400> SEQUENCE: 165

Met Leu Glu Val Met Phe Ser Val Asn Arg Arg Asp Leu Cys Leu Pro
1               5                   10                  15

Ser Ser Phe Tyr Phe Phe
            20

<210> SEQ ID NO 166
<211> LENGTH: 22
<212> TYPE: PRT
<213> ORGANISM: Unknown
<220> FEATURE:
<223> OTHER INFORMATION: Description of Unknown: Cat peptide

<400> SEQUENCE: 166

Met Leu Glu Val Met Phe Leu Val Asn Arg Arg Gly Leu Cys Leu Pro
1               5                   10                  15

Ser Ser Phe Tyr Phe Phe
            20

<210> SEQ ID NO 167
<211> LENGTH: 22
<212> TYPE: PRT
<213> ORGANISM: Equus ferus

<400> SEQUENCE: 167

Met Leu Glu Val Met Phe Leu Val Asn Arg Arg Gly Leu Cys Leu Pro
1               5                   10                  15

Ser Ser Phe Tyr Phe Phe
            20

<210> SEQ ID NO 168
<211> LENGTH: 22
<212> TYPE: PRT
<213> ORGANISM: Equus ferus
```

```
<400> SEQUENCE: 168

Met Leu Glu Val Met Phe Ser Val Asn Met Arg Gly Leu Cys Leu Pro
1               5                   10                  15

Ser Ser Phe Tyr Phe Phe
            20

<210> SEQ ID NO 169
<211> LENGTH: 36
<212> TYPE: PRT
<213> ORGANISM: Equus ferus

<400> SEQUENCE: 169

Met Leu Glu Val Met Phe Leu Val Asn Arg Arg Ser Leu Cys Leu Leu
1               5                   10                  15

Ser Ser Phe Tyr Phe Phe Lys Ser Phe Leu Arg Val His Ala Cys Val
            20                  25                  30

Gly Leu Thr Val
        35

<210> SEQ ID NO 170
<211> LENGTH: 22
<212> TYPE: PRT
<213> ORGANISM: Ornithorhynchus anatinus

<400> SEQUENCE: 170

Met Leu Glu Ala Met Phe Leu Val Asn Arg Arg Asn Pro Ser Leu Pro
1               5                   10                  15

Ser Ser Phe Tyr Ser Phe
            20

<210> SEQ ID NO 171
<211> LENGTH: 34
<212> TYPE: PRT
<213> ORGANISM: Unknown
<220> FEATURE:
<223> OTHER INFORMATION: Description of Unknown: Fugu polypeptide

<400> SEQUENCE: 171

Met Phe Leu Val Asn Arg Arg Gly Phe Glu Phe Ala Glu Phe Leu Leu
1               5                   10                  15

Phe Leu Leu Val Phe Pro Ile Trp His Thr Ser Val Gly Val Thr Glu
            20                  25                  30

Lys Cys

<210> SEQ ID NO 172
<211> LENGTH: 23
<212> TYPE: PRT
<213> ORGANISM: Unknown
<220> FEATURE:
<223> OTHER INFORMATION: Description of Unknown: Stickleback peptide

<400> SEQUENCE: 172

Ile Gln Glu Ala Met Phe Leu Val Asn Arg Arg Gly Phe Met Cys Leu
1               5                   10                  15

Pro Ser Ser Phe Ser Phe Phe
            20

<210> SEQ ID NO 173
<211> LENGTH: 35
<212> TYPE: PRT
<213> ORGANISM: Oryzias latipes

<400> SEQUENCE: 173
```

```
Ile Ser Ser Leu Gln Glu Ala Met Phe Leu Val Asn Arg Arg Gly Leu
1               5                   10                  15

Val Tyr Leu Pro Ser Ser Phe Ser Phe Leu Ser Phe Leu Lys Ser
                20                  25                  30

Thr Pro Val
        35

<210> SEQ ID NO 174
<211> LENGTH: 51
<212> TYPE: PRT
<213> ORGANISM: Unknown
<220> FEATURE:
<223> OTHER INFORMATION: Description of Unknown: Lamprey polypeptide

<400> SEQUENCE: 174

Ile Leu Asp Phe Tyr Leu Glu Val Met Phe Leu Val Asn Arg Arg Gly
1               5                   10                  15

Met Cys Leu Pro Ser Ser Phe Leu Ser Phe Ile Ser Ser Ile Leu Cys
                20                  25                  30

Ser Ser Val Gly Leu Thr Val Ile Ser Ser Cys Phe Ser Cys Cys Cys
            35                  40                  45

Leu Cys Phe
    50

<210> SEQ ID NO 175
<211> LENGTH: 24
<212> TYPE: PRT
<213> ORGANISM: Pan sp.

<400> SEQUENCE: 175

Met Tyr Cys Ser Glu Val Gly Leu Cys Ser Glu Val Ala Pro Thr Glu
1               5                   10                  15

Ile Phe Asn Ala Gly Leu Ile Val
                20

<210> SEQ ID NO 176
<211> LENGTH: 24
<212> TYPE: PRT
<213> ORGANISM: Pongo sp.

<400> SEQUENCE: 176

Met Cys Phe Ser Glu Val Gly Leu Cys Ser Glu Val Ala Pro Thr Glu
1               5                   10                  15

Ile Phe Ser Ala Gly Leu Val Ile
                20

<210> SEQ ID NO 177
<211> LENGTH: 37
<212> TYPE: PRT
<213> ORGANISM: Gallus gallus

<400> SEQUENCE: 177

Val Gly Leu Glu Asp Phe Phe Phe Ser Lys Val Ala Pro Thr Glu Lys
1               5                   10                  15

Cys Arg Pro Gly Val Tyr Val Trp Val Asp Pro Val Gly Leu Cys Lys
                20                  25                  30

Val Val Arg Trp Ser
        35

<210> SEQ ID NO 178
<211> LENGTH: 20
```

```
<212> TYPE: PRT
<213> ORGANISM: Pan sp.

<400> SEQUENCE: 178

Met Leu Asp Gln Asp Ile Pro Met Val Gln Pro Leu Leu Lys Val Arg
1               5                   10                  15

Leu Phe Asn Asp
            20

<210> SEQ ID NO 179
<211> LENGTH: 20
<212> TYPE: PRT
<213> ORGANISM: Pan sp.

<400> SEQUENCE: 179

Met Leu Asp Gln Asp Ile Pro Met Val Gln Pro Leu Leu Lys Val Arg
1               5                   10                  15

Leu Phe Asn Asp
            20

<210> SEQ ID NO 180
<211> LENGTH: 23
<212> TYPE: PRT
<213> ORGANISM: Pan sp.

<400> SEQUENCE: 180

Met Leu Asp Gln Asp Met Leu Met Val Gln Pro Leu Ser Lys Val Arg
1               5                   10                  15

Leu Phe Asn Asp Cys Thr Ser
            20

<210> SEQ ID NO 181
<211> LENGTH: 20
<212> TYPE: PRT
<213> ORGANISM: Pan sp.

<400> SEQUENCE: 181

Met Leu Asp Gln Asp Ile Leu Met Val Gln Leu Leu Leu Arg Val Cys
1               5                   10                  15

Phe Phe Ser Asp
            20

<210> SEQ ID NO 182
<211> LENGTH: 20
<212> TYPE: PRT
<213> ORGANISM: Pan sp.

<400> SEQUENCE: 182

Met Leu Asp Gln Asp Ile Pro Met Val Gln Pro Leu Leu Lys Val Arg
1               5                   10                  15

Leu Phe Asn Asp
            20

<210> SEQ ID NO 183
<211> LENGTH: 20
<212> TYPE: PRT
<213> ORGANISM: Pan sp.

<400> SEQUENCE: 183

Met Leu Asp Gln Asp Ile Leu Met Val Gln Pro Leu Leu Lys Val Arg
1               5                   10                  15

Leu Phe Asn Asp
            20
```

<210> SEQ ID NO 184
<211> LENGTH: 20
<212> TYPE: PRT
<213> ORGANISM: Pan sp.

<400> SEQUENCE: 184

Met Leu Asp Gln Asp Ile Pro Met Val Gln Pro Leu Leu Lys Val Arg
1               5                   10                  15

Leu Phe Asn Asp
            20

<210> SEQ ID NO 185
<211> LENGTH: 20
<212> TYPE: PRT
<213> ORGANISM: Pan sp.

<400> SEQUENCE: 185

Met Leu Asp Gln Asp Ile Leu Met Val Gln Pro Val Leu Arg Val Arg
1               5                   10                  15

Leu Phe Asn Asp
            20

<210> SEQ ID NO 186
<211> LENGTH: 20
<212> TYPE: PRT
<213> ORGANISM: Pongo sp.

<400> SEQUENCE: 186

Met Leu Asp Gln Asp Ile Leu Met Val Gln Pro Leu Leu Lys Val Arg
1               5                   10                  15

Leu Phe Asn Asp
            20

<210> SEQ ID NO 187
<211> LENGTH: 9
<212> TYPE: PRT
<213> ORGANISM: Pongo sp.

<400> SEQUENCE: 187

Met Leu Asp Gln Asp Ile Leu Met Val
1               5

<210> SEQ ID NO 188
<211> LENGTH: 23
<212> TYPE: PRT
<213> ORGANISM: Pongo sp.

<400> SEQUENCE: 188

Met Leu Asp Gln Asp Ile Leu Met Val Gln Pro Leu Ser Lys Phe His
1               5                   10                  15

Leu Phe Asn Asn Cys Thr Ser
            20

<210> SEQ ID NO 189
<211> LENGTH: 9
<212> TYPE: PRT
<213> ORGANISM: Pongo sp.

<400> SEQUENCE: 189

Met Leu Asp His Val Ile Leu Met Val
1               5

```
<210> SEQ ID NO 190
<211> LENGTH: 9
<212> TYPE: PRT
<213> ORGANISM: Pongo sp.

<400> SEQUENCE: 190

Met Leu Asp Gln Asp Ile Leu Met Val
1               5

<210> SEQ ID NO 191
<211> LENGTH: 9
<212> TYPE: PRT
<213> ORGANISM: Pongo sp.

<400> SEQUENCE: 191

Met Leu Asp Gln Asp Ile Leu Met Val
1               5

<210> SEQ ID NO 192
<211> LENGTH: 20
<212> TYPE: PRT
<213> ORGANISM: Pongo sp.

<400> SEQUENCE: 192

Met Leu Asp Gln Asp Ile Pro Met Val Gln Pro Leu Leu Lys Val Arg
1               5                   10                  15

Leu Phe Asn Asp
            20

<210> SEQ ID NO 193
<211> LENGTH: 9
<212> TYPE: PRT
<213> ORGANISM: Pongo sp.

<400> SEQUENCE: 193

Met Leu Asp Gln Asp Ile Leu Met Val
1               5

<210> SEQ ID NO 194
<211> LENGTH: 9
<212> TYPE: PRT
<213> ORGANISM: Pongo sp.

<400> SEQUENCE: 194

Met Leu Asp Gln Asp Ile Leu Met Val
1               5

<210> SEQ ID NO 195
<211> LENGTH: 20
<212> TYPE: PRT
<213> ORGANISM: Pongo sp.

<400> SEQUENCE: 195

Met Leu Asp Gln Asp Ile Leu Met Val Gln Pro Leu Leu Lys Val Arg
1               5                   10                  15

Leu Phe Asn Asp
            20

<210> SEQ ID NO 196
<211> LENGTH: 20
<212> TYPE: PRT
<213> ORGANISM: Pongo sp.

<400> SEQUENCE: 196

Met Leu Asp Gln Asp Ile Leu Met Val Gln Pro Leu Leu Arg Val Arg
```

-continued

```
                1               5                  10                 15
Leu Phe Asn Asp
            20

<210> SEQ ID NO 197
<211> LENGTH: 20
<212> TYPE: PRT
<213> ORGANISM: Pongo sp.

<400> SEQUENCE: 197

Met Leu Asp Gln Asp Ile Pro Arg Val Gln Leu Leu Leu Lys Phe Arg
1               5                   10                  15

Leu Phe Asn Asp
            20

<210> SEQ ID NO 198
<211> LENGTH: 20
<212> TYPE: PRT
<213> ORGANISM: Macaca mulatta

<400> SEQUENCE: 198

Met Leu Asp Gln Asp Ile Leu Met Val Gln Gln Leu Ser Arg Val Arg
1               5                   10                  15

Leu Phe Asn Asp
            20

<210> SEQ ID NO 199
<211> LENGTH: 9
<212> TYPE: PRT
<213> ORGANISM: Macaca mulatta

<400> SEQUENCE: 199

Met Leu His Gln Asp Ile Leu Met Val
1               5

<210> SEQ ID NO 200
<211> LENGTH: 20
<212> TYPE: PRT
<213> ORGANISM: Macaca mulatta

<400> SEQUENCE: 200

Met Leu Asp Gln Asp Ile Leu Met Val Gln Gln Leu Ser Arg Val Leu
1               5                   10                  15

Leu Phe Asn Asn
            20

<210> SEQ ID NO 201
<211> LENGTH: 9
<212> TYPE: PRT
<213> ORGANISM: Macaca mulatta

<400> SEQUENCE: 201

Met Leu Asp Gln Asp Ile Leu Met Val
1               5

<210> SEQ ID NO 202
<211> LENGTH: 9
<212> TYPE: PRT
<213> ORGANISM: Mus sp.

<400> SEQUENCE: 202

Met Leu Asp Gln Asp Ile Pro Met Val
1               5
```

<210> SEQ ID NO 203
<211> LENGTH: 20
<212> TYPE: PRT
<213> ORGANISM: Rattus sp.

<400> SEQUENCE: 203

Met Leu Asp Gln Asp Ile Pro Met Val Gln Lys Leu Leu Met Val Arg
1               5                   10                  15

Leu Phe Asn Asp
            20

<210> SEQ ID NO 204
<211> LENGTH: 20
<212> TYPE: PRT
<213> ORGANISM: Unknown
<220> FEATURE:
<223> OTHER INFORMATION: Description of Unknown: Opossum peptide

<400> SEQUENCE: 204

Met Leu Asp Gln Asp Thr Pro Met Val Gln Pro Leu Leu Lys Val Arg
1               5                   10                  15

Leu Phe Asn Asp
            20

<210> SEQ ID NO 205
<211> LENGTH: 20
<212> TYPE: PRT
<213> ORGANISM: Ornithorhynchus anatinus

<400> SEQUENCE: 205

Met Leu Asp Gln Asp Ile Gln Met Val Gln Pro Leu Leu Met Val Arg
1               5                   10                  15

Leu Phe Asn Asp
            20

<210> SEQ ID NO 206
<211> LENGTH: 20
<212> TYPE: PRT
<213> ORGANISM: Cavia sp.

<400> SEQUENCE: 206

Met Leu Asp Gln Asp Ile Leu Met Val Gln Gln Leu Leu Arg Val Arg
1               5                   10                  15

Leu Phe Asn Asp
            20

<210> SEQ ID NO 207
<211> LENGTH: 20
<212> TYPE: PRT
<213> ORGANISM: Cavia sp.

<400> SEQUENCE: 207

Met Leu Asp Leu Val Ile Leu Met Val Gln Pro Leu Ser Arg Val Arg
1               5                   10                  15

Leu Phe Asn Asp
            20

<210> SEQ ID NO 208
<211> LENGTH: 20
<212> TYPE: PRT
<213> ORGANISM: Cavia sp.

<400> SEQUENCE: 208

Met Leu Asp Gln Asp Val Leu Met Gly Gln Pro Leu Ser Val Arg
1               5                   10                  15

Leu Phe Asn Asp
            20

<210> SEQ ID NO 209
<211> LENGTH: 20
<212> TYPE: PRT
<213> ORGANISM: Cavia sp.

<400> SEQUENCE: 209

Met Leu Asp Gln Asp Ile Leu Met Val Arg Arg Leu Leu Arg Val His
1               5                   10                  15

Leu Phe Asn Asp
            20

<210> SEQ ID NO 210
<211> LENGTH: 20
<212> TYPE: PRT
<213> ORGANISM: Cavia sp.

<400> SEQUENCE: 210

Met Leu Asp Gln Asp Ile Leu Met Val Gln Gln Leu Leu Arg Val Arg
1               5                   10                  15

Leu Phe Asn Asp
            20

<210> SEQ ID NO 211
<211> LENGTH: 20
<212> TYPE: PRT
<213> ORGANISM: Unknown
<220> FEATURE:
<223> OTHER INFORMATION: Description of Unknown: Cat peptide

<400> SEQUENCE: 211

Met Leu Asp Gln Asp Ile Pro Met Val Gln Gln Leu Ser Lys Val Arg
1               5                   10                  15

Leu Phe Asn Asp
            20

<210> SEQ ID NO 212
<211> LENGTH: 20
<212> TYPE: PRT
<213> ORGANISM: Unknown
<220> FEATURE:
<223> OTHER INFORMATION: Description of Unknown: Cat peptide

<400> SEQUENCE: 212

Met Leu Asp Gln Asp Ile Pro Ile Val Gln Gln Leu Ser Lys Val Cys
1               5                   10                  15

Leu Phe Asn Asp
            20

<210> SEQ ID NO 213
<211> LENGTH: 20
<212> TYPE: PRT
<213> ORGANISM: Unknown
<220> FEATURE:
<223> OTHER INFORMATION: Description of Unknown: Cat peptide

<400> SEQUENCE: 213

Met Leu Asp Gln Asp Ile Pro Ile Val Gln Gln Leu Ser Lys Val Cys
1               5                   10                  15

Leu Phe Asn Asp

-continued

<210> SEQ ID NO 214
<211> LENGTH: 24
<212> TYPE: PRT
<213> ORGANISM: Unknown
<220> FEATURE:
<223> OTHER INFORMATION: Description of Unknown: Cat peptide

<400> SEQUENCE: 214

Met Leu Asp Gln Asp Ile Pro Met Val Gln Gln Leu Ser Lys Phe Arg
1               5                   10                  15

Leu Phe Asn Asn Ser Ser Pro Thr
            20

<210> SEQ ID NO 215
<211> LENGTH: 20
<212> TYPE: PRT
<213> ORGANISM: Unknown
<220> FEATURE:
<223> OTHER INFORMATION: Description of Unknown: Cat peptide

<400> SEQUENCE: 215

Met Leu Asp Gln Asp Ile Pro Met Val Gln Gln Leu Ala Lys Val Arg
1               5                   10                  15

Leu Leu Asp Asp
            20

<210> SEQ ID NO 216
<211> LENGTH: 20
<212> TYPE: PRT
<213> ORGANISM: Canis lupus

<400> SEQUENCE: 216

Met Leu Asp Gln Asp Ile Leu Met Val Gln Gln Leu Leu Arg Val Arg
1               5                   10                  15

Leu Phe Asn Asp
            20

<210> SEQ ID NO 217
<211> LENGTH: 20
<212> TYPE: PRT
<213> ORGANISM: Canis lupus

<400> SEQUENCE: 217

Met Leu Asp Gln Asp Ile Leu Met Val Gln Gln Leu Leu Arg Val Ser
1               5                   10                  15

Leu Phe Asn Asn
            20

<210> SEQ ID NO 218
<211> LENGTH: 20
<212> TYPE: PRT
<213> ORGANISM: Equus ferus

<400> SEQUENCE: 218

Met Leu Asp Gln Asp Ile Leu Met Val Gln Pro Leu Leu Arg Val Arg
1               5                   10                  15

Leu Phe Asn Asp
            20

<210> SEQ ID NO 219
<211> LENGTH: 20
<212> TYPE: PRT

-continued

<213> ORGANISM: Equus ferus

<400> SEQUENCE: 219

Met Leu Asp Gln Asp Ile Leu Met Val Gln Pro Leu Arg Val Cys
1               5                   10                  15

Leu Phe Asn Asp
            20

<210> SEQ ID NO 220
<211> LENGTH: 20
<212> TYPE: PRT
<213> ORGANISM: Bos sp.

<400> SEQUENCE: 220

Met Leu Asp Gln Asp Ile Leu Met Val Gln Pro Leu Ser Lys Val Arg
1               5                   10                  15

Leu Phe Asn Asp
            20

<210> SEQ ID NO 221
<211> LENGTH: 20
<212> TYPE: PRT
<213> ORGANISM: Gallus gallus

<400> SEQUENCE: 221

Met Leu Asp Gln Asp Asn Leu Met Val Gln Pro Leu Leu Arg Val Arg
1               5                   10                  15

Leu Phe Asn Asp
            20

<210> SEQ ID NO 222
<211> LENGTH: 20
<212> TYPE: PRT
<213> ORGANISM: Taeniopygia guttata

<400> SEQUENCE: 222

Met Leu Asp Gln Asp Ile Leu Val Val Gln Pro Leu Leu Arg Val Arg
1               5                   10                  15

Leu Phe Asn Asp
            20

<210> SEQ ID NO 223
<211> LENGTH: 26
<212> TYPE: PRT
<213> ORGANISM: Taeniopygia guttata

<400> SEQUENCE: 223

Met Leu Asp Gln Asp Ile Leu Val Val Gln Pro Leu Leu Arg Val Arg
1               5                   10                  15

Leu Phe Asn Asp Leu Gln Ser Tyr Val Ile
            20                  25

<210> SEQ ID NO 224
<211> LENGTH: 20
<212> TYPE: PRT
<213> ORGANISM: Unknown
<220> FEATURE:
<223> OTHER INFORMATION: Description of Unknown: Lizard peptide

<400> SEQUENCE: 224

Met Leu Asp Gln Asp Thr Gln Met Val Gln Pro Leu Leu Lys Val Arg
1               5                   10                  15

Leu Phe Asn Asp

```
<210> SEQ ID NO 225
<211> LENGTH: 20
<212> TYPE: PRT
<213> ORGANISM: Xenopus tropicalis

<400> SEQUENCE: 225

Met Leu Asp Gln Gly Ile Pro Val Val Gln Pro Leu Leu Lys Val Arg
1               5                   10                  15

Leu Phe Asn Asp
            20

<210> SEQ ID NO 226
<211> LENGTH: 20
<212> TYPE: PRT
<213> ORGANISM: Danio rerio

<400> SEQUENCE: 226

Met Leu Asp Gln Asp Ile Leu Met Val Gln Pro Leu Leu Arg Val Arg
1               5                   10                  15

Leu Phe Asn Asp
            20

<210> SEQ ID NO 227
<211> LENGTH: 20
<212> TYPE: PRT
<213> ORGANISM: Tetraodon sp.

<400> SEQUENCE: 227

Met Leu Asp Gln Asp Ile Leu Met Val Gln Pro Leu Leu Arg Val Arg
1               5                   10                  15

Leu Phe Asn Asp
            20

<210> SEQ ID NO 228
<211> LENGTH: 20
<212> TYPE: PRT
<213> ORGANISM: Unknown
<220> FEATURE:
<223> OTHER INFORMATION: Description of Unknown: Fugu peptide

<400> SEQUENCE: 228

Met Leu Asp Gln Asp Ile Leu Met Val Gln Pro Leu Leu Lys Val Arg
1               5                   10                  15

Leu Phe Asn Asp
            20

<210> SEQ ID NO 229
<211> LENGTH: 20
<212> TYPE: PRT
<213> ORGANISM: Unknown
<220> FEATURE:
<223> OTHER INFORMATION: Description of Unknown: Stickleback peptide

<400> SEQUENCE: 229

Met Leu Asp Gln Asp Ile Leu Met Val Gln Pro Leu Leu Arg Val Arg
1               5                   10                  15

Leu Phe Asn Asp
            20

<210> SEQ ID NO 230
<211> LENGTH: 20
<212> TYPE: PRT
```

<213> ORGANISM: Oryzias latipes

<400> SEQUENCE: 230

Met Leu Asp Gln Asp Ile Leu Met Val Gln Pro Leu Leu Arg Val Cys
1               5                   10                  15

Leu Phe Asn Asn
            20

<210> SEQ ID NO 231
<211> LENGTH: 20
<212> TYPE: PRT
<213> ORGANISM: Unknown
<220> FEATURE:
<223> OTHER INFORMATION: Description of Unknown: Lamprey peptide

<400> SEQUENCE: 231

Met Leu Asp Arg Gly Thr Pro Met Ala Gln Lys Leu Leu Lys Val Arg
1               5                   10                  15

Leu Phe Asn Asp
            20

<210> SEQ ID NO 232
<211> LENGTH: 75
<212> TYPE: DNA
<213> ORGANISM: Pan sp.

<400> SEQUENCE: 232
ttaccccgcc tgtttaccaa aaacatcacc tctagcatta ccagtattag aggcaccgcc      60
tgcccggtga catat                                                       75

<210> SEQ ID NO 233
<211> LENGTH: 75
<212> TYPE: DNA
<213> ORGANISM: Pongo sp.

<400> SEQUENCE: 233
tcaccccgcc tgtttaccaa aaacatcacc tctagcatta ccagtattag aggcaccgcc      60
tgcccggtga cacat                                                       75

<210> SEQ ID NO 234
<211> LENGTH: 70
<212> TYPE: DNA
<213> ORGANISM: Unknown
<220> FEATURE:
<223> OTHER INFORMATION: Description of Unknown: Cat oligonucleotide

<400> SEQUENCE: 234
accccgcctg tttaccaata acatcacctc tagcattttt agtattaagg cacggcctgc      60
ccagggacat                                                             70

<210> SEQ ID NO 235
<211> LENGTH: 81
<212> TYPE: DNA
<213> ORGANISM: Pan sp.

<400> SEQUENCE: 235
ttaactgtta gtccaaagag gaacagctct ttagacacta ggaaaaaacc ttgtaaagag      60
agtaaaaaat ttaacaccca t                                                81

<210> SEQ ID NO 236
<211> LENGTH: 81
<212> TYPE: DNA

<213> ORGANISM: Pan sp.

<400> SEQUENCE: 236
ttaactgtta gtccaaagag gaacagctct ttagacacta ggaaaaaacc ttgtaaagag    60
agtaaaaaat ttaacaccca t                                              81

<210> SEQ ID NO 237
<211> LENGTH: 81
<212> TYPE: DNA
<213> ORGANISM: Pan sp.

<400> SEQUENCE: 237
ttaactgtta gtccaaagag gaacagctct ttggacacta ggaaaaaacc ttgtaaagag    60
agtaaaaaat ttaataccca t                                              81

<210> SEQ ID NO 238
<211> LENGTH: 81
<212> TYPE: DNA
<213> ORGANISM: Pan sp.

<400> SEQUENCE: 238
ttaactgtta gtccaaagag gaacagctct ttggacacta ggaaaaaaac ttgtaaagag    60
agtaaaaaat ttaataccca t                                              81

<210> SEQ ID NO 239
<211> LENGTH: 73
<212> TYPE: DNA
<213> ORGANISM: Pongo sp.

<400> SEQUENCE: 239
tagtctaaag aggaacagct ctttagacac taggaaaaaa ccttaaaaag agagtaaaaa    60
acacaacacc cat                                                       73

<210> SEQ ID NO 240
<211> LENGTH: 72
<212> TYPE: DNA
<213> ORGANISM: Pongo sp.
<220> FEATURE:
<221> NAME/KEY: modified_base
<222> LOCATION: (55)..(55)
<223> OTHER INFORMATION: a, c, g, t

<400> SEQUENCE: 240
tagtctaaag aggaacagct ctttagacac taggaaaaac cttgaaaaga gagtnaaaaa    60
cacaacaccc at                                                        72

<210> SEQ ID NO 241
<211> LENGTH: 77
<212> TYPE: DNA
<213> ORGANISM: Pan sp.

<400> SEQUENCE: 241
aaggaaaggt taaaaaaagt aaaaggaact cggcaaatct taccccgcct gtttaccaaa    60
aacatcacct ctagcat                                                   77

<210> SEQ ID NO 242
<211> LENGTH: 78
<212> TYPE: DNA
<213> ORGANISM: Pan sp.

<400> SEQUENCE: 242

```
taaggaaaga ttacaaaaag taaaaggaac tctgcaaatc ttactcggtc tgtttaccaa      60
aaatatcacc tctagcat                                                    78

<210> SEQ ID NO 243
<211> LENGTH: 78
<212> TYPE: DNA
<213> ORGANISM: Pan sp.

<400> SEQUENCE: 243
taaggaaaga ttacaaaaag taaaaggaaa tcggcaaatc ttaccttgcc tgtttaccaa      60
aaacaccacc tctagcat                                                    78

<210> SEQ ID NO 244
<211> LENGTH: 78
<212> TYPE: DNA
<213> ORGANISM: Pan sp.

<400> SEQUENCE: 244
taaggaaagt ttacaacaag taaaaggaac tcagcaaatc ttaccctgcc tgtttaccaa      60
aaacatcacc tctagcat                                                    78

<210> SEQ ID NO 245
<211> LENGTH: 78
<212> TYPE: DNA
<213> ORGANISM: Pan sp.

<400> SEQUENCE: 245
taaggaaaga ttgcaaaaag taagaggaac atgacaaatc ttaccccacc tgtttaccaa      60
aaacatcacc tctagcat                                                    78

<210> SEQ ID NO 246
<211> LENGTH: 76
<212> TYPE: DNA
<213> ORGANISM: Pan sp.

<400> SEQUENCE: 246
aaggaaaggt taaaaaagt aattgaactc ggcaaatctt accccgcctg tttaccaaaa       60
acctcacctc tagcat                                                      76

<210> SEQ ID NO 247
<211> LENGTH: 80
<212> TYPE: DNA
<213> ORGANISM: Pan sp.

<400> SEQUENCE: 247
cataaggaaa ggttaaaaaa agtaaaagga actcggcaaa tcttaccccg cctgtttacc      60
aaaaacatca cctctagcat                                                  80

<210> SEQ ID NO 248
<211> LENGTH: 81
<212> TYPE: DNA
<213> ORGANISM: Pan sp.

<400> SEQUENCE: 248
ttataaggaa aggttaaaaa aagtaaaagg aactcggcaa atcttacccc gcctgtttac      60
caaaaacatc acctctagca t                                                81

<210> SEQ ID NO 249
<211> LENGTH: 79
<212> TYPE: DNA
```

<213> ORGANISM: Pan sp.

<400> SEQUENCE: 249
taaggaaagg ttaaaaaaaa ttaaaaggaa ctcggcaaat tttaccctgc ctgtttacca    60
aaaacatcac ctctagcat    79

<210> SEQ ID NO 250
<211> LENGTH: 78
<212> TYPE: DNA
<213> ORGANISM: Pan sp.

<400> SEQUENCE: 250
taaggaaaga ttacaaaaac taaaaggaac tctgcaagtc ttaccctgcc tgtttaccaa    60
aaacatcacc tctagcat    78

<210> SEQ ID NO 251
<211> LENGTH: 78
<212> TYPE: DNA
<213> ORGANISM: Pan sp.

<400> SEQUENCE: 251
taaggaaaaa ttacaaaaag tgaaaggaac ttggcaaatc ttgtcccgcc tatttaccaa    60
aaacatcacc tctagcat    78

<210> SEQ ID NO 252
<211> LENGTH: 78
<212> TYPE: DNA
<213> ORGANISM: Pan sp.

<400> SEQUENCE: 252
taaggaagga ctgcaaaaag taaaaagaac tcgacaaatc ataccctgcc tgtttaccaa    60
aaacatcacc tctagcat    78

<210> SEQ ID NO 253
<211> LENGTH: 77
<212> TYPE: DNA
<213> ORGANISM: Pan sp.

<400> SEQUENCE: 253
aaggaaaggt taaaaaaagt aaaaggaact cggcaaatct taccccgcct gtttaccaaa    60
aacatcacct ctagcat    77

<210> SEQ ID NO 254
<211> LENGTH: 78
<212> TYPE: DNA
<213> ORGANISM: Pan sp.

<400> SEQUENCE: 254
taaggaaata ttacaaaaag taaaaggaac tcggcaaatc ttaccctacc tgtttaccaa    60
aaacatcacc tctagcat    78

<210> SEQ ID NO 255
<211> LENGTH: 78
<212> TYPE: DNA
<213> ORGANISM: Pan sp.

<400> SEQUENCE: 255
taaggaaaga ttacaaaaag taaaaggaat tcagccaatc ttaccccgcc tgtttaccaa    60
aaacatcacc tgtagcat    78

```
<210> SEQ ID NO 256
<211> LENGTH: 77
<212> TYPE: DNA
<213> ORGANISM: Pan sp.

<400> SEQUENCE: 256
aaggaaaggt taaaaaaagt aaaaggaact cggcaaatct taccccgcct gtttaccaaa      60
aacatcacct ctagcat                                                    77

<210> SEQ ID NO 257
<211> LENGTH: 77
<212> TYPE: DNA
<213> ORGANISM: Pan sp.

<400> SEQUENCE: 257
aaggaaaggt taaaaaaagt aaaaggaact cggcaaacct taccccgcct gtttaccaaa      60
aacatcacct ctagcat                                                    77

<210> SEQ ID NO 258
<211> LENGTH: 77
<212> TYPE: DNA
<213> ORGANISM: Pan sp.

<400> SEQUENCE: 258
aaggaaaggt taaaaaaagt aaaaggaact cggcaaatct taccccacct gcttaccaaa      60
aacatcacct ctagcat                                                    77

<210> SEQ ID NO 259
<211> LENGTH: 78
<212> TYPE: DNA
<213> ORGANISM: Pan sp.

<400> SEQUENCE: 259
taaggaaaga ttacaaacag taaaaggaac tcggcaaatc ttacccagct tgtttaccaa      60
aaacatcacc tctagcat                                                   78

<210> SEQ ID NO 260
<211> LENGTH: 78
<212> TYPE: DNA
<213> ORGANISM: Pan sp.

<400> SEQUENCE: 260
taaggaaata ttacaaaaag taaaaggaac tcggcaaatc ttaccctacc tgtttaccaa      60
aaacatcacc tctagcat                                                   78

<210> SEQ ID NO 261
<211> LENGTH: 78
<212> TYPE: DNA
<213> ORGANISM: Pan sp.

<400> SEQUENCE: 261
taaggaaaga atacaaaaag taaaaggaac tccgcaaatt ttaccccgcc tgtttaccaa      60
aaacatcacc tctagcat                                                   78

<210> SEQ ID NO 262
<211> LENGTH: 78
<212> TYPE: DNA
<213> ORGANISM: Pan sp.

<400> SEQUENCE: 262
```

-continued taaggaaaga ttacaaaaac taaaaggaac tcagcaaatc gtaccctgcc tgtttaccaa    60
aaacatcacc tctagcat                                                  78

<210> SEQ ID NO 263
<211> LENGTH: 78
<212> TYPE: DNA
<213> ORGANISM: Pan sp.

<400> SEQUENCE: 263
taaggaaaga ttacaaaaac taaaaggaac tcagcaaatc gtaccctgcc tgtttaccaa    60
aaacatcacc tctagcat                                                  78

<210> SEQ ID NO 264
<211> LENGTH: 78
<212> TYPE: DNA
<213> ORGANISM: Pan sp.

<400> SEQUENCE: 264
taaggaaaga ttacaaaaac taaaaggaac tcagcaaatc gtaccctgcc tgtttaccaa    60
aaacatcacc tctagcat                                                  78

<210> SEQ ID NO 265
<211> LENGTH: 79
<212> TYPE: DNA
<213> ORGANISM: Pongo sp.

<400> SEQUENCE: 265
ataaggaaag gttaaaaaaa gtaaaggaa ctcggcaaat ctcaccccgc ctgtttacca    60
aaaacatcac ctctagcat                                                 79

<210> SEQ ID NO 266
<211> LENGTH: 78
<212> TYPE: DNA
<213> ORGANISM: Pongo sp.

<400> SEQUENCE: 266
taaggaaaga ttacaaaaag taaaaggaac tcagcaaatc ataccctgac tgtttaccaa    60
aaacatcacc tctagcat                                                  78

<210> SEQ ID NO 267
<211> LENGTH: 78
<212> TYPE: DNA
<213> ORGANISM: Pongo sp.

<400> SEQUENCE: 267
taaggaaaga ttacaaaaag taaaaggaaa tcggcaaatc ttaccttgcc tgtttaccaa    60
aaacaccatc tctagcat                                                  78

<210> SEQ ID NO 268
<211> LENGTH: 78
<212> TYPE: DNA
<213> ORGANISM: Pongo sp.

<400> SEQUENCE: 268
taaggaaaga ttgcaaaaag taagaggaac acgacaaatc ttaccccacc tgtttaccaa    60
aaacatcacc tctagcat                                                  78

<210> SEQ ID NO 269
<211> LENGTH: 78
<212> TYPE: DNA

<213> ORGANISM: Pongo sp.

<400> SEQUENCE: 269
taaggaaaga ttgcaaaaag taagaggaac acgacaaatc ttaccccacc tgtttaccaa    60
gaacatcacc tctagcat                                                  78

<210> SEQ ID NO 270
<211> LENGTH: 76
<212> TYPE: DNA
<213> ORGANISM: Pongo sp.

<400> SEQUENCE: 270
aggaaaggtt aaaaaagta aaggaactt ggcaaatctt accctgcctg tttaccaaaa      60
acatcacctc tagcat                                                    76

<210> SEQ ID NO 271
<211> LENGTH: 78
<212> TYPE: DNA
<213> ORGANISM: Pongo sp.

<400> SEQUENCE: 271
taaggaaagg ttaaaaagag taaaaggaac tcggcaaatt ttaccctgcc tgtttaccaa    60
aaacatcacc tctagcat                                                  78

<210> SEQ ID NO 272
<211> LENGTH: 78
<212> TYPE: DNA
<213> ORGANISM: Pongo sp.

<400> SEQUENCE: 272
taaggaaaaa ttacaaaaag taaaaggaac ttggcaaatc ttatcccacc tatttaccaa    60
aaacatcacc tctagcat                                                  78

<210> SEQ ID NO 273
<211> LENGTH: 74
<212> TYPE: DNA
<213> ORGANISM: Pongo sp.

<400> SEQUENCE: 273
taaggaaata ttcaaaaaaa aggaactagg caaatcttac cccacctgtt taccaaaaac    60
atcacctcta gcat                                                      74

<210> SEQ ID NO 274
<211> LENGTH: 78
<212> TYPE: DNA
<213> ORGANISM: Pongo sp.

<400> SEQUENCE: 274
taaggaaaga ttacaaaaag taaaaggaat tcagcaaatc ttaccccgac tgtttaccaa    60
aaacatcacc tctagcat                                                  78

<210> SEQ ID NO 275
<211> LENGTH: 78
<212> TYPE: DNA
<213> ORGANISM: Pongo sp.

<400> SEQUENCE: 275
taaggaaaga ttacaaaaag taaaaggaac tcagcacatt tcactccgtc tctttaccaa    60
aaacatcacc cctagcat                                                  78

```
<210> SEQ ID NO 276
<211> LENGTH: 77
<212> TYPE: DNA
<213> ORGANISM: Pongo sp.

<400> SEQUENCE: 276
aaggaaaggt tacaaaaagt aaaggaact cagcaaatct taccctgcct gtttaccaaa    60
aacatcacct ctagcat                                                  77

<210> SEQ ID NO 277
<211> LENGTH: 76
<212> TYPE: DNA
<213> ORGANISM: Pongo sp.

<400> SEQUENCE: 277
aggaaaggtt aaaaaagta aaggaactc ggcaaatctc accccgcctg tttaccaaaa    60
acatcacctc tagcat                                                   76

<210> SEQ ID NO 278
<211> LENGTH: 79
<212> TYPE: DNA
<213> ORGANISM: Pongo sp.

<400> SEQUENCE: 278
ataaggaaag gttaaaaaaa gtaaaggaa ctcggcaaat ctcaccccgc ctgtttacca    60
aaaacatcac ctctagcat                                                79

<210> SEQ ID NO 279
<211> LENGTH: 78
<212> TYPE: DNA
<213> ORGANISM: Pongo sp.

<400> SEQUENCE: 279
taaggaaaga ttacaaacag taaaaggaac tcggcaaatc ttacccagct tgtttaccaa    60
aaacatcacc tctagcat                                                  78

<210> SEQ ID NO 280
<211> LENGTH: 78
<212> TYPE: DNA
<213> ORGANISM: Pongo sp.

<400> SEQUENCE: 280
taaggaaaga ttacaaaaag taaaaggaac ttggcaaatc ttatcccgcc tatttaccaa    60
aaacatcacc tctagcat                                                  78

<210> SEQ ID NO 281
<211> LENGTH: 78
<212> TYPE: DNA
<213> ORGANISM: Pongo sp.

<400> SEQUENCE: 281
taaggaaaca ttacaaaaaa gaaaaggaac tcagcaaatc ttaccccgcc tgtttaccaa    60
aaacatcacc tctagcat                                                  78

<210> SEQ ID NO 282
<211> LENGTH: 78
<212> TYPE: DNA
<213> ORGANISM: Pongo sp.

<400> SEQUENCE: 282
```

```
taaggaaaga atacaaaaag taaaaggaac tccgcaaatt ttaccccacc tgtttaccaa      60
aaacatcacc tctagcat                                                   78

<210> SEQ ID NO 283
<211> LENGTH: 76
<212> TYPE: DNA
<213> ORGANISM: Macaca mulatta

<400> SEQUENCE: 283
ggaaaggtta aaaaaagtaa aaggaacttg gcaaactcaa accccgcctg tttaccaaaa      60
acatcacctc tagcat                                                     76

<210> SEQ ID NO 284
<211> LENGTH: 78
<212> TYPE: DNA
<213> ORGANISM: Macaca mulatta

<400> SEQUENCE: 284
taaggaaaga ttcaaaaag taaaaggagc tcggcaaatc ttactcggcc tgtttaccaa       60
aaatatcacc tctagcat                                                   78

<210> SEQ ID NO 285
<211> LENGTH: 78
<212> TYPE: DNA
<213> ORGANISM: Macaca mulatta

<400> SEQUENCE: 285
taaggaaagg ttaaaaaaag gaaaggaac tcagcaaatt ttaccctgcc tgtttaccaa       60
aaacatcacc tctagcat                                                   78

<210> SEQ ID NO 286
<211> LENGTH: 79
<212> TYPE: DNA
<213> ORGANISM: Macaca mulatta

<400> SEQUENCE: 286
taaggaaagg ttaaaaaaag taaaaggaac tcggcaaact taaccccgc ctgtttacca       60 aaaacatcac ctctagcat                                                  79

<210> SEQ ID NO 287
<211> LENGTH: 78
<212> TYPE: DNA
<213> ORGANISM: Macaca mulatta

<400> SEQUENCE: 287
taaggaaagt ttacaaaaag tgaaaggaac tcagcaaatc ttaccctgcc tgtttaccaa      60
aaacatcacc tctagcat                                                   78

<210> SEQ ID NO 288
<211> LENGTH: 78
<212> TYPE: DNA
<213> ORGANISM: Macaca mulatta

<400> SEQUENCE: 288
taaggaagac tgcaaaaaag taaaaggaac atggcaaatc ttaccccatc tgtttaccaa      60
aaacatcacc tctagcat                                                   78

<210> SEQ ID NO 289
<211> LENGTH: 79
<212> TYPE: DNA
```

<213> ORGANISM: Macaca mulatta

<400> SEQUENCE: 289

```
taaggaaagg ttaaaaaaag taaaaggaac tcggcaaact caaaccccgc ctgtttacca    60
aaaacatcac ctctagcat                                                  79
```

<210> SEQ ID NO 290
<211> LENGTH: 80
<212> TYPE: DNA
<213> ORGANISM: Macaca mulatta

<400> SEQUENCE: 290

```
tcttaaggaa aggttaaaaa aaagtaaaag gaactcggca aatctaaccc cacctgttta    60
ccaaaaacat cacctccagc                                                 80
```

<210> SEQ ID NO 291
<211> LENGTH: 79
<212> TYPE: DNA
<213> ORGANISM: Macaca mulatta

<400> SEQUENCE: 291

```
taaggaaagg ttaaaaaagg taaaaggaac tcggcaaact caaaccccgc ctgtttacca    60
aaaacatcac ctctagcat                                                  79
```

<210> SEQ ID NO 292
<211> LENGTH: 78
<212> TYPE: DNA
<213> ORGANISM: Macaca mulatta

<400> SEQUENCE: 292

```
taaggaaagg ttaaaaaaag taaaaggaac tcggcaaact taaccccgcc tatttaccaa    60
aaacatcacc tctagcat                                                   78
```

<210> SEQ ID NO 293
<211> LENGTH: 78
<212> TYPE: DNA
<213> ORGANISM: Macaca mulatta

<400> SEQUENCE: 293

```
taaggaaaga ttacaaaaac taaaaggaac tctgcaaatc ttatcccacc tgtttaccaa    60
aaacatcacc tctagcat                                                   78
```

<210> SEQ ID NO 294
<211> LENGTH: 78
<212> TYPE: DNA
<213> ORGANISM: Macaca mulatta

<400> SEQUENCE: 294

```
taaggaaaga taacaaaagg taaaaggaac ttggcaaatc ttatcccacc tacttaccaa    60
aaacatcacc tctagcat                                                   78
```

<210> SEQ ID NO 295
<211> LENGTH: 78
<212> TYPE: DNA
<213> ORGANISM: Macaca mulatta

<400> SEQUENCE: 295

```
taaggaaagg ttacaaaaag taaaagaaac tcggcaaatt tcaccccgtc tgtttaccaa    60
aaacatcacc cctagcat                                                   78
```

```
<210> SEQ ID NO 296
<211> LENGTH: 78
<212> TYPE: DNA
<213> ORGANISM: Macaca mulatta

<400> SEQUENCE: 296
taaggaaaga ttacaaaaag taaaggaat tcagcaaatc ttacactgcc tgtttaccaa      60
aaacatcacc tctagcat                                                   78

<210> SEQ ID NO 297
<211> LENGTH: 77
<212> TYPE: DNA
<213> ORGANISM: Macaca mulatta

<400> SEQUENCE: 297
taaggaaagg ttaaaaaaag taaaggaac tcggcaaatt ttagcctcct gtttaccgaa      60
atcatcacct ctagcat                                                    77

<210> SEQ ID NO 298
<211> LENGTH: 78
<212> TYPE: DNA
<213> ORGANISM: Macaca mulatta

<400> SEQUENCE: 298
taaggaaagg ttaaaaaaag taaaggaac ttggcaaatt ttacccggcc tgtttaccag      60
aaacatcacc tctagcat                                                   78

<210> SEQ ID NO 299
<211> LENGTH: 78
<212> TYPE: DNA
<213> ORGANISM: Macaca mulatta

<400> SEQUENCE: 299
taaggaaaca ttacaaaaag taaaggaac ttggcaaatc ctaccctgcc tgtttaccaa      60
aaacatcacg tctagcat                                                   78

<210> SEQ ID NO 300
<211> LENGTH: 78
<212> TYPE: DNA
<213> ORGANISM: Macaca mulatta

<400> SEQUENCE: 300
taaggaaata ttacaaaaag taaaggaat ttggcaaatc atccctgcc tgtttaccaa       60 aaacatcacc tctagcat                                                   78

<210> SEQ ID NO 301
<211> LENGTH: 77
<212> TYPE: DNA
<213> ORGANISM: Macaca mulatta

<400> SEQUENCE: 301
aaggaaagtt tacaaaaagt aaaggaact cagccaatct tactctgcct gtttaccaaa      60
aacatcacct ctagcat                                                    77

<210> SEQ ID NO 302
<211> LENGTH: 78
<212> TYPE: DNA
<213> ORGANISM: Macaca mulatta

<400> SEQUENCE: 302
```

```
taaggaaaga ttacaataag taaaaggaac tcagcaaatc taaccctgcc tgtttaccaa    60
aaacatcacc tctagcat                                                  78

<210> SEQ ID NO 303
<211> LENGTH: 78
<212> TYPE: DNA
<213> ORGANISM: Macaca mulatta

<400> SEQUENCE: 303
taaggaaagg ttaaaaaaag taaaaggaac tcaacaaact taaccccgcc tgtttaccaa    60
aaacatcacc actagcat                                                  78

<210> SEQ ID NO 304
<211> LENGTH: 82
<212> TYPE: DNA
<213> ORGANISM: Macaca mulatta

<400> SEQUENCE: 304
tcttaaggaa aggttaaaaa aagtaaaagg aactcggcaa acttaaaccc cacctgttta    60
ccaaaaacat cacctctagc at                                             82

<210> SEQ ID NO 305
<211> LENGTH: 77
<212> TYPE: DNA
<213> ORGANISM: Macaca mulatta

<400> SEQUENCE: 305
taaggaaaga ttacaaaaag tataaggaac tcggaaatct taccccacct gtttaccaaa    60
aacatcacct ctagcat                                                   77

<210> SEQ ID NO 306
<211> LENGTH: 78
<212> TYPE: DNA
<213> ORGANISM: Macaca mulatta

<400> SEQUENCE: 306
taaggaaaga acacaaaaag taaaaggaac ttggcaaatt ttaccccgcc tgtttaccaa    60
aaacatcacc tctagcat                                                  78

<210> SEQ ID NO 307
<211> LENGTH: 78
<212> TYPE: DNA
<213> ORGANISM: Mus sp.

<400> SEQUENCE: 307
aaggaaagat ccaaaaagat aaaaggaact cggcaaacaa gaaccccgcc tgtttaccaa    60
aaacatcacc tctagcat                                                  78

<210> SEQ ID NO 308
<211> LENGTH: 77
<212> TYPE: DNA
<213> ORGANISM: Rattus sp.

<400> SEQUENCE: 308
taaggaaagt ttaaaaaagt aaaggaactc ggcaaacacg aaccccgcct gtttaccaaa    60
aacatctcct ctagcat                                                   77

<210> SEQ ID NO 309
<211> LENGTH: 76
<212> TYPE: DNA
```

```
<213> ORGANISM: Cavia sp.

<400> SEQUENCE: 309
ggaaagacaa acaaagcaa aaggaactcg gcaaacacaa atcccgcctg tttaccaaaa     60
acatcacctc tagcat                                                    76

<210> SEQ ID NO 310
<211> LENGTH: 77
<212> TYPE: DNA
<213> ORGANISM: Cavia sp.

<400> SEQUENCE: 310
aggaaagacg aaacaaagca aaggaactc ggcaaacata aatcctgcct gtttaccaaa     60
aacatcacct ctagcat                                                   77

<210> SEQ ID NO 311
<211> LENGTH: 77
<212> TYPE: DNA
<213> ORGANISM: Cavia sp.

<400> SEQUENCE: 311
aggaaagatg aaacaaagca aaggaactc ggcaaacaca aatcccgcct gataaccaaa     60
aacatcacct ctagcat                                                   77

<210> SEQ ID NO 312
<211> LENGTH: 84
<212> TYPE: DNA
<213> ORGANISM: Cavia sp.

<400> SEQUENCE: 312
aggaaagaca aaaaaaaaaa aaaggcaaaa ggaacacggc aaacacaaat cccgcctgtt     60
taccaaaaac atcacctcta gcat                                           84

<210> SEQ ID NO 313
<211> LENGTH: 73
<212> TYPE: DNA
<213> ORGANISM: Cavia sp.

<400> SEQUENCE: 313
ggaaagacaa aaagcaaaag gaactcggta aacataaatc ctgcctgttt accaaaaaca     60
tcacctctag cat                                                       73

<210> SEQ ID NO 314
<211> LENGTH: 77
<212> TYPE: DNA
<213> ORGANISM: Cavia sp.

<400> SEQUENCE: 314
ggaaagacaa acaaagcaa aaggaactcg gcaaacacaa atcccgcctg tttaaccaaa     60
aacaccacct ctagcat                                                   77

<210> SEQ ID NO 315
<211> LENGTH: 76
<212> TYPE: DNA
<213> ORGANISM: Cavia sp.

<400> SEQUENCE: 315
aggaaagaca aaacaaagca aaggaactc ggcaaacaca aatcccgcct gttaccaaaa     60
acatcacctc tagcat                                                    76
```

```
<210> SEQ ID NO 316
<211> LENGTH: 76
<212> TYPE: DNA
<213> ORGANISM: Unknown
<220> FEATURE:
<223> OTHER INFORMATION: Description of Unknown: Cat oligonucleotide

<400> SEQUENCE: 316
ggaaagatta aagaagtaa aaggaactcg gcaaacacaa gccccgcctg tttaccaaaa      60
acatcacctc tagcat                                                    76

<210> SEQ ID NO 317
<211> LENGTH: 79
<212> TYPE: DNA
<213> ORGANISM: Unknown
<220> FEATURE:
<223> OTHER INFORMATION: Description of Unknown: Cat oligonucleotide

<400> SEQUENCE: 317
taaggaaaga ttaaaggaag tgaaaggaac ttggcaaatg caaacccgc ctgtttacca      60 aaaacatcac ctctagcat                                                 79

<210> SEQ ID NO 318
<211> LENGTH: 78
<212> TYPE: DNA
<213> ORGANISM: Unknown
<220> FEATURE:
<223> OTHER INFORMATION: Description of Unknown: Cat oligonucleotide

<400> SEQUENCE: 318
aaggaaagat gaaacaaagt aaaaggaact cagcgaacac aaaccccacc tgtttaccag    60
taaaatcacc tctagcat                                                  78

<210> SEQ ID NO 319
<211> LENGTH: 80
<212> TYPE: DNA
<213> ORGANISM: Unknown
<220> FEATURE:
<223> OTHER INFORMATION: Description of Unknown: Cat oligonucleotide

<400> SEQUENCE: 319
ataaggaaag attaaaagaa gtaaaaggaa ctcggcaaac acaagtcccg cctgtttacc    60
gaaaacatca cctctagcat                                                80

<210> SEQ ID NO 320
<211> LENGTH: 76
<212> TYPE: DNA
<213> ORGANISM: Unknown
<220> FEATURE:
<223> OTHER INFORMATION: Description of Unknown: Cat oligonucleotide

<400> SEQUENCE: 320
ggaaagatta aagaagtaa aaggaactcg gcaaacacaa gcctcgcctg tttaccaaaa     60
acatcacctc taacat                                                    76

<210> SEQ ID NO 321
<211> LENGTH: 80
<212> TYPE: DNA
<213> ORGANISM: Equus ferus

<400> SEQUENCE: 321
ataaggaaag attaaaagaa gtaaaaggaa ctcggcaaac acaaaccccg cctgtttacc    60
```

```
aaaaacatca cctctagcat                                              80

<210> SEQ ID NO 322
<211> LENGTH: 81
<212> TYPE: DNA
<213> ORGANISM: Equus ferus

<400> SEQUENCE: 322
cataaggaaa gattaaaaga agtaaaagga actcggcaaa cacaaacccc gcatgtttac   60
cgaaaacatc acctctagca t                                            81

<210> SEQ ID NO 323
<211> LENGTH: 79
<212> TYPE: DNA
<213> ORGANISM: Equus ferus

<400> SEQUENCE: 323
taaggaaaga tttaaaaaag taaaaggaac tcagcaaaca caaactccgc ctgtttacca   60
aaaacatcac ctctagcat                                               79

<210> SEQ ID NO 324
<211> LENGTH: 79
<212> TYPE: DNA
<213> ORGANISM: Ornithorhynchus anatinus

<400> SEQUENCE: 324
taaggaaaga ttaaaggag taaaaggaac tcggcaaact aggatttcgc ctgtttacca    60
aaaacatcgc ctctagcat                                               79

<210> SEQ ID NO 325
<211> LENGTH: 63
<212> TYPE: DNA
<213> ORGANISM: Pan sp.

<400> SEQUENCE: 325
atgttggatc aggacatccc gatggtgcag ccgctattaa aggttcgttt gttcaacgat   60
taa                                                                63

<210> SEQ ID NO 326
<211> LENGTH: 63
<212> TYPE: DNA
<213> ORGANISM: Pan sp.

<400> SEQUENCE: 326
atgttggatc aggacatccc gatggtgcag ccgctattaa aggttcgttt gttcaacgat   60
taa                                                                63

<210> SEQ ID NO 327
<211> LENGTH: 61
<212> TYPE: DNA
<213> ORGANISM: Pan sp.

<400> SEQUENCE: 327
atgttggatc aggacatgct gatggtgcag ccgctatcaa aggttcgttt gttcaacgat   60
t                                                                  61

<210> SEQ ID NO 328
<211> LENGTH: 63
<212> TYPE: DNA
<213> ORGANISM: Pan sp.
```

-continued

<400> SEQUENCE: 328
atgttggatc aggacatcct aatggtgcag ctgctattaa gggtttgttt cttcagtgat    60
taa                                                                 63

<210> SEQ ID NO 329
<211> LENGTH: 63
<212> TYPE: DNA
<213> ORGANISM: Pan sp.

<400> SEQUENCE: 329
atgttggatc aggacatccc gatggtgcag ccgctattaa aggttcgttt gttcaacgat    60
taa                                                                 63

<210> SEQ ID NO 330
<211> LENGTH: 63
<212> TYPE: DNA
<213> ORGANISM: Pan sp.

<400> SEQUENCE: 330
atgttggatc aggacatcct gatggtgcag ccgctattaa aggttcgttt gttcaacgat    60
taa                                                                 63

<210> SEQ ID NO 331
<211> LENGTH: 63
<212> TYPE: DNA
<213> ORGANISM: Pan sp.

<400> SEQUENCE: 331
atgttggatc aggacatccc gatggtgcag ccgctattaa aggttcgttt gttcaacgat    60
taa                                                                 63

<210> SEQ ID NO 332
<211> LENGTH: 62
<212> TYPE: DNA
<213> ORGANISM: Pan sp.

<400> SEQUENCE: 332
atgttggatc aggacatcct aatggtgcag ccggtattaa gggttcgttt gttcaatgat    60
ta                                                                  62

<210> SEQ ID NO 333
<211> LENGTH: 63
<212> TYPE: DNA
<213> ORGANISM: Pongo sp.

<400> SEQUENCE: 333
atgttggatc aggacatcct aatggtgcag ccgctattaa aggttcgttt gttcaacgat    60
taa                                                                 63

<210> SEQ ID NO 334
<211> LENGTH: 63
<212> TYPE: DNA
<213> ORGANISM: Pongo sp.

<400> SEQUENCE: 334
atgttggatc aggacatcct aatggtgtag ctgctatcaa gggttcgttt gttccatgat    60
taa                                                                 63

<210> SEQ ID NO 335

<211> LENGTH: 57
<212> TYPE: DNA
<213> ORGANISM: Pongo sp.

<400> SEQUENCE: 335
atgttggatc aggacatcct gatggtgcag ccgctatcaa agtttcattt gttcaac    57

<210> SEQ ID NO 336
<211> LENGTH: 63
<212> TYPE: DNA
<213> ORGANISM: Pongo sp.

<400> SEQUENCE: 336
atgttggatc acgtcatcct aatggtgtaa ctgctattaa aggttcgttt gttcgacgat    60
tga    63

<210> SEQ ID NO 337
<211> LENGTH: 63
<212> TYPE: DNA
<213> ORGANISM: Pongo sp.

<400> SEQUENCE: 337
atgttggatc aggacatcct aatggtgtag ccactattaa gggttcgttt attcaacaat    60
taa    63

<210> SEQ ID NO 338
<211> LENGTH: 63
<212> TYPE: DNA
<213> ORGANISM: Pongo sp.

<400> SEQUENCE: 338
atgttggatc aggacatcct aatggtgtag ctgctattaa gggtttattt gttcaacaat    60
taa    63

<210> SEQ ID NO 339
<211> LENGTH: 63
<212> TYPE: DNA
<213> ORGANISM: Pongo sp.

<400> SEQUENCE: 339
atgttggatc aggacatccc aatggtgcag ccgctattaa aggttcgttt gttcaacgat    60
taa    63

<210> SEQ ID NO 340
<211> LENGTH: 62
<212> TYPE: DNA
<213> ORGANISM: Pongo sp.

<400> SEQUENCE: 340
atgttggatc aggacatcct aatggtgtag ctgctatcaa gggttcgttt gttcaatgat    60
ta    62

<210> SEQ ID NO 341
<211> LENGTH: 55
<212> TYPE: DNA
<213> ORGANISM: Pongo sp.

<400> SEQUENCE: 341
atgttggatc aggacatcct aatggtgtag ccgctaataa ggttcgtttg ttcaa    55

<210> SEQ ID NO 342

-continued

```
<211> LENGTH: 63
<212> TYPE: DNA
<213> ORGANISM: Pongo sp.

<400> SEQUENCE: 342
atgttggatc aggacatcct aatggtgcag ccgctattaa aggttcgttt gttcaacgat      60
taa                                                                   63

<210> SEQ ID NO 343
<211> LENGTH: 62
<212> TYPE: DNA
<213> ORGANISM: Pongo sp.

<400> SEQUENCE: 343
atgttggatc aggacatcct aatggtgcag ccgctattaa gggttcgttt gttcaatgat      60
ta                                                                    62

<210> SEQ ID NO 344
<211> LENGTH: 62
<212> TYPE: DNA
<213> ORGANISM: Pongo sp.

<400> SEQUENCE: 344
atgttggatc aggacatccc aagggtgcag ctgctattaa agtttcgttt gttcaatgat      60
ta                                                                    62

<210> SEQ ID NO 345
<211> LENGTH: 63
<212> TYPE: DNA
<213> ORGANISM: Macaca mulatta

<400> SEQUENCE: 345
atgttggatc aggacatcct aatggtgcag cagctatcaa gggttcgttt gttcaacgat      60
taa                                                                   63

<210> SEQ ID NO 346
<211> LENGTH: 63
<212> TYPE: DNA
<213> ORGANISM: Macaca mulatta

<400> SEQUENCE: 346
atgttggatc aggacatcct aatggtgcag cagctatcaa gggttctttt gttcaacaat      60
taa                                                                   63

<210> SEQ ID NO 347
<211> LENGTH: 63
<212> TYPE: DNA
<213> ORGANISM: Macaca mulatta

<400> SEQUENCE: 347
atgttgcatc aggacatcct aatggtgtag ccgctatcaa gggttcgttt gttcaatgat      60
taa                                                                   63

<210> SEQ ID NO 348
<211> LENGTH: 63
<212> TYPE: DNA
<213> ORGANISM: Macaca mulatta

<400> SEQUENCE: 348
atgttggatc aggacatcct gatggtgtag cagctatcaa gggttcgttt gttcaacgat      60
```

```
taa                                                               63

<210> SEQ ID NO 349
<211> LENGTH: 63
<212> TYPE: DNA
<213> ORGANISM: Mus sp.

<400> SEQUENCE: 349
atgttggatc aggacatccc aatggtgtag aagctattaa tggttcgttt gttcaacgat    60
taa                                                               63

<210> SEQ ID NO 350
<211> LENGTH: 63
<212> TYPE: DNA
<213> ORGANISM: Rattus sp.

<400> SEQUENCE: 350
atgttggatc aggacatccc aatggtgcag aagctattaa tggttcgttt gttcaacgat    60
taa                                                               63

<210> SEQ ID NO 351
<211> LENGTH: 63
<212> TYPE: DNA
<213> ORGANISM: Unknown
<220> FEATURE:
<223> OTHER INFORMATION: Description of Unknown: Opossum oligonucleotide

<400> SEQUENCE: 351
atgttggatc aggacacccc aatggtgcag ccgctattaa aggttcgttt gttcaacgat    60
taa                                                               63

<210> SEQ ID NO 352
<211> LENGTH: 63
<212> TYPE: DNA
<213> ORGANISM: Ornithorhynchus anatinus

<400> SEQUENCE: 352
atgttggatc aggacatcca aatggtgcag ccgctattaa tggttcgttt gttcaacgat    60
taa                                                               63

<210> SEQ ID NO 353
<211> LENGTH: 63
<212> TYPE: DNA
<213> ORGANISM: Cavia sp.

<400> SEQUENCE: 353
atgttggatc aggacatcct aatggtgcag cagctattaa gggttcgttt gttcaacgat    60
taa                                                               63

<210> SEQ ID NO 354
<211> LENGTH: 63
<212> TYPE: DNA
<213> ORGANISM: Cavia sp.

<400> SEQUENCE: 354
atgttggatc tggtcatcct aatggtgcag ccgctatcga gggtccgttt gttcaacgat    60
taa                                                               63

<210> SEQ ID NO 355
<211> LENGTH: 63
<212> TYPE: DNA
```

```
<213> ORGANISM: Cavia sp.

<400> SEQUENCE: 355
atgctggatc aggacgtcct aatggggcag ccactattaa gtgttcgttt gttcaacgat    60
tga                                                                  63

<210> SEQ ID NO 356
<211> LENGTH: 63
<212> TYPE: DNA
<213> ORGANISM: Cavia sp.

<400> SEQUENCE: 356
atgttggatc aggacatcct aatggtgagg cggctattaa gggttcactt gttcaacgat    60
taa                                                                  63

<210> SEQ ID NO 357
<211> LENGTH: 63
<212> TYPE: DNA
<213> ORGANISM: Cavia sp.

<400> SEQUENCE: 357
atgttggatc aggacatcct aatggtgcag cagctattga gggttcgttt gttcaacgat    60
taa                                                                  63

<210> SEQ ID NO 358
<211> LENGTH: 63
<212> TYPE: DNA
<213> ORGANISM: Unknown
<220> FEATURE:
<223> OTHER INFORMATION: Description of Unknown: Cat oligonucleotide

<400> SEQUENCE: 358
atgttggatc aggacatccc gatggtgcag cagctatcaa aggttcgttt gttcaacgat    60
taa                                                                  63

<210> SEQ ID NO 359
<211> LENGTH: 63
<212> TYPE: DNA
<213> ORGANISM: Unknown
<220> FEATURE:
<223> OTHER INFORMATION: Description of Unknown: Cat oligonucleotide

<400> SEQUENCE: 359
atgttggatc aagacatccc aatagtacag cagctatcaa aggtttgttt gttcaacgat    60
taa                                                                  63

<210> SEQ ID NO 360
<211> LENGTH: 63
<212> TYPE: DNA
<213> ORGANISM: Unknown
<220> FEATURE:
<223> OTHER INFORMATION: Description of Unknown: Cat oligonucleotide

<400> SEQUENCE: 360
atgttggatc aagacatccc aatagtacag cagctatcaa aggtttgttt gttcaacgat    60
taa                                                                  63

<210> SEQ ID NO 361
<211> LENGTH: 57
<212> TYPE: DNA
<213> ORGANISM: Unknown
<220> FEATURE:
```

<223> OTHER INFORMATION: Description of Unknown: Cat oligonucleotide

<400> SEQUENCE: 361
atgttggatc aggacatccc gatggtgcag cagctatcaa agtttcgttt gttcaac         57

<210> SEQ ID NO 362
<211> LENGTH: 63
<212> TYPE: DNA
<213> ORGANISM: Unknown
<220> FEATURE:
<223> OTHER INFORMATION: Description of Unknown: Cat oligonucleotide

<400> SEQUENCE: 362
atgttggatc aggacatccc gatggtgcag cagctagcga aggttcgttt gttggacgat     60
taa                                                                   63

<210> SEQ ID NO 363
<211> LENGTH: 63
<212> TYPE: DNA
<213> ORGANISM: Canis lupus

<400> SEQUENCE: 363
atgttggatc aggacatcct aatggtgcag cagctattaa gggttcgttt gttcaacgat     60
taa                                                                   63

<210> SEQ ID NO 364
<211> LENGTH: 63
<212> TYPE: DNA
<213> ORGANISM: Canis lupus

<400> SEQUENCE: 364
atgttggatc aggacatcct aatggtgcag cagctattaa gggttagttt gttcaacaat     60
taa                                                                   63

<210> SEQ ID NO 365
<211> LENGTH: 63
<212> TYPE: DNA
<213> ORGANISM: Equus ferus

<400> SEQUENCE: 365
atgttggatc aagacatcct aatggtgcaa ccgctattaa gggttcgttt gttcaacgat     60
taa                                                                   63

<210> SEQ ID NO 366
<211> LENGTH: 63
<212> TYPE: DNA
<213> ORGANISM: Equus ferus

<400> SEQUENCE: 366
atgttggatc aagacatcct aatggtgcaa ccgctattaa gggtttgttt gttcaacgat     60
taa                                                                   63

<210> SEQ ID NO 367
<211> LENGTH: 63
<212> TYPE: DNA
<213> ORGANISM: Bos sp.

<400> SEQUENCE: 367
atgttggatc aggacatcct gatggtgcaa ccgctatcaa aggttcgttt gttcaacgat     60
taa                                                                   63

```
<210> SEQ ID NO 368
<211> LENGTH: 63
<212> TYPE: DNA
<213> ORGANISM: Gallus gallus

<400> SEQUENCE: 368
atgttggatc aggacaacct aatggtgcaa ccgctattaa gggttcgttt gttcaacgat      60
taa                                                                   63

<210> SEQ ID NO 369
<211> LENGTH: 63
<212> TYPE: DNA
<213> ORGANISM: Taeniopygia guttata

<400> SEQUENCE: 369
atgttggatc aggacatcct agtggtgcag ccgctactaa gggttcgttt gttcaacgat      60
taa                                                                   63

<210> SEQ ID NO 370
<211> LENGTH: 63
<212> TYPE: DNA
<213> ORGANISM: Taeniopygia guttata

<400> SEQUENCE: 370
atgttggatc aggacatcct agtggtgcag ccactactaa gggttcgttt gttcaatgat      60
tta                                                                   63

<210> SEQ ID NO 371
<211> LENGTH: 63
<212> TYPE: DNA
<213> ORGANISM: Unknown
<220> FEATURE:
<223> OTHER INFORMATION: Description of Unknown: Lizard oligonucleotide

<400> SEQUENCE: 371
atgttggatc aggacaccca aatggtgcag ccgctattaa aggttcgttt gttcaacgat      60
taa                                                                   63

<210> SEQ ID NO 372
<211> LENGTH: 63
<212> TYPE: DNA
<213> ORGANISM: Xenopus tropicalis

<400> SEQUENCE: 372
atgttggatc agggcatccc agtggtgcag ccgctactaa aggttcgttt gttcaacgat      60
taa                                                                   63

<210> SEQ ID NO 373
<211> LENGTH: 63
<212> TYPE: DNA
<213> ORGANISM: Danio rerio

<400> SEQUENCE: 373
atgttggatc aggacatcct aatggtgcag ccgctattaa gggttcgttt gttcaacgat      60
taa                                                                   63

<210> SEQ ID NO 374
<211> LENGTH: 63
<212> TYPE: DNA
<213> ORGANISM: Tetraodon sp.
```

```
<400> SEQUENCE: 374
atgttggatc aggacatcct aatggtgcag ccgctattaa gggttcgttt gttcaacgat    60
taa                                                                 63

<210> SEQ ID NO 375
<211> LENGTH: 63
<212> TYPE: DNA
<213> ORGANISM: Unknown
<220> FEATURE:
<223> OTHER INFORMATION: Description of Unknown: Fugu oligonucleotide

<400> SEQUENCE: 375
atgttggatc aggacatcct aatggtgcag ccgctattaa aggttcgttt gttcaacgat    60
taa                                                                 63

<210> SEQ ID NO 376
<211> LENGTH: 63
<212> TYPE: DNA
<213> ORGANISM: Unknown
<220> FEATURE:
<223> OTHER INFORMATION: Description of Unknown: Stickleback
      oligonucleotide

<400> SEQUENCE: 376
atgttggatc aggacatcct aatggtgcag ccgctattaa gggttcgttt gttcaacgat    60
taa                                                                 63

<210> SEQ ID NO 377
<211> LENGTH: 63
<212> TYPE: DNA
<213> ORGANISM: Unknown
<220> FEATURE:
<223> OTHER INFORMATION: Description of Unknown: Medaka oligonucleotide

<400> SEQUENCE: 377
atgttggatc aggacatcct aatggtgcag ccgctattaa gggtttgttt gttcaacaat    60
taa                                                                 63

<210> SEQ ID NO 378
<211> LENGTH: 63
<212> TYPE: DNA
<213> ORGANISM: Unknown
<220> FEATURE:
<223> OTHER INFORMATION: Description of Unknown: Lamprey oligonucleotide

<400> SEQUENCE: 378
atgttggatc ggggcacccc aatggcgcaa aagctattaa aggttcgttt gttcaacgat    60
taa                                                                 63

<210> SEQ ID NO 379
<211> LENGTH: 33
<212> TYPE: PRT
<213> ORGANISM: Cavia sp.

<400> SEQUENCE: 379

Met Leu Glu Val Met Phe Leu Val Asn Arg Arg Asp Leu Cys Leu Pro
1               5                   10                  15

Ser Ser Phe Cys Phe Val Leu Ser Phe Leu Ser Ser Thr Pro Val Ser
            20                  25                  30

Gly
```

```
<210> SEQ ID NO 380
<211> LENGTH: 24
<212> TYPE: PRT
<213> ORGANISM: Canis lupus

<400> SEQUENCE: 380

Met Leu Pro Leu His Gly Gln Asp Thr Ala Ala Val Lys Gln Val Ser
1               5                   10                  15

Pro Gly Arg Gln Cys Leu Gln Tyr
            20

<210> SEQ ID NO 381
<211> LENGTH: 29
<212> TYPE: PRT
<213> ORGANISM: Bos sp.

<400> SEQUENCE: 381

Met Leu Pro Leu His Gly Gln Asp Thr Ala Ala Val Lys Gln Leu Ser
1               5                   10                  15

Leu Gly Arg Gln Cys Leu Gln Tyr Trp Glu Cys Trp Arg
            20                  25

<210> SEQ ID NO 382
<211> LENGTH: 72
<212> TYPE: DNA
<213> ORGANISM: Macaca mulatta

<400> SEQUENCE: 382 ttacccatc tgtttaccaa aaacatcacc tctagcatta ccagtatgag agtcactgcc    60
tgcccagcac at                                                      72

<210> SEQ ID NO 383
<211> LENGTH: 74
<212> TYPE: DNA
<213> ORGANISM: Macaca mulatta

<400> SEQUENCE: 383
taaccccgcc tatttaccaa aaacatcacc tctagcatta ccagtattag aggcaccgcc    60
tgcccagtga caca                                                     74

<210> SEQ ID NO 384
<211> LENGTH: 70
<212> TYPE: DNA
<213> ORGANISM: Macaca mulatta

<400> SEQUENCE: 384
ccgcctgttt accaaaaaca tcacctctag cattgctagt attagaggca ctgcctgccc    60
agtgacacat                                                          70

<210> SEQ ID NO 385
<211> LENGTH: 75
<212> TYPE: DNA
<213> ORGANISM: Macaca mulatta

<400> SEQUENCE: 385
taaccccgcc tgtttaccaa aaacatcacc actagcatta ccagtattag aggcaccgcc    60
tgcccattga cacat                                                    75

<210> SEQ ID NO 386
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      6xHis tag

<400> SEQUENCE: 386

His His His His His His
1               5

<210> SEQ ID NO 387
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 387

His His His His His His His His His His
1               5                   10
```